US010182770B2

(12) United States Patent
Asianto et al.

(10) Patent No.: US 10,182,770 B2
(45) Date of Patent: Jan. 22, 2019

(54) SMART DEVICES THAT CAPTURE IMAGES AND SENSED SIGNALS

(71) Applicant: EINS Technology PTE LTD, Singapore (SG)

(72) Inventors: Robby Asianto, Singapore (SG); Jun Lin Wong, Singapore (SG)

(73) Assignee: EINS TECHNOLOGY PTE LTD, Singapore (SG)

( * ) Notice: Subject to any disclaimer, the term of this patent is extended or adjusted under 35 U.S.C. 154(b) by 0 days.

(21) Appl. No.: 15/747,781

(22) PCT Filed: Jul. 27, 2016

(86) PCT No.: PCT/SG2016/050356
§ 371 (c)(1),
(2) Date: Jan. 26, 2018

(87) PCT Pub. No.: WO2017/018941
PCT Pub. Date: Feb. 2, 2017

(65) Prior Publication Data
US 2018/0220973 A1 Aug. 9, 2018

(30) Foreign Application Priority Data

Jul. 28, 2015 (SG) .......................... 10201505876Q

(51) Int. Cl.
*G08B 25/10* (2006.01)
*A61B 5/00* (2006.01)
(Continued)

(52) U.S. Cl.
CPC .......... *A61B 5/7465* (2013.01); *A61B 5/0022* (2013.01); *A61B 5/11* (2013.01);
(Continued)

(58) Field of Classification Search
CPC ........ F24F 11/30; F24F 11/0001; F24F 11/62; F24F 11/63; F24F 11/58; F24F 2110/10;
(Continued)

(56) References Cited

U.S. PATENT DOCUMENTS

2004/0006492 A1* 1/2004 Watanabe ............ A61B 5/0002
705/2
2014/0091945 A1* 4/2014 Rivas ..................... A61B 5/113
340/870.01
(Continued)

FOREIGN PATENT DOCUMENTS

JP 2003224674 A 8/2003
JP 2004305239 A 11/2004
(Continued)

OTHER PUBLICATIONS

International Search Report based on application No. PCT/SG2016/050356 (5 pages) dated Nov. 29, 2016 (Reference Purpose Only).

*Primary Examiner* — Daniel Previl
(74) *Attorney, Agent, or Firm* — Viering Jentschura & Partner MBB

(57) ABSTRACT

Various aspects provide a system for monitoring and/or analyzing physical states, positions, activities, and/or surroundings corresponding to a plurality of users. The smart devices include: a first processing unit; a first set of sensors for acquiring or generating signals corresponding to at least one physiologic parameter of the user; a second set of sensors including at least one of an accelerometer, a gyroscope, and a geospatial coordinate sensor; a set of image capture devices for capturing images of an environment external to the smart device and generating image data corresponding to each captured image; and a memory storing program instructions that when executed by the first processing unit cause the communication subsystem to wirelessly transmit sensed signals and image data to an (Continued)

electronic or computing destination remote from or external to the smart device; and a set of servers for network communication with the set of smart devices.

16 Claims, 28 Drawing Sheets

(51) Int. Cl.
    *A61B 5/11*         (2006.01)
    *G06F 19/00*      (2018.01)
    *G16H 40/67*      (2018.01)
    *H04N 5/232*      (2006.01)

(52) U.S. Cl.
    CPC ............ *A61B 5/1117* (2013.01); *A61B 5/681* (2013.01); *A61B 5/6898* (2013.01); *G06F 19/00* (2013.01); *G16H 40/67* (2018.01); *H04N 5/23238* (2013.01)

(58) Field of Classification Search
    CPC ............... F24F 2110/20; F24F 2110/50; F24F 2120/10; F24F 2120/20; G05B 19/042; G05B 2219/2614; G05B 15/02; G05B 19/04; G05B 2219/2642; H05B 37/0272; H05B 33/0854; H05B 33/0872; H05B 37/0209; H05B 37/0218; H05B 37/0227; F21K 9/232; F21K 9/237; F21K 9/238; F21S 9/02; F21V 23/0442; F21V 23/045; F21Y 2115/10; H01R 33/94; H01R 33/9453; H02J 13/00; H02J 9/06; H02J 9/061; Y02B 20/48; A45B 17/00; A45B 2025/003; A45B 2200/1009; A45B 2200/1018; A45B 2200/1027; A45B 25/18; A45B 15/00; A45B 2017/005; A45B 2023/0012; A45B 2200/1036; A45B 2200/1045; A45B 23/00; A45B 25/02; A45B 25/143; A45B 25/165; A45B 3/04; A45B 3/08; A61B 5/0022; A61B 5/11; A61B 5/1117; A61B 5/681; A61B 5/6898; A61B 5/7465; G06F 19/00; G08B 21/182; G16H 40/67; H04N 1/00103; H04N 2201/0055; H04N 2201/0084; H04N 5/23206; H04N 5/23216; H04N 5/23222; H04N 5/23238; H04N 5/23293; H04N 5/23296; H04N 5/247; H04N 5/332
    USPC .............. 340/539.1, 539.11, 539.12, 539.17, 340/995.16, 995.17, 995.12
    See application file for complete search history.

(56) References Cited

U.S. PATENT DOCUMENTS

| | | | |
|---|---|---|---|
| 2015/0182130 A1* | 7/2015 | Utter, II | ............... A61B 5/0205 600/483 |
| 2016/0255697 A1* | 9/2016 | Bhide | ....................... H02J 9/06 315/161 |

FOREIGN PATENT DOCUMENTS

| | | |
|---|---|---|
| JP | 2012100005 A | 5/2012 |
| JP | 2014229199 A | 12/2014 |

* cited by examiner

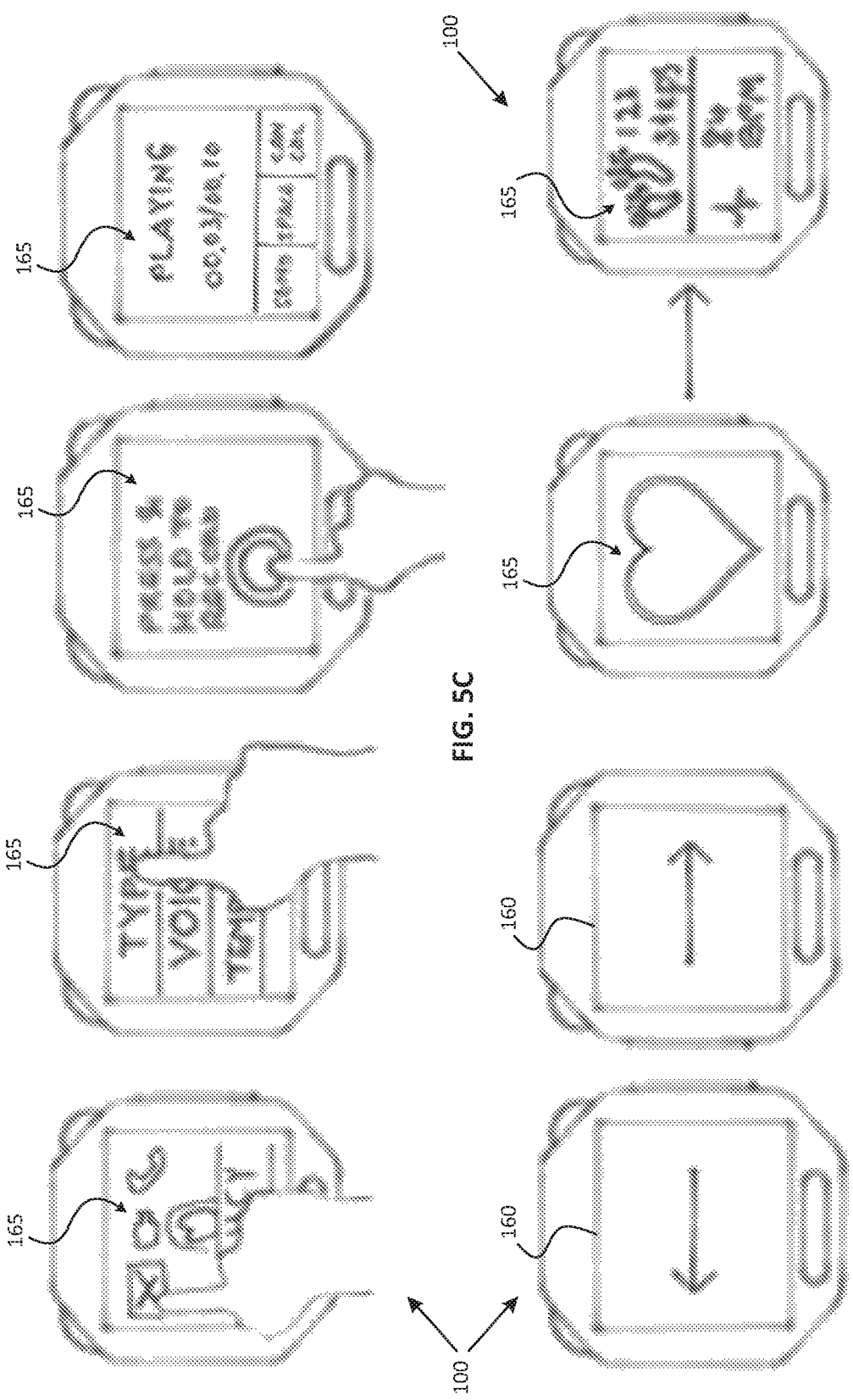

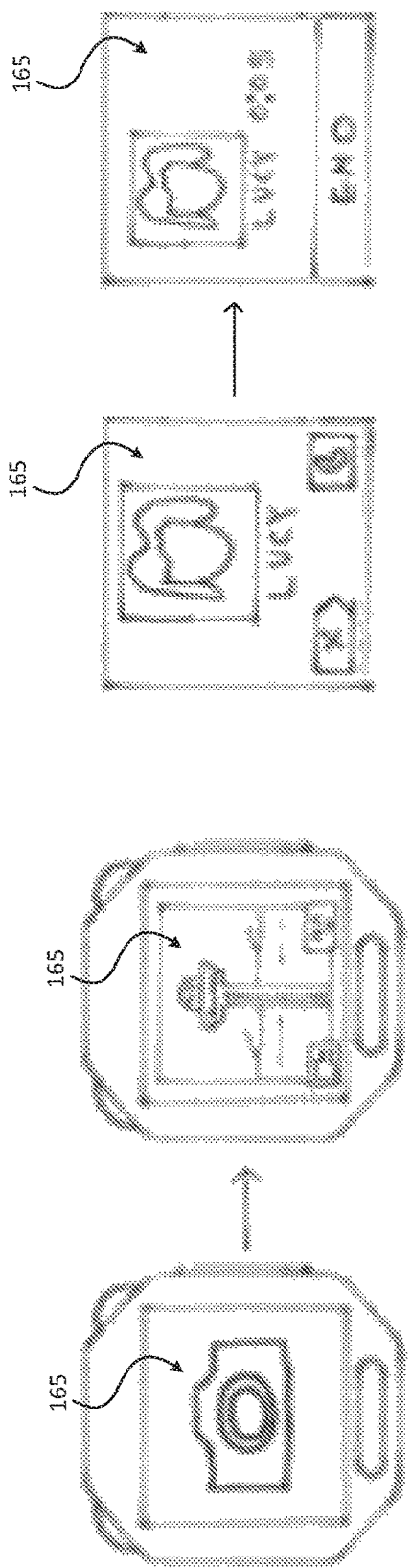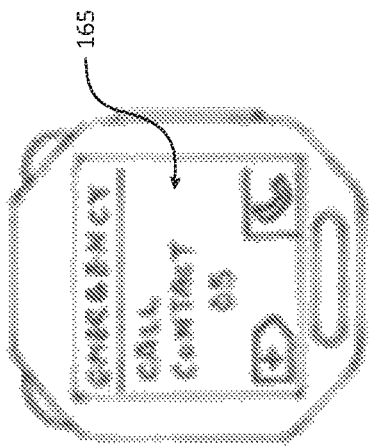

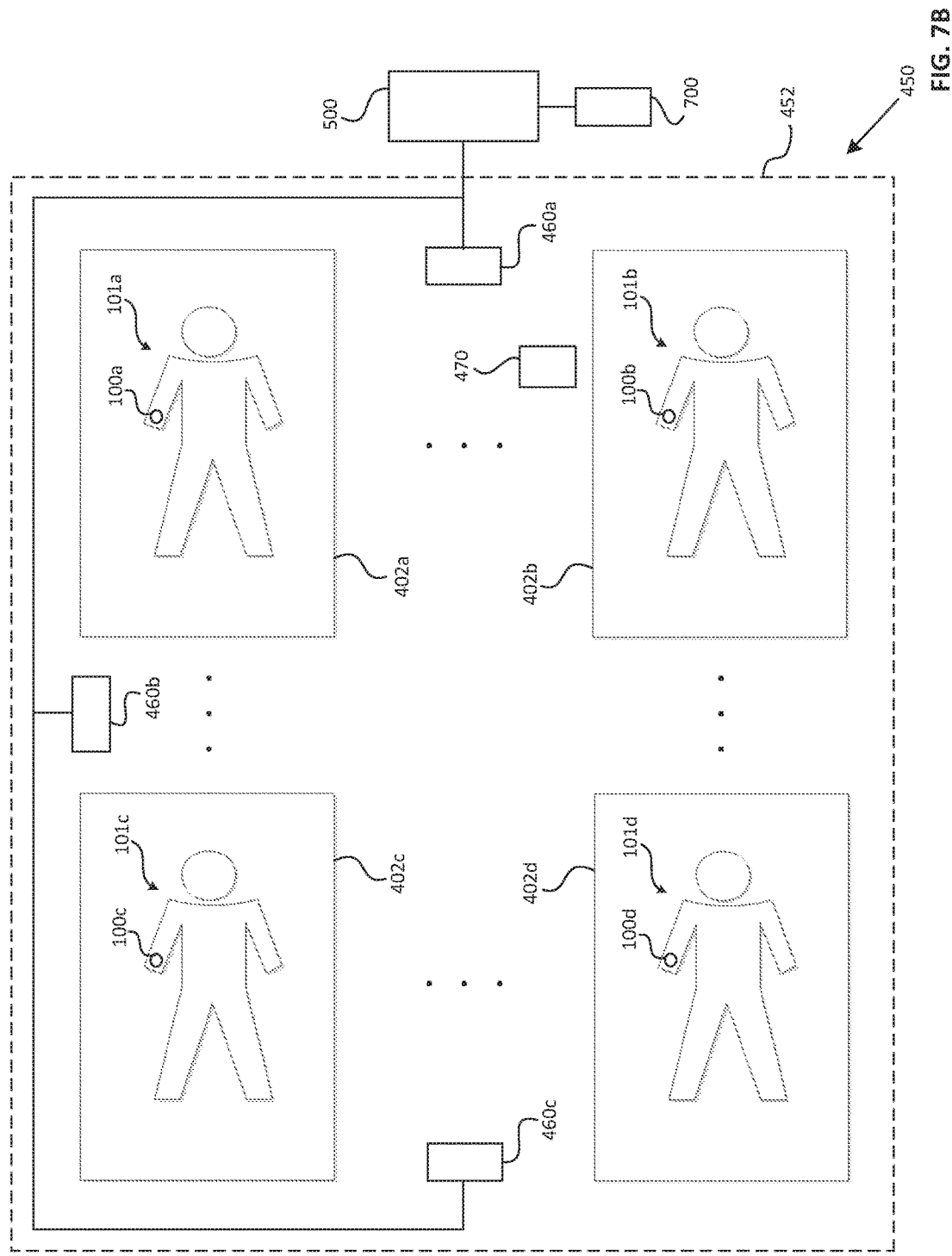

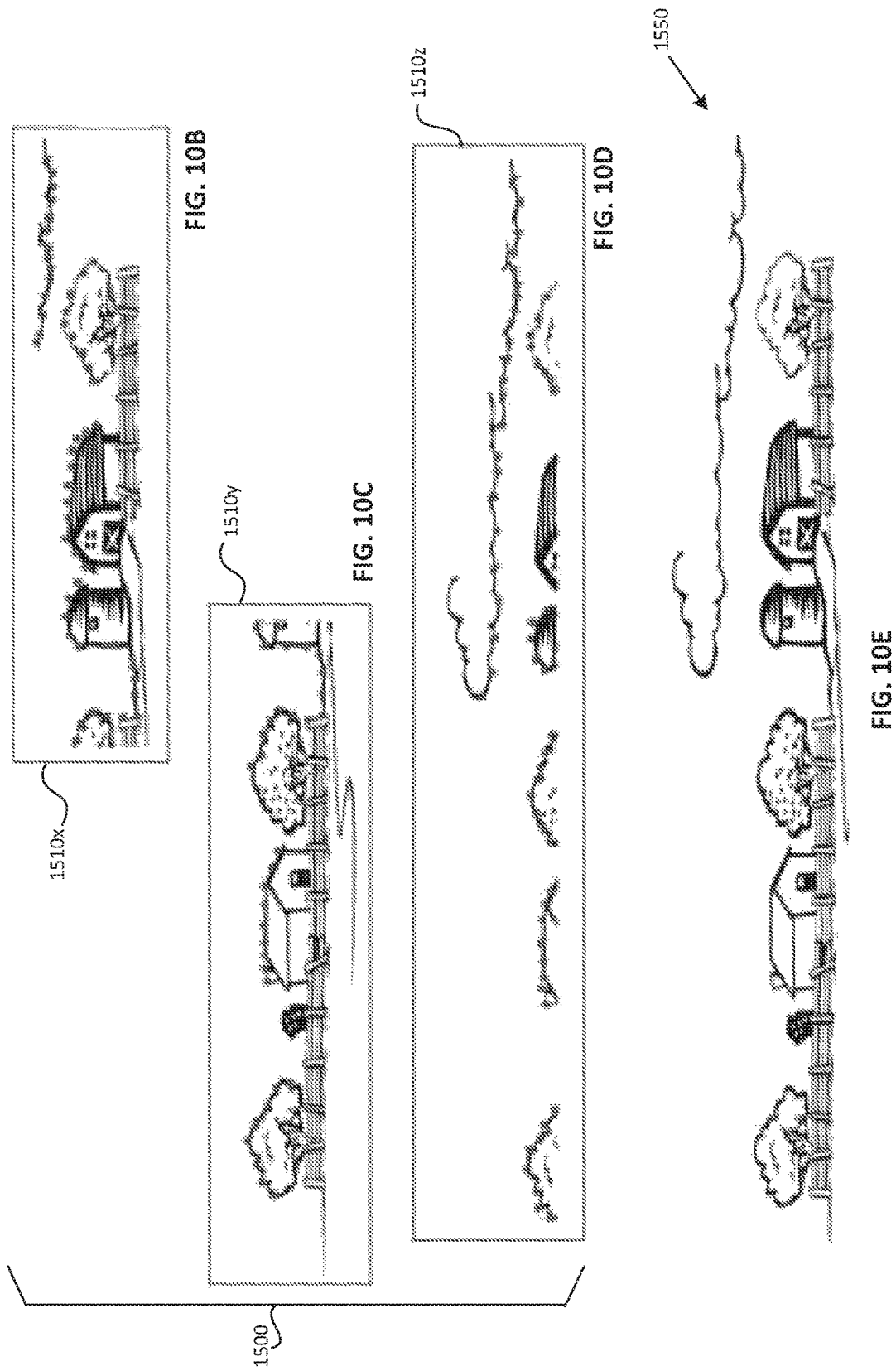

SMART DEVICES THAT CAPTURE IMAGES AND SENSED SIGNALS

RELATED APPLICATIONS

The present application is a national stage entry according to 35 U.S.C. § 371 of PCT application No.: PCT/SG2016/050356 filed on Jul. 27, 2016, which claims priority from Singapore application No.: 10201505876Q filed on Jul. 28, 2015 and is incorporated herein by reference in its entirety.

TECHNICAL FIELD

Aspects of present disclosure relate generally to image processing operations associated with portable/wearable smart devices/objects, such as smartwatches or smart clothing accessories. In particular aspects, a user's portable/wearable smart device carries a set of sensors and a set of image capture devices, and is configured for (a) acquiring and processing particular sensed signals generated using the set of sensors; (b) capturing one or more images of the user's environment along one or more smart device spatial axes; and (c) communicating sensed signals and captured image data to a set of remote servers configured for (i) analyzing the sensed signals and captured image data to determine the user's physical state(s), behavior(s), and/or environment(s) or orientation(s) therein, such as whether the user has fallen; and (ii) selectively issuing alerts directed to specific/target individuals and/or organizations based upon such analysis.

BACKGROUND

Portable smart devices such as smartphones have become ubiquitous in the modern world. Smart device manufacturers have introduced wearable smart devices, such as smartwatches, in an attempt to provide users with additional smart device convenience and capabilities. Attempts have been made to provide smartwatches that can assist particular types of users such as elderly or disabled individuals, and which are intended to address specific problems faced by such users. For instance, smartwatches carrying sensors such as accelerometers and/or gyroscopes have been configured to determine whether signals generated by the sensors indicate whether the user has experienced a sudden force or sharp impact, which may indicate that the user has fallen. If so, the user's smartwatch is further configured to issue an alert to another party such as a family member, who may be able to responsively address the user's situation. However, sensor signals generated by existing smartwatches provide an undesirably limited range of information relative to what the user is actually experiencing, and thus existing smartwatches issue an undesirably large number of "false alerts." A need exists to solve this problem.

SUMMARY

In accordance with an aspect of the present disclosure, a smart device (e.g., a smartwatch) that is portable and/or wearable by a smart device user has an x-axis, a y-axis, and a z-axis defined relative to portions of an outer smart device periphery, wherein the x-axis, the y-axis, and the z-axis are orthogonal or approximately orthogonal to each other, where the smart device includes: a set of processing units; a set of sensors coupled to the set of processing units, the set of sensors configured for acquiring or generating sensed signals including sensed signals corresponding to at least one physiologic parameter of the smart device user; a set of image capture devices configured for capturing images of an environment external to the smart device; and a memory coupled to the set of processing units and storing program instructions executable thereby, including: a first set of program instructions that when executed analyzes sensing signals output by the set of sensors including the sensed signals corresponding to the at least one physiologic parameter, and selectively actuates the set of image capture devices to automatically capture one or more images of the environment external to the smart device based upon the analysis of the sensing signals.

The set of image capture devices can include a single wide angle or very wide angle camera unit; or a plurality of image capture devices, each image capture device within the plurality of image capture devices having a field of view (FoV) that is distinguishable from the FoV of each other image capture device within the plurality of image capture devices, and which partially overlaps with the FoV of another image capture device within the plurality of image capture devices. The FoV of each image capture device within the plurality of image capture devices overlaps with the FoV of another image capture device within the plurality of image capture devices by less than 30%. The plurality of image capture devices can include at least one wide angle or very wide angle camera unit, for instance, at least two wide angle or very wide angle camera units. The plurality of image capture devices can additionally or alternatively include an x-axis camera configured for capturing images along the smart device x-axis; a y-axis camera configured for capturing images along the smart device y-axis; and a z-axis camera configured for capturing images along the smart device z-axis.

The set of sensors typically includes at least a heart rate sensor, plus a set of accelerometers and/or a set of gyroscopes. The set of sensors can additionally include a set of geolocation or geospatial coordinate sensors, a distance and/or proximity sensor (e.g., a radar-based distance and/or proximity sensor), a magnetometer, a gesture sensor, a pressure or compression sensor, a temperature sensor, an electrical continuity, conductivity, or conductance sensor, a moisture sensor, and/or a biometric sensor.

The smart device can include a cellular modem coupled to the set of processing units; and an antenna coupled to the cellular modem, wherein the memory further stores program instructions including: (a) a second set of program instructions that when executed selectively communicates sensed signals and temporally associated image data captured by the set of image capture devices or formed as a composite image therefrom to a server by way of a data communication network; (b) a third set of program instructions that when executed digitally stitches together individual images captured by individual image capture devices within the plurality of image capture devices to form a composite image; and/or (c) a fourth set of program instructions that when executed selectively processes sensed signals and in association with processing temporally associated image data corresponding to (i) one or more individual images captured by the set of image capture devices, or (ii) a composite image generated from multiple individual images captured by the set of image capture devices to estimate whether the smart device user requires assistance.

In accordance with an aspect of the present disclosure, a smart device (e.g., smartwatch) that is portable or wearable by a smart device user includes: a processing unit; a sensing/monitoring subsystem coupled to the processing unit, the sensing/monitoring subsystem including a first set of sensors configured for acquiring or generating sensed signals corresponding to at least one physiologic parameter of the smart device user and a second set of sensors including at least one of an accelerometer, a gyroscope, and a geospatial coordinate sensor; an imaging subsystem coupled to the processing unit, the imaging subsystem including a set of image capture devices for capturing images of an environment external to the smart device; a communication subsystem coupled to the processing unit, the communication subsystem including a cellular modem coupled to a Subscriber Identity/Identification Module (SIM) card interface and an antenna; and a main memory coupled to the processing unit and storing program instructions executable thereby, including: a first set of program instructions that when executed causes the smart device to acquire or generate sensed signals using the first set of sensors and the second set of sensors; a second set of program instructions that when executed causes the smart device to capture at least one image using the set of image capture devices and generate image data corresponding to the at least one image; a third set of program instructions that when executed wirelessly communicates sensed signals and image data to an electronic or computing destination remote from or external to the smart device; a fourth set of program instructions that when executed processes sensed signals acquired or generated by the first set of sensors and the second set of sensors in association with processing temporally associated image data generated by the set of cameras to determine a likelihood that the smart user is experiencing an atypical or emergency situation or requires assistance; and a fifth set of program instructions that when executed provides the smart device with mobile telephone functionality including making and receiving mobile telephone calls, and sending and receiving Simple Message Service (SMS) and/or Multimedia Message Service (MMS) messages.

In accordance with an aspect of the present disclosure, a system for monitoring and/or analyzing physical states, positions, activities, and/or surroundings corresponding to a plurality of smart device users includes: a set of smart devices, each smart device portable or wearable by a corresponding smart device user, each smart device having: a first processing unit; a first set of sensors coupled to the first processing unit, the first set of sensors configured for acquiring or generating sensed signals corresponding to at least one physiologic parameter of the smart device user; a second set of sensors coupled to the first processing unit, the second set of sensors including at least one of an accelerometer, a gyroscope, and a geospatial coordinate sensor; a set of image capture devices coupled to the first processing unit, the set of image capture devices configured for capturing one or more images of an environment external to the smart device and generating image data corresponding to each captured image; a wireless communication subsystem coupled to the first processing unit; and a memory storing program instructions that when executed by the first processing unit cause the communication subsystem to wirelessly transmit sensed signals and image data to an electronic or computing destination remote from or external to the smart device. The system further includes a set of servers configured for network communication with the set of smart devices, the set of servers having a second processing unit and a memory storing program instructions that when executed by the second processing unit analyze sensed signals and temporally associated image data received from each smart device to determine whether to issue an alert to a set of electronic or computing destinations associated with the smart device.

Each smart device can have a rechargeable power source, and the system can further include a charging/monitoring unit having: a charging unit configured for recharging a power source of a first smart device; and a set of sensors configured for measuring a distance between the charging/monitoring unit and a portion of the body of a first smart device user corresponding to the first smart device while the charging unit recharges the power source of the first smart device. The charging/monitoring unit can include a third processing unit and a memory storing a set of smart device user monitoring program instructions that when executed by the third processing unit determine whether a measured distance between the charging/monitoring unit and the first smart device user's body exceeds a threshold distance. When executed by the processing unit, the smart device user monitoring program instructions can further communicate with the first smart device or the set of servers in the event that the threshold distance has been exceeded.

The system can additionally or alternatively include at least three wireless communication nodes disposed in a controlled environment in which the set of smart devices resides, wherein each wireless communication node is configured for wireless communication with each smart device and communication with the set of servers, wherein the memory of each smart device further includes program instructions configured for outputting smart device presence packets receivable by the at least three wireless communication nodes and processable by the set of servers to calculate or triangulate a current position of the smart device. The set of servers can be configured for issuing an alert to a target electronic or computing destination in the event that a difference between a calculated or triangulated position of a smart device within the controlled environment and an initial calculated or triangulated position of the smart device within the controlled environment exceeds a threshold distance.

In accordance with an aspect of the present disclosure, a process for monitoring and/or analyzing physical states, positions, activities, and/or surroundings corresponding to a set of smart device users includes: providing a set of smart devices, each smart device portable or wearable by a corresponding smart device user, each smart device including: a processing unit; a first set of sensors coupled to the processing unit, the first set of sensors configured for acquiring or generating sensed signals corresponding to at least one physiologic parameter of the smart device user; a second set of sensors coupled to the processing unit, the second set of sensors including at least one of an accelerometer, a gyroscope, and a geospatial coordinate sensor; a set of image capture devices coupled to the processing unit, the set of image capture devices configured for capturing one or more images of an environment external to the smart device and generating image data corresponding to each captured image; a wireless communication subsystem coupled to the processing unit; and a memory storing program instructions that when executed by the processing unit cause the communication subsystem to wirelessly transmit sensed signals and image data to an electronic or computing destination remote from or external to the smart device. The process further includes providing a set of servers configured for network communication with each smart device, the set of servers having a processing unit and a memory storing program instructions that when executed by the processing unit enable wireless communication with each smart device; using the first set of sensors of each smart device to acquire or generate a first set of sensed signals corresponding to at least one physiologic state of the smart device user corresponding to the smart device; using the second set of sensors of each smart device to acquire a second set of sensed signals including at least one of accelerometer signals, gyroscope signals, and geospatial coordinates corresponding to the smart device; using the set of image capture devices of each smart device to capture a set of images an environment external to the smart device and generate corresponding image data; and processing at least one of the first sensed signals and the second sensed signals generated or acquired by each smart device in association with processing the image data generated by the smart device to automatically determine whether the smart device user corresponding to the smart device is experiencing an atypical or emergency situation or requires assistance.

The process can also include using each smart device to process the first sensed signals and second sensed signals acquired or generated thereby to determine a likelihood of whether an atypical or emergency condition corresponding to the smart device or the smart device user likely exists, wherein capturing images and generating corresponding image data representing portions of an environment external to the smart device is selectively performed based on whether an atypical or emergency condition corresponding to the smart device or the smart device user likely exists.

Using each smart device to capture the set of images representing portions of an environment external to the smart device can include: (a) capturing at least one image using a single wide angle camera unit, or (b) capturing a plurality of images using a plurality of cameras and/or wide angle camera units in which each camera or wide angle camera unit has a field of view (FoV) that is distinguishable from the FoV of each other camera or wide angle camera unit, and which partially overlaps with the FoV of another camera or wide angle camera unit. The FoV of each camera or wide angle camera unit within the plurality of cameras and/or wide angle camera units can overlap with the FoV of another camera or wide angle camera unit within the plurality of cameras and/or wide angle camera units by less than 30%. Each image within the plurality of images is captured simultaneously, essentially simultaneously, or in rapid succession with respect to each other image within the plurality of images.

The process can further include digitally stitching together image data corresponding to individual images within the plurality of images to generate image data of a single or unified composite image. Processing at least one of the first set of sensed signals and the second set of sensed signals in association with processing the image data can include analyzing at least one of the first set of sensed signals and the second set of sensed signals, plus analyzing the image data of the composite image.

Each smart device can include a rechargeable power source, wherein the process can further include: providing a charging/monitoring unit corresponding to at least a first smart device, the charging/monitoring unit having: a charging unit configured for recharging the power source of a first smart device; and a set of sensors configured for measuring a distance between the charging/monitoring unit and a portion of the body of a first smart device user corresponding to the first smart device. The process can additionally include measuring a set of distances between the charging/monitoring unit and the portion of the body of the first smart device user while the charging unit recharges the power source of the first smart device; and determining whether a distance between the charging/monitoring unit and the portion of the body of the first smart device user exceeds a threshold distance. The process can also include issuing an alert to a target electronic or computing destination in the event that the threshold distance is exceeded.

Additionally or alternatively, the process can include disposing at least three wireless communication nodes at known positions in a controlled environment in which the set of smart devices resides, wherein each wireless communication node is configured for wireless communication with each smart device and communication with the set of servers; outputting smart device presence packets from each smart device; receiving a first set of smart device presence packets output by a first smart device at a minimum of three wireless communication nodes; and processing the first set of smart device presence packets to calculate or triangulate a current position of the first smart device within the controlled environment. The process can also include determining whether a difference between calculated or triangulated position of the first smart device within the controlled environment and an initial calculated or triangulated position of the first smart device within the controlled environment exceeds a threshold distance; and issuing an alert to a target electronic or computing destination in the event that the threshold distance has been exceeded.

BRIEF DESCRIPTION OF THE DRAWINGS

FIGS. 5A-5H are illustrations showing aspects of representative smartwatch GUIs providable/provided by a smartwatch PWSD such as that illustrated in FIGS. 4A-4E in accordance with an embodiment of the present disclosure.

FIG. 7B illustrates a PWSD assistive apparatus in accordance with an embodiment of the present disclosure, which includes or is a multi-PWSD monitoring/tracking apparatus configured for monitoring/tracking the presence and/or locations/positions of multiple PWSDs within a given environment in parallel or on a concurrent/simultaneous basis.

FIGS. 10B-10D respectively illustrate a representative image captured along a PWSD x-axis, a representative image captured along a PWSD y-axis, and a representative image captured along a PWSD z-axis, and which collectively form an (x, y, z) image triplet in accordance with an embodiment of the present disclosure.

FIG. 10E illustrates a representative composite image generated from the (x, y, z) image triplet of FIGS. 10B-10D in accordance with an embodiment of the present disclosure.

DETAILED DESCRIPTION

Figure 1:
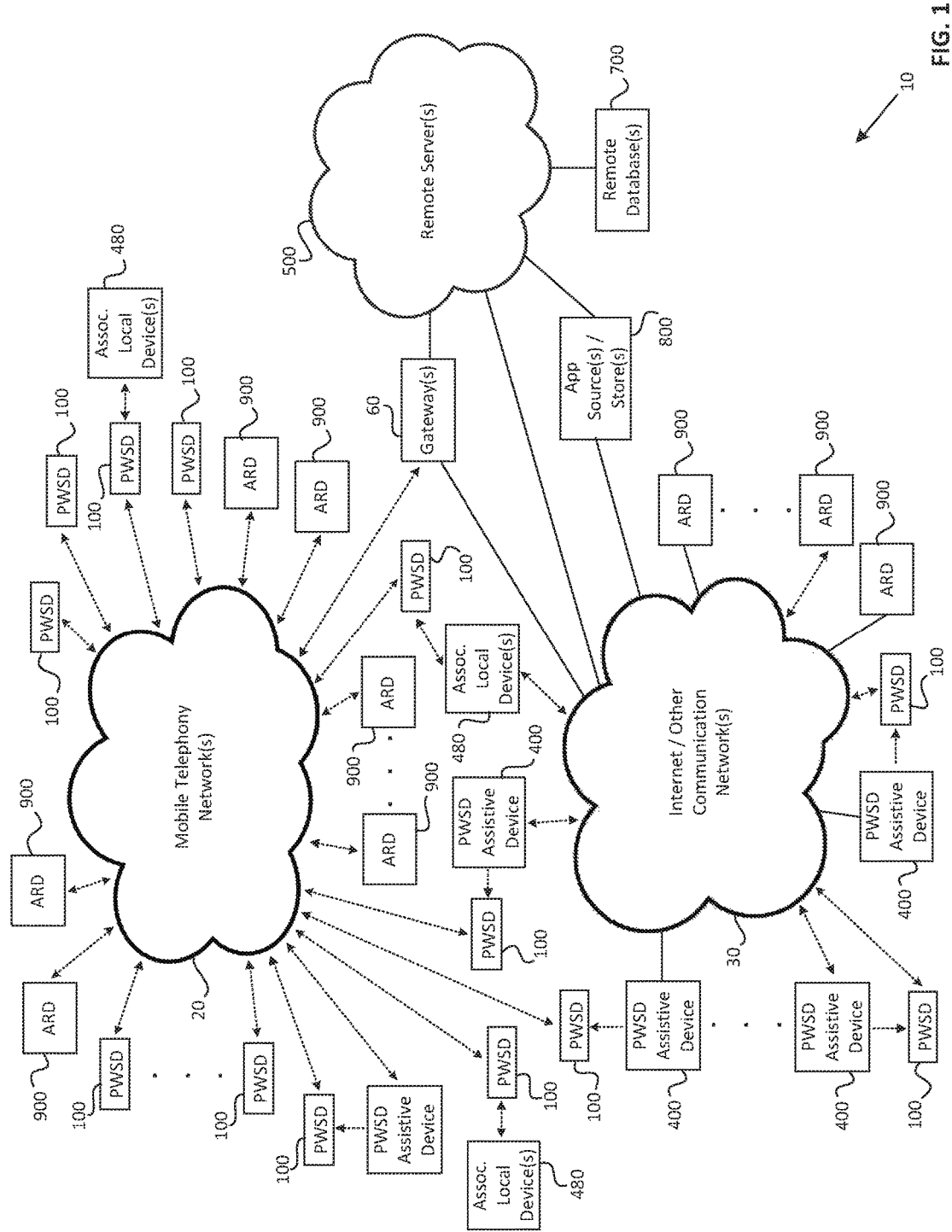
FIG. 1 is a schematic illustration of a representative system for analyzing, estimating, monitoring, categorizing/classifying, identifying, and/or determining portable/wearable smart device (PWSD) user physical/physiological state(s), behavior(s), and/or environmental surroundings or PWSD user orientation(s) therein by way of PWSDs that can capture images along orthogonal or approximately orthogonal x, y, and/or z spatial axes of PWSDs in accordance with an embodiment of the present disclosure.

In the present disclosure, the depiction of a given element or consideration or use of a particular element number in a particular FIG. or a reference thereto in corresponding descriptive material can encompass the same, an equivalent, a counterpart, or an analogous element or element number identified in another FIG. or descriptive material associated therewith. The use of "/" in a FIG. or text herein is understood to mean "and/or" unless otherwise indicated. The recitation of a particular numerical value or value range herein is understood to include or be a recitation of an approximate numerical value or value range. Furthermore, the use of the terms approximate, approximately, and about can mean within +/−20%, +/10%, +/−5%, or +/−0%.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). Furthermore, in the context of the present disclosure, a subset includes at least one element. In general, an element of a set or subset can include or be a system, an apparatus, a device, a structure, an object, a process, a physical parameter, or a value depending upon the type of set under consideration.

Herein, a "smart" device is a device that is associated/associatable with a user thereof, and which includes and/or is configured/configurable for communication with electronic/computing resources by which signals and/or information indicative of one or more user states, activities, physical surroundings, and/or physical orientations can be automatically or semi-automatically sensed, captured, generated, stored, monitored, evaluated, categorized/classified, determined, and/or communicated to particular electronic/computing destinations. Electronic/computing resources can include hardware and/or software, for instance, one or more sets of: signal sensing/acquisition devices; signal and/or information processing elements/devices: signal and/or information storage elements (e.g., memories, data storage units, and/or databases); signal and/or information communication devices; signal and/or information communication networks; input/output elements/devices; and program instruction sets/firmware/software associated therewith. As used in association with the description of particular embodiments in accordance with the present disclosure, the term "typically" means in multiple embodiments, and the term "possibly" means in at least one embodiment.

Overview

Embodiments in accordance with the present disclosure are generally directed to automated and/or semi-automated systems and processes/procedures in which a set of portable/wearable smart devices and/or objects, for instance, smartwatches, smart clothing accessories (e.g., a smart bracelet or smart belt buckle), and/or other types of smart portable/wearable devices (e.g., smart armbands; smart hearing/listening devices such as headphones: smart helmets; or smart ambulation assistance devices such as smart walkers or walking sticks/canes) can capture/generate and communicate various types of sensed information, signals, or data as well as one or more types of visual or image information, signals, or data to one or more other electronic/computing devices such as a set of remote servers (e.g., cloud based servers), which can (a) process/analyze captured or sensed information, signals, or data and associated image information, signals, or data received from each portable/wearable smart device/object to estimate, categorize, identify, or determine a current or most-recent physical state, behavior, environment, and/or environmental orientation of a user, wearer, or subject (e.g., a living human user or animal subject) corresponding to the portable/wearable smart device/object; and (b) selectively issue messages, notifications, or alerts (e.g., health condition, non-responsiveness, accident, or emergency alerts) to one or more target electronic/computing destinations corresponding to target individuals or organizations having an interest (e.g., a personal and/or economic interest) in the user's current or most-recent physical state, behavior, and/or environment or orientation therein, e.g., if such user state, behavior, environment, or environmental orientation likely indicates or indicates that the user is experiencing an emergency situation or requires urgent assistance.

Depending upon embodiment details, a message/notification/alert can include or be one or more of a simple messaging service (SMS)/multimedia messaging service (MMS) message; a pager message; an e-mail message; an audio/voice message or clip; a set of images or a video clip; or a social media posting. In various embodiments, an electronic/computing destination to which a given type of alert is issuable/issued can include or be a mobile telephone number, a pager number, a landline telephone number, an e-mail address, a communication network or Internet Protocol (IP) address, or a social media account, as further elaborated upon below.

For purpose of brevity and clarity in various portions of the description that follows, a portable/wearable smart device/object is referred to as a PWSD (portable/wearable smart device); a PWSD user, wearer, or subject is simply referred to as a user or PWSD user; sensed information, signals, or data is referred to as sensed signals or sensor signals; captured visual or image information, signals, or data is referred to as image data; a set of remote electronic/computing devices with which each PWSD communicates sensed signals and/or image data for processing/evaluation/analysis can be referred to as a set of remote servers; messages/notifications/alerts are simply referred to as alerts; and individuals or organizations to whom alerts are directed/issued can be referred to as target alert recipients. Additionally, PWSD users and the target alert recipients associated therewith can collectively be referred to as alert service participants or participants.

Each PWSD includes a set of processing resources (e.g., one or more processing units, such as a main/central processing unit (CPU), and possibly one or more graphics processing units (GPUs)) configured for executing stored program instruction sets (e.g., which can include built-in and/or upgradeable/downloadable program instruction sets, such as firmware and mobile application programs/apps). Additionally, each PWSD is coupled/couplable to or carries a display device such as a flat/flexible screen display, which can be touch sensitive, by which the PWSD can present visual information to its user; and a set of user input elements that typically includes a number of user selectable buttons or keys, and which can include the display device. In association with the execution of program instruction sets by the PWSD processing unit(s), the display device and the set of user input elements provide the PWSD with a user interface (UI) by which the PWSD user can interact with the PWSD (e.g., for selecting/activating, configuring, deactivating, or cancelling particular PWSD capabilities or functions). In various embodiments, the user interface includes a visual or graphical user interface (GUI) that is responsive to user input directed to the display device, in a manner readily understood by individuals having ordinary skill in the relevant art.

Each PWSD is coupled to or carries a set of image capture devices such as one or more digital camera units, cameras, image capture devices, or image sensors (which can be referred to hereafter as cameras for purpose of brevity) configured for capturing visual information such as images, image sequences, and/or video clips (hereafter images for purpose of brevity) relative to or along one or more PWSD spatial axes, for instance, relative to or along at least one of an x, y, and/or z spatial PWSD axis. The set of image capture devices is configured for capturing images in directions away from PWSD surfaces that normally interface with or rest against the PWSD user's body when the PWSD is carried or worn in a typical manner (e.g., in outward directions, away from those portions of the PWSD user's body toward or on which PWSD surfaces are positioned).

Each PWSD image capture device is configured for generating image data corresponding to or representing a particular view relative to or along a particular PWSD spatial axis. The image data corresponding to any given camera provides at least a two dimensional (2D) view of an environment external to the PWSD relative to along a particular PWSD axis or axial direction at a given time. In certain embodiments, a PWSD includes at least one camera (e.g., a camera such as that described in US Patent Publication No. 2014/0192238) configured for capturing or encoding depth related/depth information along a third dimension. Thus, the image data captured by such a camera (e.g., image data captured relative to or along a PWSD x-axis, y-axis, and/or z-axis) includes or encodes depth information.

Depending upon embodiment details, a PWSD can carry one, two, three, or more cameras. More particularly, in various embodiments each PWSD carries a set of cameras configured for capturing images relative to or along x, y, and/or z spatial axes of the PWSD (hereafter (x, y, z) spatial axes or (x, y, z) axes for purpose of brevity), where such axes are orthogonal, essentially orthogonal, or approximately orthogonal to each other, and can be defined as parallel to or extending through certain portions, segments, sides, or faces of the PWSD. Such (x, y, z) spatial axes correspond to orthogonal (x, y, z) spatial axes of the three dimensional (3D) spatial environment or surroundings of the PWSD and the orientation of the PWSD's user therein.

In some embodiments, a PWSD includes a single camera having a wide or very wide field of view (FoV) provided by a wide or very wide angle lens, where an image capture or optical axis of the wide or very wide angle lens, and hence of the single camera itself, is oriented or orientable along a particular direction with respect to a given spatial axis of the PWSD. An image captured by a single PWSD camera at a particular time, and which provides a view into particular portions or regions of the PWSD's 3D environment, can be referred to as an image singlet, which is digitally represented or storable as an image singlet dataset. In other embodiments, a PWSD includes two cameras (e.g., a pair of cameras instead of a single camera or three or more cameras), each of which can have a wide or very wide FOV provided by a wide or very wide angle lens, where each camera has an image capture or optical axis that is oriented or orientable along a particular direction relative to a distinct spatial axis of the PWSD. A set of two spatially and temporally associated or linked images captured by two PWSD cameras can be referred to as an image doublet, which is digitally represented or storable as an image doublet dataset. In alternate embodiments, a PWSD includes three or more cameras, where three cameras have image capture or optical axes oriented or orientable along particular spatial directions relative to distinct or distinguishable PWSD spatial axes. A set of three spatially and temporally associated or linked images captured by three PWSD cameras can be referred to as an image triplet, which is digitally represented or storage as an image triplet dataset.

In PWSD embodiments having a single camera, the single camera is configured such that its FoV encompasses a significant or very significant portion of the PWSD's 3D environment (i.e., the spatial environment external to the PWSD, in which the PWSD and the PWSD's user reside). In PWSD embodiments having multiple cameras, the cameras can be configured such that any given camera's FoV at least slightly overlaps with another camera's FoV (e.g, by approximately 40-50% or less, 30% or less, 20% or less, 15% or less, 10% or less, 5% or less, or 2% or less). As a result, portions of individual images captured by one camera overlap with portions of individual images captured by another camera, which facilitates the generation of composed or composite images which provide visually contiguous or continuous views of portions of the PWSD user's 3D spatial surroundings, as further detailed below. A composed/ composite image can be defined as a unified or single image that has been generated by way of digitally registering, aligning, joining, and/or stitching together portions of multiple individual images that were captured relative to or along distinct PWSD axes by the PWSD's set of cameras. In several embodiments, a PWSD's processing resources and/or the remote server(s) are configured for digitally aligning, joining, or stitching together individual images that are spatial and temporal counterparts with respect to each other to form a corresponding composed/composite image. A composite image dataset includes or is an image dataset or collection of image data that represents or is renderable as the composite image (e.g., the unified or single image that results from digitally registering, aligning, joining, or stitching together individual images captured by the PWSD's set of cameras), in a manner readily understood by individuals having ordinary skill in the relevant art. Stated equivalently, a composite image dataset can be defined as a dataset (e.g., a set or collection of binary values) that digitally represents or defines a composite image; or a dataset (e.g., a set or collection of binary values) which when rendered or output on a display device results in the generation or presentation of the composite image to an individual viewing the display device.

In view of the foregoing, in a multi-camera PWSD embodiment a composite image can be defined as an image formed from multiple temporally associated or linked individual images that were captured (e.g., by multiple distinct or distinguishable PWSD cameras) relative to or along multiple distinct or distinguishable PWSD axes. For purpose of simplicity and brevity, in a single-camera PWSD embodiment a composite image can be defined as a single image formed from or captured by the PWSD's single camera at a given time, with respect to the particular PWSD spatial axis relative to which the single camera's image capture or optical axis is oriented or aligned. A composite image can additionally or alternatively be defined as an evaluation image. An evaluation image dataset can be processed, analyzed, or evaluated by a PWSD or the set of remote servers to facilitate the determination of a current PWSD and/or PWSD user state and/or orientation.

For purpose of simplicity and to aid understanding, particular non-limiting representative PWSD embodiments described herein include three cameras, where each camera has its image capture or optical axis oriented along a predetermined x, y, or z PWSD axis. In such embodiments, any given camera can be configured for capturing images (e.g., 2D images) along a corresponding x, y, or z PWSD axis, where such images respectively contain portions of or provide x, y, and/or z axis views of corresponding to the PWSD's 3D spatial surroundings. Thus, in accordance with such a non-limiting representative embodiment, a PWSD can include at least a first camera having an image capture or optical axis aligned with an x-axis of the PWSD; at least a second camera having an image capture or optical axis aligned with a y-axis of the PWSD; and at least a third camera having an image capture or optical axis aligned with a z-axis of the PWSD. Such image capture devices are configured for generating (x, y, z) image data corresponding to (x, y, z) images captured along PWSD (x, y, z) spatial axes, respectively, in a manner readily understood by individuals having ordinary skill in the relevant art.

In accordance with such aforementioned non-limiting representative three camera PWSD embodiments, an (x, y, z) image triplet can be defined as an x-axis image, a y-axis image, and a z-axis image corresponding to or captured along a given PWSD's x-axis, y-axis, and z-axis, respectively, where the individual images within the (x, y, z) image triplet (a) are captured simultaneously, effectively/essentially simultaneously, nearly simultaneously, or at very brief or short intervals relative to each other (e.g., within milliseconds, less than 1 second, or a few seconds of each other), and (b) correspond to or represent a simultaneous, effectively/essentially instantaneous, nearly instantaneous, very brief, or brief time window view of a 3D external environment in which the PWSD and its user reside, and the orientation of the PWSD and/or its user therein, at a given time. An, (x, y, z,) image triplet dataset or (x, y, z) image triplet data can be defined as (x, y, z) image data that corresponds to or represents the (x, y, z) images of an (x, y, z) image triplet, and which includes x-axis image data, y-axis image data, and z-axis image data respectively corresponding to the PWSD's x-axis, y-axis, and z-axis. Correspondingly, a composed/composite image in such embodiments includes the individual images (e.g., corresponding to visually overlapping regions) of at least one (x, y, z) image triplet.

A composite or evaluation image embodies a simultaneous, effectively/essentially instantaneous, nearly instantaneous, very brief, or brief time window view established by individual images from which the composite image was formed. The composite image represents or is expected to represent a unified or single view of portions of the current or most-recent 3D spatial environment of the PWSD and the orientation of the PWSD and/or its user relative to or within this 3D environment with respect to a particular time or very brief/brief time interval. Stated equivalently, the composite image is indicative of, corresponds to, represents, or is expected to represent a unified or single view of portions (e.g., significant portions) of the PWSD user's current or most-recent 3D environment and their orientation therein. Thus, for a composite image generated from at least one (x, y, z) image triplet, the composite image embodies the simultaneous, effectively/essentially instantaneous, nearly instantaneous, very brief, or brief time window view established by the (x, y, z) image triplet(s) from which the composite image was formed, and provides a unified or single view of portions of the current or most-recent 3D spatial environment of the PWSD and the orientation of the PWSD and/or its user relative to or within this 3D environment with respect to a particular time or very brief/brief time interval. In various embodiments, at least some PWSDs can directly generate composite images/composite image datasets from captured images; additionally or alternatively, the set of remote servers can generate composite images from image datasets received from PWSDs.

As previously indicated, embodiments in accordance with the present disclosure are not limited to PWSDs having three cameras. Thus, in multiple embodiments a PWSD includes fewer than three cameras, for instance, a first camera having an image capture or optical axis aligned relative to or along the PWSD's x-axis; and a second camera having an image capture or optical axis aligned relative to or along the PWSD's y-axis or z-axis, depending upon embodiment details. Moreover, in certain embodiments a PWSD can include one or more cameras having an image capture or optical axis that can be selectively aligned relative to or along multiple PWSD axes (e.g., the PWSD's y-axis and z-axis) such as by way of a set of displaceable/movable/pivotable/rotatable electromechanical elements that carry a camera. Individuals having ordinary skill in the relevant art will also understand that PWSD embodiments that include three or more cameras can include one or more cameras having an image capture or optical axis that can be selectively aligned relative to or along two orthogonal PWSD axes, such as by way of a set of displaceable/movable/pivotable/rotatable electromechanical elements that carry a camera.

Each PWSD is configured for signal/data communication with and/or carries a set of sensors, sensing devices, sensing elements, measuring devices, or measuring elements configured for capturing, generating, or providing sensed/measured signals or data that can be temporally associated or linked with images captured by the PWSD's set of cameras (e.g., one or more image singlets, doublets, or triplets) and composite images generated therefrom. A PWSD's processing resources and/or the remote server(s) are configured for analyzing captured image data in association with analyzing sensed signals, information, or data.

The set of sensors can include, for instance, one or more of a geolocation sensor or receiver; a magnetometer (e.g., a 3D magnetometer); a motion sensor: an accelerometer (e.g., a 3D accelerometer); a gyroscope; a gesture sensor; a level sensor (e.g, an x, y, and/or z-axis level sensor); a set of distance and/or proximity sensors (e.g., an x, y, and/or z-axis distance/proximity sensor, such as a radar-based distance/proximity sensor, an ultrasonic distance/proximity sensor, and/or an optical distance/proximity sensor); a microphone; a number of pressure/compression/force sensors; a pulse/heart rate sensor; a temperature sensor, an electrical continuity, conductivity, or conductance sensor; a moisture sensor; and/or another type of sensor (e.g., configured for sensing biometric signals). In certain embodiments, at least some pressure/compression/force sensors are supported or carried by footwear (e.g., a pair of shoes, slippers, or sandals, or an insert such as an arch support therefor) worn by the PWSD user, and are configured to output foot pressure signals that are detectable by the PWSD, as further detailed below. Sensed signals can be indicative of or correspond to a current or most-recent physical state or physiologic/biological parameter of the PWSD user, and/or a physical state or orientation of the PWSD and/or its user. An individual having ordinary skill in the relevant art will understand that certain types of sensors, such as a gesture sensor or a microphone, can form portions of the PWSD's set of user input devices, and hence can support or provide particular types of PWSD user interface functionality.

Each PWSD additionally carries wireless communication circuitry, such that each PWSD can wirelessly communicate sensed signals as well as image datasets and composite image datasets to the set of remote servers and possibly additional electronic/computing devices. In various embodiments, the PWSD's wireless communication circuitry includes a wireless communication chipset providing cellular network/mobile telephony communication circuitry, such that communication between the PWSD and the set of remote servers can occur by way of a cellular/mobile telephony network. Depending upon embodiment details, a PWSD can additionally or alternatively include one or more other types of wireless communication circuitry (e.g., radio frequency (RF) communication circuitry configured for operating in accordance with a WiFi, Bluetooth®, or other RF signal communication protocol, and/or infrared (IR) communication circuitry configured for operating in accordance with an IR signal communication protocol) and/or wire-based communication circuitry (e.g., a Universal Serial Bus or other type of communication interface), such that the PWSD can communicate with external electronic/computing systems or devices in multiple manners.

Depending on embodiment and/or situational details, a PWSD can selectively communicate one or more image datasets (e.g., spatially and temporally associated or linked image datasets, such as (x, y, z) image triplet datasets), one or more composite image datasets, sensed signals, and/or possibly related or derived information (e.g., measured information, such as (x, y, z) axis distance measurements) to the set of remote servers (and possibly additional or alternate electronic/computing devices), on a periodic/regular basis and/or in response to particular events or conditions indicated by sensed signals, such as sensed signals falling outside of an expected/typical, normal/acceptable, or predetermined limit or range, and/or sensed signals exhibiting atypical, unusual, unexpected, or unstable values or value ranges, as further detailed below. For instance, a PWSD can communicate sensed signals and at least one composite image dataset and/or at least one corresponding multi-image dataset (e.g., an (x, y, z) image triplet dataset) to the set of remote servers if one or more sensed signals exceed, fall below, or fail to remain within expected/typical, normal, or allowable thresholds or levels (e.g., for more than a predetermined or programmably defined period of time). In several embodiments, a PWSD can also (a) capture a set of images, such as at least one (x, y, z) image triplet, in a manner temporally associated or linked with particular sensed signals, and possibly generate at least corresponding composite image; and (b) communicate sensed signals, at least one composite image dataset and/or at least one corresponding multi-image dataset (e.g., an (x, y, z) image triplet dataset), and possibly other information (e.g., sensed/measured information, such as (x, y, z) axis distance measurements) to the remote server(s) in response to detecting the generation of a particular set of PWSD user input element signals, for instance, one or more signals generated in response to user activation of a particular PWSD user input element or a particular sequence of such input elements (e.g., corresponding to or defined as an emergency/help/panic button or button sequence).

A PWSD can automatically capture sensed signals and/or images at particular times/time intervals (e.g., every k milliseconds, seconds, or minutes), such that the PWSD and/or the remote server(s) can process/analyze sensed signals and/or captured image content to monitor/estimate/determine the PWSD user's current physiologic state and/or their physical situation within their environmental surroundings. In various embodiments, sensed signals captured by a PWSD can be analyzed by the PWSD and/or the remote server(s) (e.g., independent or in the absence of the generation of one or more image datasets (e.g., one or more multi-image datasets or corresponding composite image datasets), for instance, every s milliseconds, seconds, or minutes (e.g., approximately every 0.5-30 seconds, or every 0.5-5 minutes); and based upon an analysis of sensed signals, the PWSD or the remote server(s) can determine whether to capture one or more additional images (e.g., (x, y, z) image triplets). Depending upon embodiment or situational details, sensed signals, one or more captured images, and/or one or more composite image datasets can be generated and analyzed on a specified, programmable/selectable/adjustable, or predetermined schedule, such as every i milliseconds, seconds, or minutes (for instance, approximately every 0.5-30 seconds (e.g., every 5-20 seconds), or approximately every 0.5-20 minutes, or every 5-10 minutes, (e.g., every 2-5 minutes), or in accordance with another time interval).

The set of remote servers and/or each PWSD is configured for automatically or semi-automatically processing/analyzing sensed signals, captured image datasets (e.g., multi-image datasets, such as (x, y, z) image triplet datasets), and/or composite images temporally linked with the sensed signals, possibly additional information such as (x, y, z) axis distance measurements, and possibly associated user input signals to estimate, categorize/classify, identify, or determine a current or most-recent physical/physiological state, condition, or behavior of the user of the PWSD under consideration, which in various embodiments includes an orientation of the user relative to or within their present environmental surroundings. For instance, a given PWSD and/or the set of remote servers can analyze received sensed signals that are indicative of or which measure particular aspects of the PWSD user's current, most-recent, or recent physical/physiologic state(s) to initially estimate or determine a likelihood that their physiologic state is currently normal or abnormal. Furthermore, in some embodiments the remote server(s) and/or the PWSD can be configured for automatically or semi-automatically determining user orientation and/or motion information, such as a likelihood of whether the user is upright or lying down (e.g., lying down facing upwards, downwards, or sideways, for instance, as a result of a fall), and possibly whether a portion of the user's body on which the PWSD is carried is or is likely moving, has recently been moving, is or is likely stationary, or has been stationary for a significant prolonged period of time (e.g., for approximately 1-2 minutes or longer), based on processing/analyzing sensed signals, associated image data, and possibly (x, y, z) axis distance measurements.

Depending upon such estimation or determination of the PWSD user's current, most-recent, or recent physical state(s), behavior(s), and/or orientation(s) within their surrounding environment, and possibly the PWSD user's most-recently tracked geospatial location(s), the set of remote servers can selectively issue one or more textual, audio, and/or visual alerts (e.g., one or more "user requires assistance," "user fallen," "user motionless," "user non-responsive," "user emergency," or "user accident" alerts, which can include geolocation information corresponding to the PWSD as well as user physical state/behavior/orientation/ location information) to one or more target electronic/ computing destinations corresponding to target alert recipients. More particularly, in various embodiments each target electronic/computing destination corresponds to a target individual or organization, such a family member, caretaker, emergency response service, security service, or law enforcement service that is associated or linked (e.g., by way of a database remote from the PWSD) with the PWSD user under consideration. For a PWSD given user, the target electronic/computing destination(s) to which alerts are to be issued can be defined in association with the execution of an application program (e.g., a mobile or desktop application) that is downloadable to and executable by an electronic/ computing device corresponding to a particular target alert recipient.

The availability of (a) one or more current or most-recent sets of sensed or measured signals, plus at least one (b) current or most-recent image dataset (e.g., a multi-image dataset such as an (x, y, z) image triplet dataset) and/or (c) composite image dataset temporally linked with the sensed/ measured signals, which provide a current or most-recent view into portions of the PWSD user's 3D environment and their orientation therein, can aid enhanced accuracy or accurate estimation/determination/identification of the PWSD user's current or most-recent physical state, behavior, physical environment, and/or physical orientation compared to such an estimation/determination/identification based upon sensed signals alone (e.g., conventional sensed signals), because each image dataset (e.g., multi-image dataset such as an (x, y, z) image triplet dataset) or composite image dataset encodes visual/image information that exceeds, is beyond, or which can facilitate or enable confirmation of the contextual scope of sensed/measured signals alone. Furthermore, in accordance with particular representative non-limiting embodiments of the present disclosure, each set of captured images (e.g., each (x, y, z) image triplet) or composite image encodes visual/image information that exceeds or is beyond the contextual scope of images captured along only one or two orthogonal PWSD axes (e.g., an x-axis image, without a counterpart y-axis and/or z-axis image; or x-axis and y-axis images, without a counterpart z-axis image). Consequently, the availability of current/most recent sensed/measured signals in addition to current/most-recent captured image datasets/composite image datasets in accordance with an embodiment of the present disclosure can reduce the likelihood that erroneous or false alerts are issued to the target electronic/computing destination(s) compared to the issuance of alerts based upon (a) sensed/ measured signals alone; and/or possibly (b) images captured along only one or two orthogonal PWSD spatial axes, depending upon PWSD image capture device capabilities or configuration (e.g., camera FoV relative to the PWSD's 3D spatial environment).

In some embodiments, a PWSD can present, output, or play one or more audio messages, or the set of remote servers can issue one or more audio message presentation commands to the PWSD, based upon an analysis of sensed signals and/or a set of composite images and the estimation or determination of the PWSD user's physical state/behavior/orientation therefrom, or following user input (e.g., user activation of an emergency/panic button). For instance, the PWSD can output or play an audible or audio assistance message, such as "help required—please assist me." The set of remote servers can additionally or alternatively issue additional or other commands to a PWSD under consideration based upon the user's current or most-recent physical state, behavior, and/or orientation.

In multiple embodiments, the set of remote servers is cloud based (e.g., existing as multiple/dynamically allocatable servers within a private or semi-private cloud), and can be configured for providing user monitoring/physical state/ physical environment/environmental orientation analysis and associated alert services to a set of target individuals and/or organizations associated with any given PWSD user in one or more manners. A set of remote databases is associated or linked with the set of remote servers, within which a history of composite image datasets, possibly related image datasets (e.g., individual captured image datasets or multi-image datasets, such as (x, y, z) image triplet datasets), sensed signals, alerts, target electronic/computing destinations for alerts, and other information (e.g., PWSD user health related information) can be stored for each PWSD user or particular subsets of PWSD users.

In addition or as an alternative to the foregoing, in some embodiments a PWSD, possibly in association with a PWSD assistive apparatus or device (e.g., a wireless PWSD charging device) and/or the set of remote servers, can determine whether an expected or intended physical location/position/orientation of the PWSD user within their spatial environment has changed from a first, initial, recommended, expected, intended, permitted, or required location/ position/orientation to a second, subsequent, non-recommended, unexpected, unintended, or unauthorized location/ position/orientation, for instance, from a prone/lying down position/orientation (e.g., in a bed of a health care facility such as a hospital) to an upright/standing position/orientation (e.g., next to or away from the bed). If so, the PWSD, the PWSD assistive apparatus or device, and/or the set of remote servers can issue a set of alerts to one or more target electronic/computing destinations associated with particular individuals or organizations having an interest in whether the PWSD user's physical location/position/orientation has changed relative to the user's recommended, expected, intended, permitted, or required location/position/orientation. A target electronic/computing destination in such a situation can include or be a mobile telephone number, a pager number, an IP address, or an e-mail address corresponding to a health care professional (e.g., a nurse) responsible for monitoring aspects of the PWSD user's physical state(s)/behavior(s).

Systems that include PWSDs can provide additional and/or other types of functionality, such as broader or more limited functionality, than the particular types of functionality described above, while remaining within the scope of the present disclosure. For instance, in several embodiments, a PWSD can process/analyze sensed signals and a set of images (e.g., (x, y, z) image triplets; or (x, y), (x, z), or (y, z) image doublets) or composite images separate from or independent of analogous or equivalent processing/analysis by the set of remote servers (e.g., in the event that the PWSD cannot maintain responsive/uninterrupted/consistent/reliable/robust wireless communication with the set of remote servers) to estimate or determine the PWSD user's current or most-recent physical state(s)/behavior(s)/orientation(s). Based upon such processing/analysis, the PWSD can issue one or more SMS/MMS message to the remote server(s) such that the remote server(s) can selectively communicate alerts to one or more target electronic/computing destinations. A PWSD's processing/analysis of sensed signals and captured image content (e.g., within one or more composite images) can occur in a manner that is essentially identical, analogous, or similar to the manner in which the set of remote servers can process/analyze such information. Additionally or alternatively, in a various embodiments PWSDs are configurable/configured for providing functionality that is analogous or which corresponds or is essentially identical to conventional mobile telephone/smartphone functionality, including making and receiving audio/video calls; sending and receiving SMS/MMS messages (e.g., PWSD user defined SMS/MMS messages); and possibly executing particular types of mobile/portable device apps, such as one or more social media apps by which posts can be sent to and received from corresponding social media services (e.g., WhatsApp, Line, Twitter, Weibo, Facebook, etc. . . . ). Representative aspects of systems, apparatuses, devices, and automated processes/procedures involving PWSDs in accordance with particular non-limiting representative embodiments of the present disclosure are provided in detail hereafter to further aid understanding.

Aspects of Representative System Embodiments

FIG. 1 is a schematic illustration of a representative system 10 for analyzing, estimating, monitoring, categorizing/classifying, identifying, and/or determining PWSD user physical/physiological state(s), behavior(s), and/or environmental surroundings or PWSD user orientation(s) therein by way of PWSDs 100 that can capture images along one or more orthogonal or approximately orthogonal x, y, and z PWSD spatial axes in accordance with an embodiment of the present disclosure. In an embodiment, the system 10 includes a plurality of PWSDs 100 that are movable, transportable/carryable/carried, or wearable/worn by corresponding PWSD users; a set of servers 500 separate/remote from the plurality of PWSDs 100, as well as at least one remote database 700 with which the remote server(s) 500 can communicate; and a plurality of alert reception systems/devices (ARDs) 900. The PWSDs 100 and ARDs 900 can be distributed (e.g., geographically distributed) within and/or across one or more localities, regions, territories, states, countries, and/or continents, in a manner readily understood by individuals having ordinary skill in the relevant art.

In several embodiments, the system 10 further includes a set of PWSD assistive apparatuses or devices 400. A PWSD assistive apparatus/device 400 is typically locally associated with a given PWSD 100, and can be configured for providing one or more types of PWSD support functions. Depending upon embodiment details, a PWSD assistive apparatus/device 400 can include or be a wireless PWSD recharging device; a PWSD user position/location/orientation monitoring or tracking device; or a set of footwear-based pressure sensors configured for wirelessly outputting or communicating foot pressure signals that can be detected by the PWSD 100 with which it is associated. A PWSD assistive apparatus/device 400 can be configured for communicating with a PWSD 100 and/or the set of remote servers 500 to facilitate or enable the identification or determination of particular types of PWSD user physical states, locations, positions, orientations, and/or behaviors and possibly changes thereto.

As set forth above, in various embodiments each PWSD 100 is configured for (a) acquiring, capturing, and/or generating sensed/measured signals; (b) capturing images (e.g., (x, y, z) images) and generating image datasets (e.g., (x, y, z) image triplet datasets) therefrom; (c) typically or possibly generating composite image datasets from captured image datasets (e.g., (x, y, z) image triplet datasets); and (d) communicating sensed/measured signals as well as image datasets (e.g., (x, y, z) image triplet datasets) and/or composite image datasets to the set of remote servers 500 by way of one or more communication networks, such as a cellular/mobile telephony network 20, the Internet 30, and/or another communication network (e.g., a Wide Area Network (WAN) or a Local Area Network (LAN), not shown). The set of remote servers 500 is configured for processing/analyzing (i) sensed/measured signals and associated image datasets (e.g., (x, y, z) image triplet datasets) and/or composite image datasets; and/or in certain embodiments (ii) information, signals, or data corresponding to or received from one or more PWSD assistive devices 400. Based upon such processing/analyzing, the set of remote servers 500 is further configured for communicating one or more alerts to a set of target electronic/computing destinations corresponding to target alert recipients, such as particular mobile telephone numbers, pager numbers, landline telephone numbers, e-mail addresses, social media accounts, and/or IP addresses.

For instance, based upon processing/analyzing current or most-recent sensed signals as well as one or more composite image datasets associated or temporally linked therewith, the remote server(s) 500 can determine that a PWSD user under consideration is likely experiencing a potentially dangerous or emergency situation. For instance, the set of remote servers 500 can determine that the PWSD user has experienced a fall from which the PWSD user is likely incapable of independently returning to a normal or safe physical orientation in the absence of assistance (e.g., urgent assistance) from one or more other individuals; and/or the PWSD user is experiencing an undesirable, abnormal, dangerous, or emergency health condition, for instance, an epileptic seizure or a cardiac condition such as an arrhythmia, myocardial infarction, or cardiac arrest. Following such determination, the remote server(s) 500 can issue one or more alerts to at least some of the target electronic/computing destinations associated or linked with the PWSD user in the remote database 700. In various embodiments, the remote server(s) 500 can also issue alerts to such target electronic/computing destinations in response to PWSD user input, as indicated by specific PWSD user interaction with the PWSD's user interface (e.g., one or more buttons and/or the GUI). Depending upon embodiment details, alerts can be issued to each target electronic/computing destination associated with a PWSD user under consideration, or alerts can be selectively issued to particular target electronic/computing destinations associated with the PWSD user in a prioritized or hierarchical sequence.

The remote database 700 is configured for storing PWSD device information; associated PWSD user information; a number of target electronic/computing destinations associated with each PWSD user (e.g., at least one target electronic/computing destination corresponding to a target alert recipient); and possibly or typically other information. For each PWSD 100, the PWSD device information stored in the remote database 700 includes a PWSD identifier (ID) that uniquely identifies the PWSD 100; a wireless network address (e.g., a mobile telephone number and/or an IP address) corresponding to the PWSD 100; and typically current PWSD configuration/capability information. In multiple embodiments, the PWSD user information stored in the remote database 700 includes a PWSD user name; PWSD user contact information (e.g., at least one e-mail address and/or mobile telephone number, and possibly a physical residence, mailing, or work address); a PWSD user birth date or age; a schedule and/or history of particular types of PWSD user activities in which the PWSD user is expected to engage or has recently engaged, corresponding to one or more time periods (e.g., an hourly, daily, weekly, or monthly time period); a history of sensed signals obtained from the PWSD's set of sensors; possibly a history of at least some composite image datasets and/or image singlet, doublet, or triplet datasets corresponding to one or more time periods (e.g., an hourly, daily, weekly, or monthly time period), which can be associated, linked, or correlated with the aforementioned activity schedule and/or history; in certain embodiments, a listing of or link to the PWSD user's medical history/condition(s) (e.g., whether the user has a heart condition, epilepsy, diabetes, particular drug allergies, etc. . . . ): and possibly other information corresponding to the PWSD user, such as PWSD user geolocation history information, geofencing information, calendar information (e.g., daily, weekly, and monthly calendar data), and/or a contacts list, as further described below. In some embodiments, the PWSD user information can include one or more e-mail and/or social media account IDs and associated passwords for the PWSD user, such that the PWSD 100 can automatically log into such accounts on behalf of the PWSD user. For instance, by way of automatically logging into one or more of the PWSD user's social media accounts (e.g., Whatsapp, Line, Twitter, Facebook, Weibo, etc. . . . accounts), the PWSD 100 can issue posts to such social media accounts in response to user input.

For a given PWSD user, the set of target electronic/computing destination(s) stored in the remote database 700 specify one or more mobile telephone numbers, landline telephone numbers, pager numbers, e-mail addresses, Internet Protocol (IP) addresses, and/or possibly social media account IDs corresponding to target alert recipients to which the remote server(s) 500 can issue alerts based upon processing/analyzing sensed signals and image datasets received from this user's PWSD 100. The remote database 700 can also store corresponding target alert recipient details, such as target alert recipient IDs, physical addresses, and PWSD user relationship information (e.g., to identify a given target alert recipient as a spouse, family member, co-worker, friend, caretaker, third party aid/assistance service employee, etc. . . . ).

As part of processing/analyzing a set of most-recent sensed/measured signals and/or image datasets or composite images corresponding to a given PWSD 100, the remote server(s) 500 can utilize the PWSD user's activity schedule/history, sensed/measured signal history, composite image history, and/or medical history to further aid accurate estimation/determination/identification of the PWSD user's current or most-recent physical state, behavior, physical environment, and/or physical orientation, to thereby aid enhanced accuracy determination of whether to issue one or more alerts to the target electronic/computing destination(s) linked with the PWSD user in the remote database 700, and thus reduce the likelihood of issuing erroneous or false alerts. The remote server(s) 500 can also issue alert cancellations to a set of target electronic/computing destinations to which alerts had been previously issued in the event that sensed signals, composite images, and/or PWSD user input indicate that the PWSD user has returned to an expected/normal/safe physical state and orientation.

As indicated above, PWSDs 100 can themselves be configured for processing/analyzing sensed/measured signals and possibly generating and processing captured image datasets (e.g., singlet datasets, image doublet datasets, or image triplet datasets depending upon embodiment details) and/or composite image datasets, and can be configured for selectively issuing one or more SMS/MMS messages to the remote server(s) 500, where such messages request the communication of alerts to at least some target electronic/computing destinations associated with the PWSD user based upon such processing/analysis. A PWSD 100 can selectively generate and process one or more captured image datasets (e.g., image singlet datasets, image doublet datasets, or image triplet datasets) and/or composite image datasets in association with processing sensed/measured signals as a secondary process or backup measure in the event that wireless communication (e.g., responsive/uninterrupted/reliable/robust wireless communication) between the PWSD 100 and the set of remote servers 500 cannot be reliably established or consistently maintained. In such embodiments, one or more PWSDs 100 can include an internal or on-board database in which at least some target electronic/computing destinations associated with the PWSD user reside, and possibly in which a limited PWSD user activity schedule/history, a limited PWSD user medical history, a limited sensed/measured signal history, and/or a limited captured image/composite image history reside, which processing resources within the PWSD 100 can access and analyze to aid enhanced accuracy determination of the PWSD user's current or most-recent physical state, behavior, physical environment, and/or physical orientation, and enhanced accuracy determination of whether to issue one or more SMS/MMS messages to the remote server(s) requesting the issuance of alerts to target alert recipients associated with the PWSD user. The PWSD's internal database can correspond to or include a portion of the information corresponding to the PWSD user in the remote database 700.

Communication directed to target electronic/computing destinations can involve one or more communication networks, such as a cellular/mobile telephony network 20, the Internet 30, and/or another communication network. The system 10 can include a set of gateways 60, such as an SMS gateway and a Voice over Internet Protocol (VoIP) gateway coupled to the remote server(s) 500, which can also be cloud based, to facilitate or enable such communication, in a manner readily understood by individuals having ordinary skill in the relevant art.

Each ARD 900 includes or is an electronic/computing system or device configured for receiving, retrieving, accessing, presenting, and/or forwarding alerts corresponding to at least one PWSD user. Thus, an ARD 900 can include or be a system or device capable of receiving alerts by way of a cellular/mobile telephony network 20, the Internet 30, and/or another communication network, and can be, for instance, a smartphone, a tablet computer, a phablet, a laptop computer, a desktop computer, an organizational network server, or other type of electronic/computing device, apparatus, or system (e.g., a set top box/home entertainment system/electronic gaming system having Internet connectivity; or a smartwatch, which can be a PWSD 100 associated with another PWSD user). Depending upon an ARD 900 under consideration and/or embodiment or situational details, a given ARD 900 can be used by or associated with (a) one or more individuals other than a PWSD user, such as the PWSD user's family member(s), caretaker(s), friend(s), or possibly coworker(s); or (b) an organization, for instance, an emergency response service such as an ambulance service, a private security service, or a law enforcement service, or possibly the PWSD user's employer.

In certain embodiments, at least some PWSDs 100 are also configured/configurable for communicating with one or more associated or adjunctive local electronic/computing devices 480. Such communication can involve the transfer of sensed signals, image datasets, composite image datasets, and/or user input signals from a PWSD 100 to a local device 480 associated therewith by way of wireless communication (e.g., WiFi, Bluetooth®, or infrared signal transfer) or wire-based communication (e.g., USB signal transfer). An associated local device 480 can include or be, for instance, a portable device such as a smartphone, a tablet computer, a phablet, a laptop computer, an external data storage device, or other device configured/configurable for operating in association with or supporting particular types of PWSD functionality, for instance, storage of PWSD information, signals, or data in a local database external to the PWSD 100.

The system 10 can also include a set of application sources/stores 800 from which particular types of apps (e.g., mobile and/or non-mobile/desktop apps) can be transferred or downloaded to PWSDs 100, associated local devices 480, and/or ARDs 900. Such apps include program instructions that, when executed by a set of processing units, facilitate or enable system registration procedures by which system services providable to PWSD users and target alert recipients are activated and configured/configurable.

Aspects of Representative PWSD Embodiments

Figure 2:
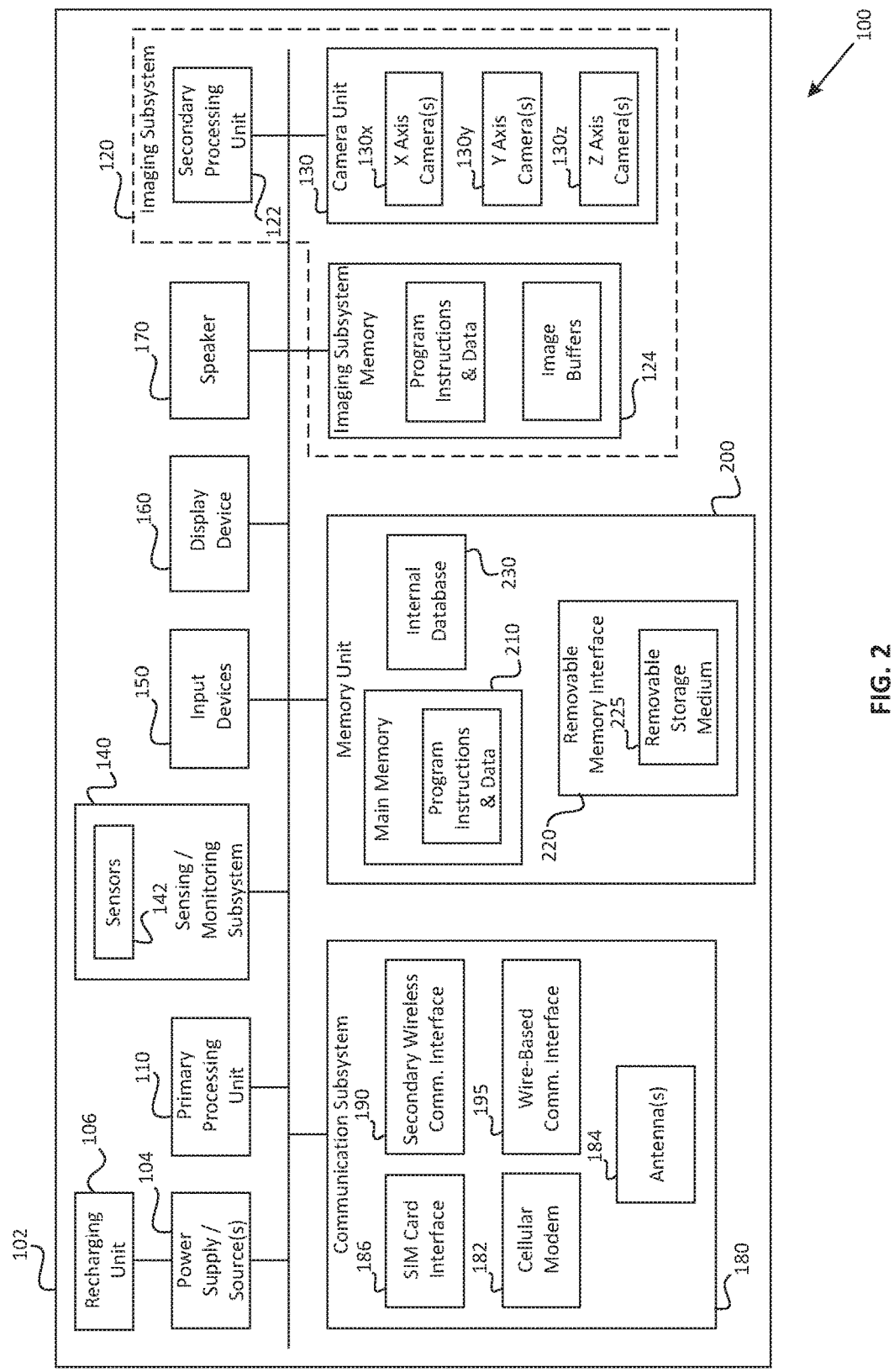
FIG. 2 is a block diagram of a representative PWSD in accordance with an embodiment of the present disclosure.

FIG. 2 is a block diagram of a representative PWSD 100 in accordance with an embodiment of the present disclosure. In an embodiment, the PWSD 100 includes a portable structure, body, housing, or case 102 that can be carried or worn by a PWSD user, and which carries electrical devices and associated circuitry by which PWSD functionality and particular system functionality is implemented. In various embodiments, the PWSD's electrical devices/circuitry includes a power source or battery 104; a battery recharging interface/unit 106; a set of primary processing units 110 such as a set of processing cores or a CPU: an imaging subsystem 120 including at least one secondary processing unit 122 such as a GPU, an imaging subsystem memory 124 (e.g., which includes a set of image buffers), and a camera unit or set of cameras 130 configured for capturing images of the PWSD's external environment; a sensing/monitoring subsystem 140 including a set of sensors 142; a set of user input devices 150; a display device 160; a speaker 170; a communication subsystem 180 that supports one or more types of wireless communication and possibly or typically one or more types of wire-based communication; and a memory unit 200. The PWSD's electrical devices/circuitry can be coupled together by way of one or more signal/data communication lines, pathways, or buses, in a manner readily understood by an individual having ordinary skill in the relevant art.

The battery 104 can include or be a set of rechargeable electrical charge storage devices, in a manner also readily understood by an individual having ordinary skill in the relevant art. Depending upon embodiment details, the recharging interface/unit 106 can be couplable/coupled to or include one or more types of electrical charge transfer or generation interfaces/devices, such as a wire coil that can recharge the battery by way of magnetic induction; a set of solar cells configured for converting optical energy into electrical signals; and/or a set of motion/vibration transducers configured for generating electrical signals or pulses in response to PWSD motion/vibration.

The primary processing unit(s) 110 can include or be a general purpose processing unit configured for executing stored program instructions, and the secondary processing unit(s) 122 can include or be a special-purpose processing unit configured for performing/accelerating image processing operations.

The set of cameras 130 can include or be implemented as one, two, three, or more cameras 130, each of which has an image capture or optical axis aligned relative to or along a particular PWSD axis. In certain representative non-limiting embodiments, the PWSD 100 includes at least one x-axis camera 130$x$, at least one y-axis camera 130$y$, and at least one z-axis camera 130$z$. Additionally or additionally, the PWSD 100 can include one or more multi-axis cameras, such as an x-y-axis camera (not shown), an x-z-axis camera (not shown), and a y-z-axis camera (not shown). Any given camera 130 can include or be a conventional image capture device or image sensor (e.g., a charge coupled device (CCD)) and associated lens/optical elements configured for capturing or encoding at least 2D visual/optical information corresponding to a plane perpendicular to the particular PWSD axis or axial direction relative to or along which the image capture or optical axis of the camera 130 is aligned. Furthermore, in multi-camera PWSD embodiments, the cameras 130 are configured such that any given camera's field of view (FoV) at least slightly overlaps with another camera's FoV. As a result, portions of individual images captured by distinct or separate cameras 130 overlap, which facilitates the generation of composite images that provide visually contiguous or continuous views into portions of the PWSD user's 3D spatial surroundings. One or more cameras 130 can include a wide angle, fisheye, or other type of lens (e.g., a catadioptric lens) that facilitates, enables, or establishes such FoV overlap, in a manner readily understood by an individual having ordinary skill in the relevant art. In some embodiments, one or more cameras 130 and lenses/optical elements associated therewith are configured for capturing infrared images, in addition or as an alternative to cameras 130 configured for capturing visible light images.

The sensing/monitoring subsystem 140 includes multiple types of sensors 142 such as particular types of sensors described above, including sensors configured for capturing or generating sensed/measured signals corresponding to (a) the PWSD user's current physiologic state; (b) the current spatial orientation of the PWSD 100/PWSD user (e.g., relative to the PWSD's spatial axes); (c) the current geospatial location/coordinates of the PWSD 100/PWSD user; and (d) one or more current distances of the PWSD 100 away from objects in the PWSD's surrounding environment (e.g., nearby/closest objects from which ultrasonic and/or optical signals are reflected most strongly). The sensing/monitoring subsystem 140 can be configured for receiving signals or data from PWSD assistive apparatuses/devices 400, as indicated above. The sensing/monitoring system 140 can additionally include signal conditioning/filtering/amplification/preprocessing circuitry corresponding to particular sensors, in a manner readily understood by individuals having ordinary skill in the relevant art.

The set of input devices 150 includes a number of user selectable buttons and/or switches, and the display device 160 includes a touch or proximity sensitive display screen. Thus, the display device 160 can be defined as an extension or portion of the set of input devices 150, e.g., as an input/output device.

The communication subsystem 180 includes a cellular modem 182, a set of antennas 184 including a cellular communication antenna, and a Subscriber Identity/Identification Module (SIM) card interface 186 into which at least one SIM card (e.g., a micro-SIM card) can be inserted (e.g., removably inserted). The communication subsystem 180 can further include a secondary/additional wireless communication interface 190 that includes circuitry which operates in accordance with one or more non-cellular wireless communication protocols, such as WiFi, Bluetooth®, or another protocol. The communication subsystem 180 can also include a wire-based communication interface 195, such as a micro-USB interface.

In a number of embodiments, at least some of the PWSD's electrical devices/circuitry are provided by way of a mobile communication/smartphone chipset implemented as a System on a Chip (SoC), which provides a set of processing units (e.g., multiple processing cores, plus at least one GPU) configured for executing stored program instructions, and which is configurable/configured for supporting multiple types of wireless communication including cellular/mobile network communication; typically at least one mode of wire-based communication; plus additional types of functionality including image capture functionality and geolocation functionality. In a representative implementation, a PWSD chipset can include an SoC having an architecture that is at least generally related to, based upon, or an extension or counterpart of a Qualcomm Snapdragon SoC (Qualcomm Incorporated, San Diego, Calif. USA) or similar type of mobile communication/smartphone SoC. In various embodiments, a PWSD chipset is based on or includes an SoC that is adapted or designed to support at least three cameras 130. However, in certain embodiments, a PWSD includes a set of chipsets in which each chipset supports only two cameras 130.

The PWSD's memory unit 200 includes a primary or main memory 210 having one or more types of nonremovable information storage media (e.g., one or more types of Random Access Memory (RAM) and Read Only Memory (ROM)); and a removable memory interface 220 configured for removably engaging with or receiving one or more types of removable storage media 225 (e.g., removable memory cards), in a manner readily understood by individuals having ordinary skill in the relevant art. Portions of the PWSD's internal database 230 can reside within the main memory 210 and/or removable storage media 225. The imaging subsystem memory 124 also includes one or more types of information storage media, which can analogously include nonremovable and/or removable media. The main memory 210 and the imaging subsystem memory 124 can store signals, data, and program instruction sets/modules/units (e.g., firmware and/or software modules) that when executed by the PWSD's set of processing units facilitate, enable, manage, control, or perform particular types of PWSD operations, processes, or functions.

Figure 3:
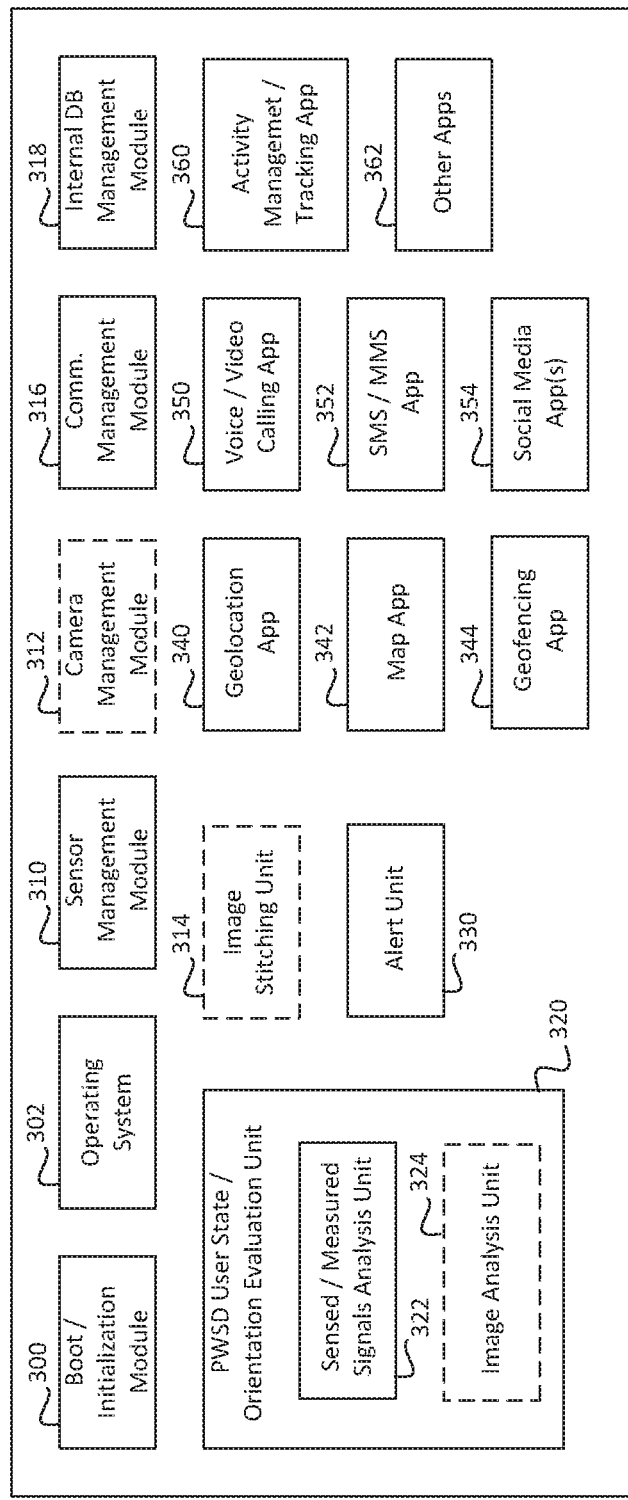
FIG. 3 is a block diagram showing a number of PWSD program instruction sets/modules/units resident within a primary memory and an imaging memory in accordance with a representative embodiment of the present disclosure.

FIG. 3 is a block diagram showing a number of PWSD program instruction sets/modules/units resident within the primary memory 210 and the imaging memory 124 in accordance with a representative embodiment of the present disclosure. In the embodiment shown in FIG. 3, particular PWSD program instruction sets/modules/units that typically reside in the primary memory 210 are shown with solid lines, and PWSD program instruction sets/modules/units that typically or possibly reside in the imaging subsystem memory 124 are shown with dashed lines. As indicated, the PWSD 100 includes a PWSD boot/initialization module 300; an operating system 302 configured for managing access to and utilization of PWSD hardware and program instruction set resources; a sensor management module 310 configured for managing the automatic acquisition/generation and storage of sensed/measured signals from the sensing/monitoring subsystem 140, and possibly or typically the acquisition and storage of particular sensed signals in response to PWSD user input; a camera management module 312 configured for controlling/managing the acquisition of images from the PWSD's set of cameras 130, such as the acquisition of image singlets, image doublets, or image triplets (e.g., (x, y, z) image triplets) and possibly or typically the acquisition of individual or multiple images from one or more cameras 130 in response to PWSD user input; typically or possibly an image stitching unit 314 configured for processing a given multi-image dataset (e.g., an (x, y, z) image triplet dataset) to unify, join, or stitch together the individual images thereof to form a composite image dataset; a communication management module 316 configured for managing communication between the PWSD 100 and external electronic/computing devices or destinations including the set of remote servers 500, possibly or typically target electronic/computing destinations, and possibly a PWSD assistive apparatus/device 400 and/or a local electronic/computing device 480; and an internal database management module 318 configured for managing and updating the contents of the PWSD's internal database 230 (e.g., by way of information transfer involving the remote database 700).

As indicated above, in several embodiments a PWSD 100 further includes program instruction sets/modules configured for (a) processing/analyzing sensed signals, and based upon such processing/analysis, capturing one or more image singlets, doublets, or triplets in accordance with the number of cameras 130 with which the PWSD 100 is equipped; (b) possibly or typically obtaining or generating a set of composite images therefrom; and (c) communicating sensed signals as well as one or more temporally associated image singlet, image doublet, or image triplet datasets and/or composite image datasets to the set of remote servers 500 for further processing/analysis. In various embodiments, the PWSD 100 additionally includes program instruction sets/modules configured for processing/analyzing sensed signals plus image datasets and/or composite images temporally associated or linked therewith separate or independent of the set of remote servers 500, and based upon such processing/analysis, selectively issuing SMS/MMS messages to the set of remote servers 500 requesting the issuance of alerts to target alert recipients associated with the PWSD user.

In view of the foregoing, a PWSD's memory, including its primary memory 210 and the image subsystem memory 124, can include a PWSD user state/orientation evaluation unit 320 having a sensed/measured signals analysis unit 322, and typically or possibly an image analysis unit 324 (e.g., a composite image analysis unit 324), which are respectively configured for processing or analyzing sensed/measured signals and image datasets (e.g., corresponding to composite images), and which can possibly analyze PWSD user information stored in the PWSD's internal database 230 to determine whether the PWSD user's currently determined physiological state and/or orientation indicate or correspond to an undesirable, unexpected, abnormal, dangerous, or emergency situation. The PWSD's primary memory 210 can further include an alert unit 330 configured for generating one or more SMS/MMS messages directed to the set of remote servers 500 in the event that such an undesirable, unexpected, abnormal, dangerous, or emergency situation likely exists or exists. Moreover, in the event that the PWSD user's physiological state and physical orientation return to and remain in an expected or normal condition for a minimum amount of time after alert issuance, thereby indicating the absence or cessation of the undesirable, unexpected, abnormal, dangerous, or emergency situation, the alert unit 330 can generate an appropriate alert cancellation SMS/MMS message directed to the set of remote servers 500.

In some embodiments, in order to determine whether an undesirable, unexpected, abnormal, dangerous, or emergency situation exists or likely exists, the PWSD user state/orientation evaluation unit 320 can determine whether (a) most-recently acquired/generated sensed/measured signals corresponding to the PWSD user are within or outside of an expected or normal range in view of normal ranges for the sensed signals relative to a population of individuals representative of the PWSD user, and/or relative to the PWSD user's sensed/measured signal history, activity schedule/history, and/or medical history stored within the PWSD's internal database 230; and typically or possibly (b) one or more most-recently generated composite images indicate or confirm that that the PWSD user's physical surroundings or orientation therein correspond to an undesirable, unexpected, abnormal, dangerous, or emergency situation, such as an occurrence of a fall from an upright standing or sitting posture to a prone or downward facing posture relative to which the PWSD user has not regained a standing or sitting posture within a short or relatively short time interval (e.g., approximately 5-60 seconds, or about 10-30 seconds).

If an undesirable, unexpected, abnormal, dangerous, or emergency situation currently exists or likely exists, the alert unit 330 in association with the communication management module 316 can accordingly issue one or more SMS/MMS messages to the set of remote servers 500.

In addition to the foregoing, a PWSD's primary memory 210 typically stores a number of other/additional/adjunctive program instruction sets/modules/applications that facilitate or enable other/additional/adjunctive types of functionality, for instance, particular types of mobile telephone/smartphone functionality. Such program instruction sets/modules can include one or more of a geolocation tracking app 340 configured for monitoring/tracking the PWSD's geospatial coordinates (e.g., Global Positioning Satellite (GPS) coordinates); a map app 342 that can operate in association with the geolocation tracking app 340, and which can provide visual and/or audio indications of the PWSD's geospatial location; a geofencing app 344 that cooperatively functions with the geolocation tracking app 340 and possibly the map app 342 for indicating whether the PWSD 100 is within or outside of a programmably defined/selected geofence; a voice/video calling app 350 configured for making and receiving voice/video calls; an SMS/MMS app 352 configured for sending and receiving SMS/MMS messages, including SMS/MMS messages defined by the PWSD user; a number of social media apps 354, each of which is configured for communicating with a social media service (e.g., WhatsApp, Line, Twitter, Facebook, Weibo, etc. . . . ); an activity management/tracking app 360 configured for monitoring and managing scheduled PWSD user activities such as intended exercise periods and medical appointments; and/or other apps 362, such as a web browser. Depending upon embodiment details, a given additional/adjunctive program instruction set/module can be a built-in or a downloadable/downloaded app, in a manner readily understood by individuals having ordinary skill in the relevant art.

Aspects of Representative Smartwatch PWSD Embodiments

As indicated above, a PWSD 100 can exist in various forms. In several embodiments, a PWSD 100 exists in the form of wrist-wearable or wrist-worn device such as a smartwatch. FIGS. 4A-4E are schematic illustrations showing portions of a representative smartwatch PWSD 100 configured for capturing images along orthogonal x, y, and z axes and providing at least some types of PWSD and mobile telephony functionality in accordance with particular embodiments of the present disclosure. In an embodiment, the smartwatch 100 includes a generally thin or thin housing or case 102 having an upper or top surface that carries a touch sensitive display screen 160 by which a GUI is presented to the PWSD user, and which can detect/receive user touch and/or gesture based user input directed to the GUI (e.g., in response to PWSD user finger motion(s)) in a manner readily understood by individuals having ordinary skill in the relevant art. The case 102 also includes a lower or bottom surface (not shown) that is intended or expected to reside upon or against the PWSD user's wrist when the smartwatch 100 is worn, in a manner readily understood by an individual having ordinary skill in the relevant art. The case 102 further includes a plurality of side surfaces or edges about its periphery between its upper/top and lower/bottom surfaces. In several embodiments, from a top view the shape of the case 102 is octagonal. However, the case 102 can exhibit other shapes in other embodiments.

The set of input devices 150 provided by the smartwatch 100 includes a microphone 155, as well as plurality of buttons disposed at predetermined locations relative to the periphery of the case 102 or display screen 160. In a number of embodiments, the set of buttons includes a "home" button 152 disposed on the upper face of the case 102, for instance, at a location intended or expected to be furthest from the PWSD user's wrist joint (or closest to the PWSD user's forearm/elbow) when the smartwatch 100 is worn; a GUI navigation or "back/forward button" 154 disposed at an outer left forward edge of the case 102 when the smartwatch 100 is worn; an emergency/help button 156 disposed at an outer right forward edge of the case 102 when the smartwatch 100 is worn; and a volume button 158 disposed along a portion of a left edge or a right edge of the case 102. The smartwatch 100 also includes a speaker 170 carried by the case 102 at a predetermined location, for instance, on a rearmost edge of the case 102 below the home button 152.

Figure 4A:
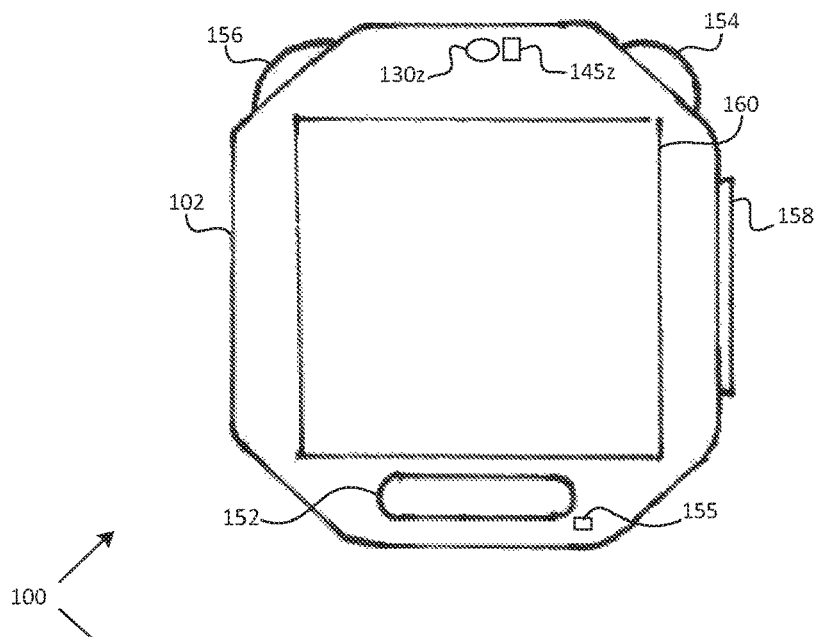
FIGS. 4A-4E are schematic illustrations showing portions of a representative smartwatch PWSD configured for capturing images along orthogonal x, y, and z axes and providing at least some types of PWSD and mobile telephony functionality in accordance with particular embodiments of the present disclosure.
Figure 4B:
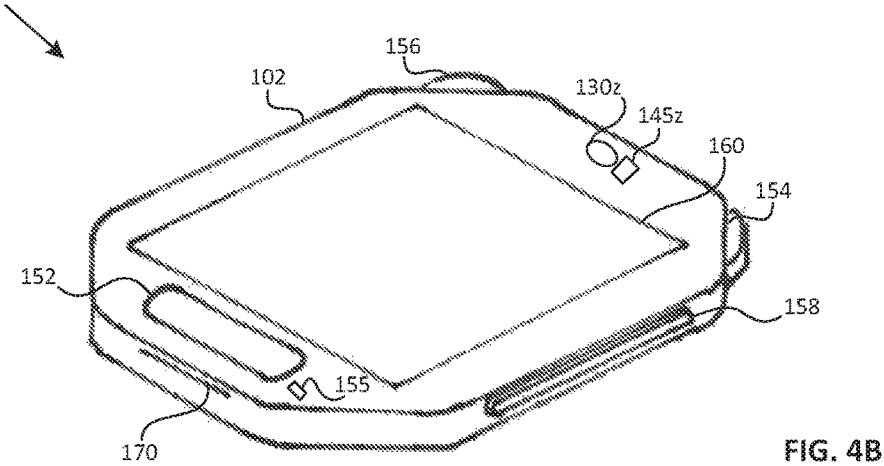
Figure 4C:
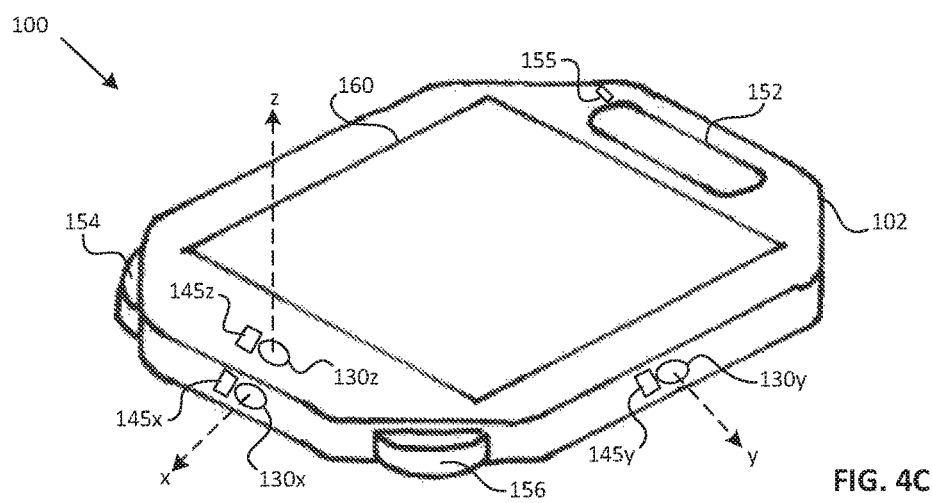
Figure 4D:
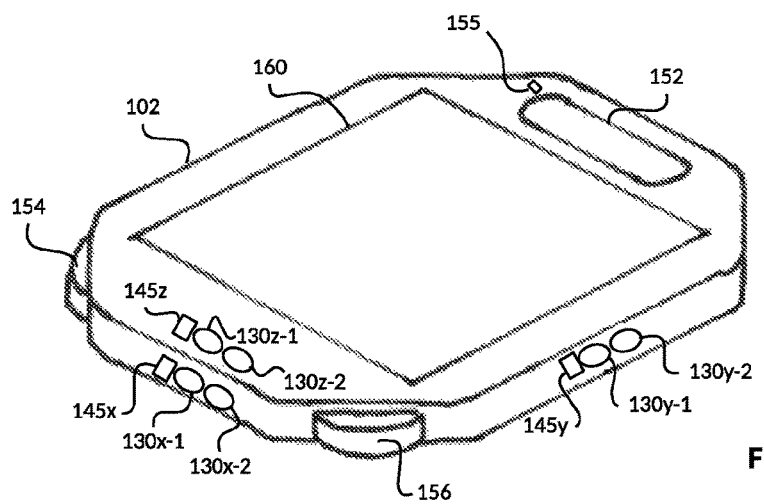
Figure 4E:
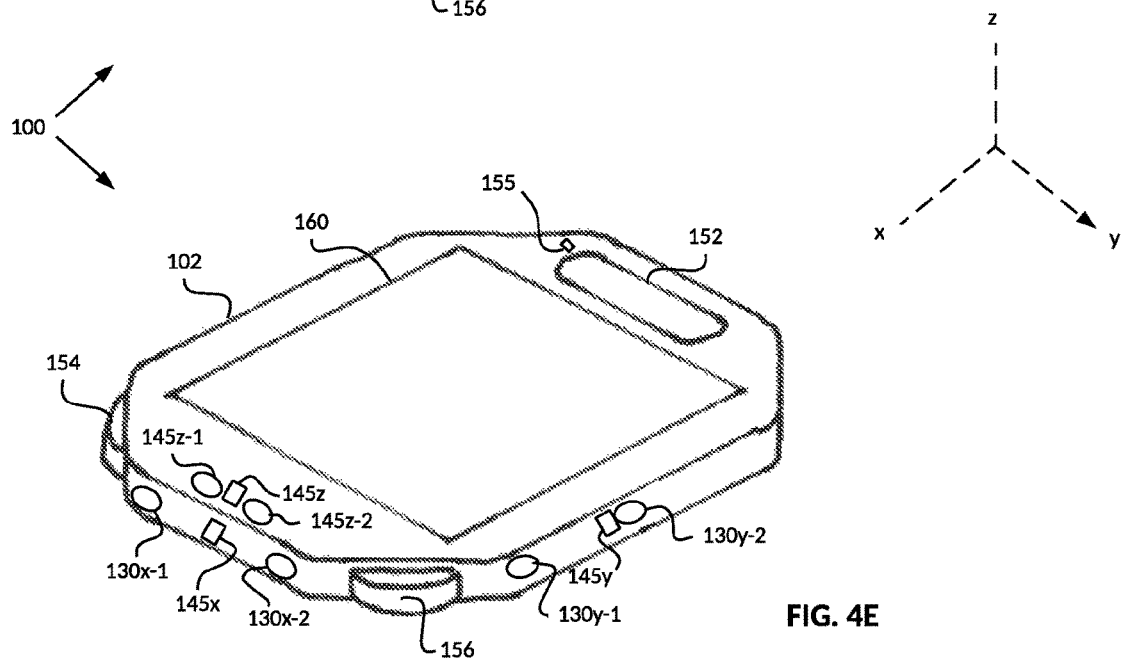

In the representative embodiment shown in FIGS. 4A-4C, the smartwatch 100 includes an x-axis camera 130x, a y-axis camera 130y, and a z-axis camera 130z, which are respectively oriented along an x-axis, a y-axis, and a z-axis corresponding to three orthogonal or approximately orthogonal faces of the smartwatch 100. More particularly, in the embodiment shown, an x-axis of the smartwatch 100 is defined perpendicular to a forward or frontmost edge of the smartwatch 100, which is expected or intended to be disposed closest to the PWSD user's wrist when the smartwatch 100 is worn. The y-axis of the smartwatch 100 is defined perpendicular to a left side edge of the smartwatch 100, perpendicular to the x-axis; and the z-axis of the smartwatch 100 is defined perpendicular to the upper surface of the smartwatch 100, perpendicular to each of the x-axis and the y-axis. The z-axis is thus intended or expected to be oriented in a direction toward or generally toward the PWSD user's face when the PWSD user 100 is looking directly at and interacting with the display screen 160.

Thus, the x-axis camera 130x is disposed on a forward/frontmost edge of the smartwatch 100 that is perpendicular to the x-axis of the smartwatch 100; the y-axis camera 130y is disposed on a left or right side edge of the smartwatch 100 that is perpendicular to the y-axis of the smartwatch 100; and the z-axis camera 130z is disposed on the upper surface of the case 102, perpendicular to the z-axis of the smartwatch 100. Stated equivalently, the x-axis camera 130x, the y-axis camera 130y, and the z-axis camera 130z are carried by the case 102 such that an optical or image capture axis of each such camera 130x, 130y, 130z is oriented along the x-axis, the y-axis, and the z-axis of the smartwatch 100, respectively. Hence, in an embodiment the x-axis camera 130x is configured for capturing 2D images across an FoV that spans portions of the y-axis and the z-axis (i.e., the y-z plane) of the smartwatch 100; the y-axis camera 130y is configured for capturing 2D images across an FoV that spans portions of the x-axis and the z-axis (i.e., the x-z plane) of the smartwatch 100; and the z-axis camera 130z is configured for capturing 2D images across an FoV that spans portions of the x-axis and the y-axis (i.e., the x-y plane) of the smartwatch 100.

In the embodiment shown, the smartwatch 100 also includes at least one distance/proximity sensor 145, such as an x-axis distance/proximity sensor 145x, a y-axis distance/proximity sensor 145y, and a z-axis distance/proximity sensor 145z, each of which is respectively disposed perpendicular to the x-axis, the y-axis, and the z-axis of the smartwatch 100/case 102, and each of which is configured for detecting a distance between the smartwatch 100 and a nearest object or surface, or the proximity of the smartwatch 100 to an object or surface along an axis with which it is aligned. A given distance/proximity sensor 145 can include or be a radar-based distance/proximity sensor, an ultrasonic distance/proximity sensor, and/or an optical distance/proximity sensor, in a manner readily understood by an individual having ordinary skill in the relevant art. For instance, a radar-based distance/object proximity sensor can be similar or analogous to, be based on, include, or be a radar chip used in a Project Soli smartwatch by Google (Google Inc., Mountain View, Calif. USA).

In certain embodiments, the smartwatch 100 carries more than one camera 130 along at least one of its x-axis, y-axis, and z-axis. For instance, in specific representative embodiments shown in FIGS. 4D-4E, the smartwatch 100 can include two x-axis cameras 130x-1, 130x-2; two y-axis cameras 130y-1, 130y-2; and two z-axis cameras 130z-1, 130z-2.

Figure 4F:
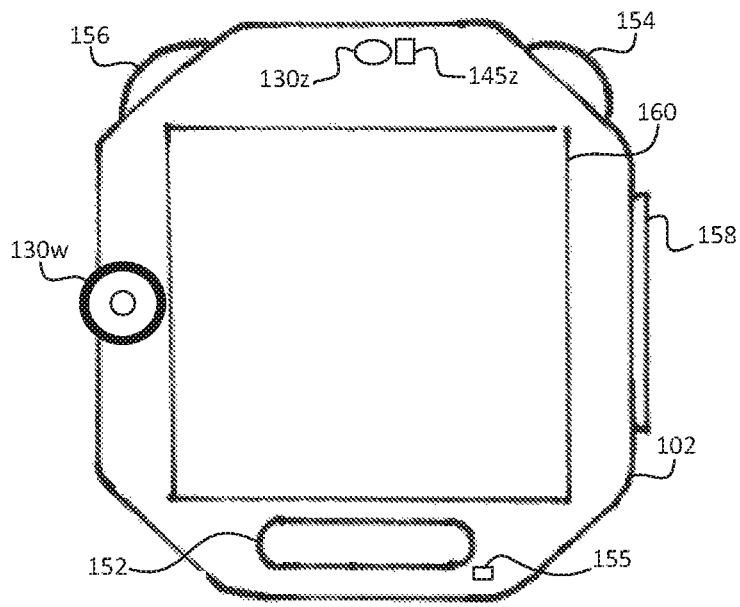
FIGS. 4F-4G are schematic illustrations showing portions of representative smartwatch PWSDs that include wide or very wide angle camera units in accordance with certain embodiments of the present disclosure.
Figure 4G:
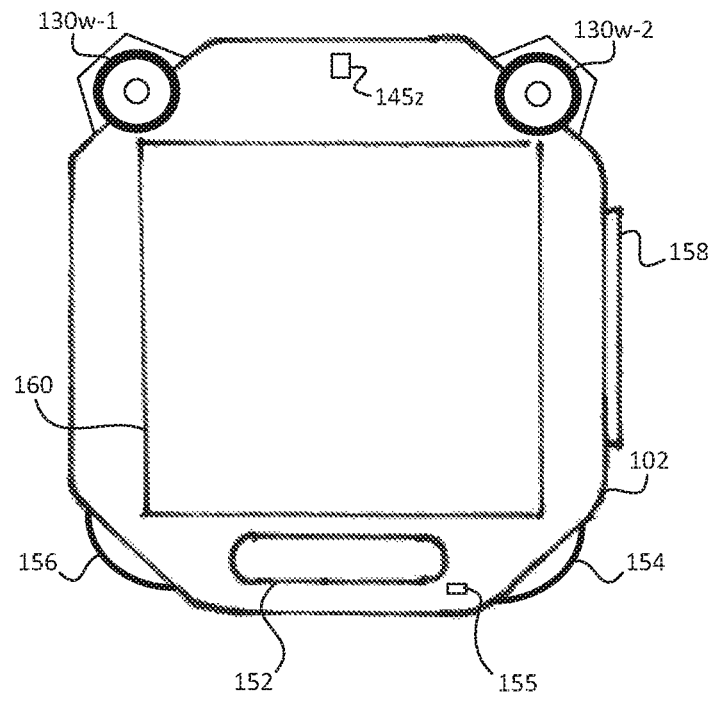
Figure 5A:
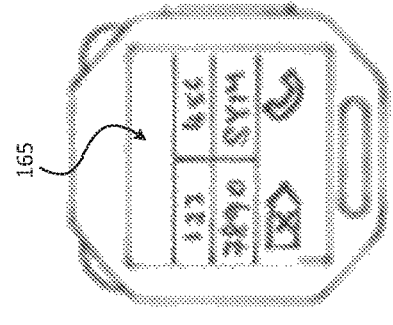
Figure 5A:
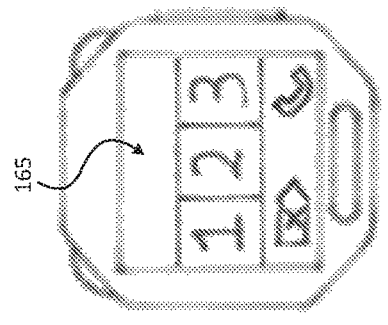
Figure 5A:
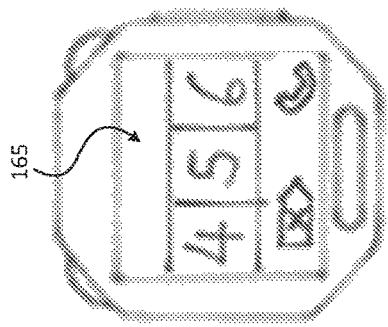
Figure 5A:
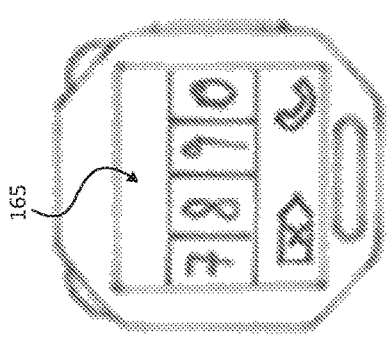
Figure 5B:
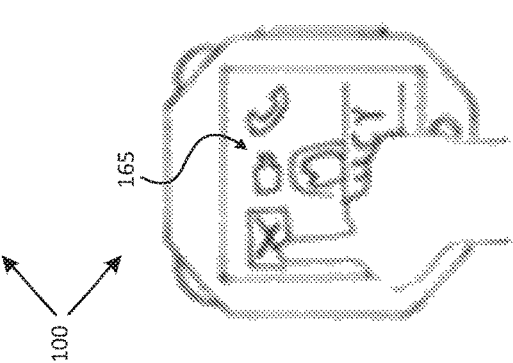
Figure 5B:
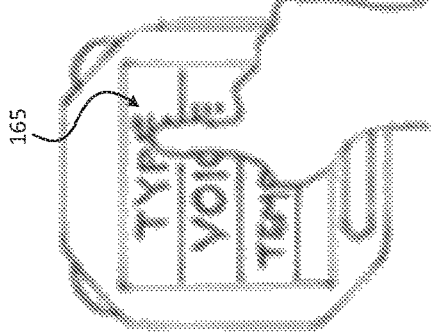
Figure 5B:
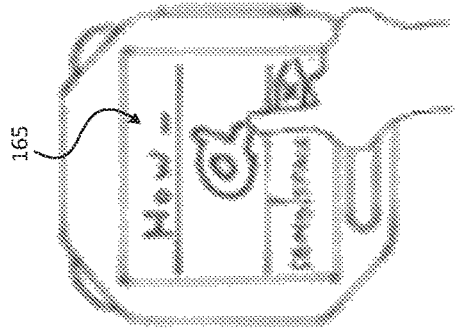
Figure 5B:
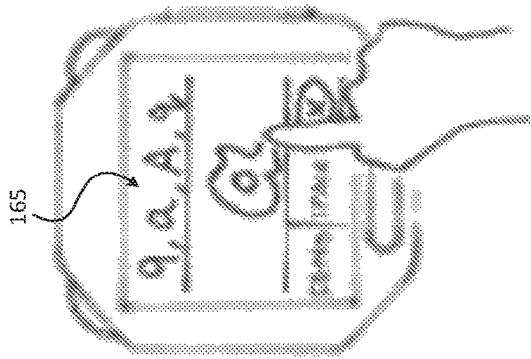

In addition or as an alternative to the foregoing, in some embodiments the smartwatch 100 carries one or more wide angle camera units or cameras (e.g., one, two, three, or more wide angle camera units), each of which includes or is an image capture device that is coupled to or equipped with a wide or very wide angle lens, lens arrangement, or lens assembly. Each wide or very wide angle camera unit is configured to have a wide or very wide FoV (e.g., ranging between approximately 110-170 degrees, or about 130-150 degrees, in x, y, and/or z directions), such that an image captured thereby encompasses a significant or very significant portion of the environment external to the smartwatch 100 (e.g., the FoV of a particular wide or very wide angle camera unit can encompass or extend beyond two orthogonal PWSD spatial axes). FIG. 4F is a schematic illustration of a smartwatch 100 that carries a single wide angle camera unit 130w in accordance with an embodiment of the present disclosure; and FIG. 4G is a schematic illustration of a smartwatch 100 that carries dual wide angle camera units 130w-1, 130w-2 in accordance with an embodiment of the present disclosure. In a smartwatch 100 having a single wide angle camera unit 130w, the single wide angle camera unit 130w can be disposed along, at, or on a predetermined outer or outward portion of the smartwatch 100; and in a smartwatch 100 having dual wide angle camera units 130w-1, 130w-2, the two wide angle camera units 130w-1,2 can be disposed at predetermined outer or outward portions of the smartwatch 100 such that their FoVs at least partially overlap in a manner that facilitates or simplifies the generation of a composite image from individual wide or very wide angle images captured by each wide angle camera unit 130w-1, 2. In such embodiments, particular buttons 154, 156 can be repositioned or disposed at different locations relative to their positions indicated in FIGS. 4A-4E.

In a smartwatch 100 having a wide angle camera unit 130w, the wide angle camera unit 130w can be carried or supported by the smartwatch 100 such that its image capture plane is disposed at a particular angle (e.g., a predetermined or selectable/adjustable angle) relative to the upper surface of the case 102 or display screen 160 of the smartwatch 100, such that FoV of the wide angle camera unit 130w angularly extends around or beyond (e.g., "wraps around") the case 102 of the smartwatch 100 in an intended manner. A wide angle camera unit 130w can be similar to, be based on, include, or be a camera and lens arrangement such as that found in the commercially available LG G5 smartphone (LG Corporation, Seoul, South Korea).

In various embodiments of a smartwatch 100, one or more sensors 142 that acquire or generate signals that are processed/processable by circuitry internal to the case 102 can be carried by outer portions of the case 102, communicate signals through openings in the case 102, or be disposed external to the case 102. For instance, a smartwatch 100 in accordance with an embodiment of the present disclosure can include a set of optical sensors (not shown) configured for emitting/detecting optical signals through openings in the bottom surface of the case 102, and can be configured for monitoring the PWSD user's heart/pulse rate (e.g., in a manner essentially identical, similar, or analogous to the optical sensors provided by an Apple Watch (Apple Inc., Cupertino, Calif. USA). Alternatively, a conventional heart rate/pulse sensor (not shown) can be carried by or integrated with a PWSD wrist band (not shown), and can be configured for detecting the PWSD user's heart beat/pulse when the PWSD 100 is secured or strapped to/about the PWSD user's wrist, in a manner readily understood by an individual having ordinary skill in the relevant art.

FIGS. 5A-5H are illustrations showing aspects of a representative set of smartwatch GUIs 165 providable/provided by a smartwatch PWSD 100 such as that illustrated in FIGS. 4A-4E in accordance with an embodiment of the present disclosure. In various embodiments, a PWSD user can interact with the smartwatch GUI 165 to dial a telephone number to call a person. In some embodiments, when the PWSD user selects or taps a displayed digit sequence such as "123," "456," or "7890," the GUI 165 subsequently presents individual numbers within the selected number sequence in an enlarged format on the PWSD display device 160 to enable PWSD user selection of any such individual number, for instance, in manner indicated in FIG. 5A.

A PWSD user can additionally interact with the smartwatch GUI 165 to generate SMS/MMS message content, such as by way of PWSD user selection of an SMS/MMS icon displayed by the GUI 165. Following user selection of the SMS/MMS icon, the GUI 165 can present selectable options to the PWSD user to facilitate or enable user entry of text or handwritten or finger-drawn characters in a manner indicated in FIG. 5B, or user recording/playback of a voice message in a manner indicated in FIG. 5C.

A PWSD user can swipe their finger across the display screen 160 to move from one portion of the GUI 165 to another, or to select a particular app icon from among multiple app icons presented by the GUI 165, such as indicated in FIG. 5D. After PWSD user selection of a given app icon, the corresponding app can be launched and executed by the PWSD 100, in a manner readily understood by individuals having ordinary skill in the relevant art. For instance, FIG. 5E illustrates a health app icon and functionality provided thereby such as pedometer and heart rate monitoring functionality; FIG. 5F illustrates a camera app icon, and a representative image captured following PWSD user selection of the camera app icon and launching/execution of the corresponding camera app. In some embodiments, a camera app is responsive to PWSD user input directed to the GUI 165 by which the PWSD user can select a particular PWSD camera 130$x,y,z$ (or wide angle camera unit 130$w$-1, 2) with which an image will be captured. In response to PWSD user selection of a calling app icon corresponding to a particular telephone contact name, such as "Lucy," a corresponding calling app dials the telephone number of this contact, and can track a call duration in a manner indicated in FIG. 5G.

In response to PWSD user selection of the emergency/help button 156 or an emergency/help icon presented by the GUI 165, the GUI 165 can provide an interface by which the PWSD user can select a particular target alert recipient, and/or call at least one target alert recipient, for instance, in a manner indicated in FIG. 5H.

Aspects of Representative Remote Server Embodiments

Figure 6:
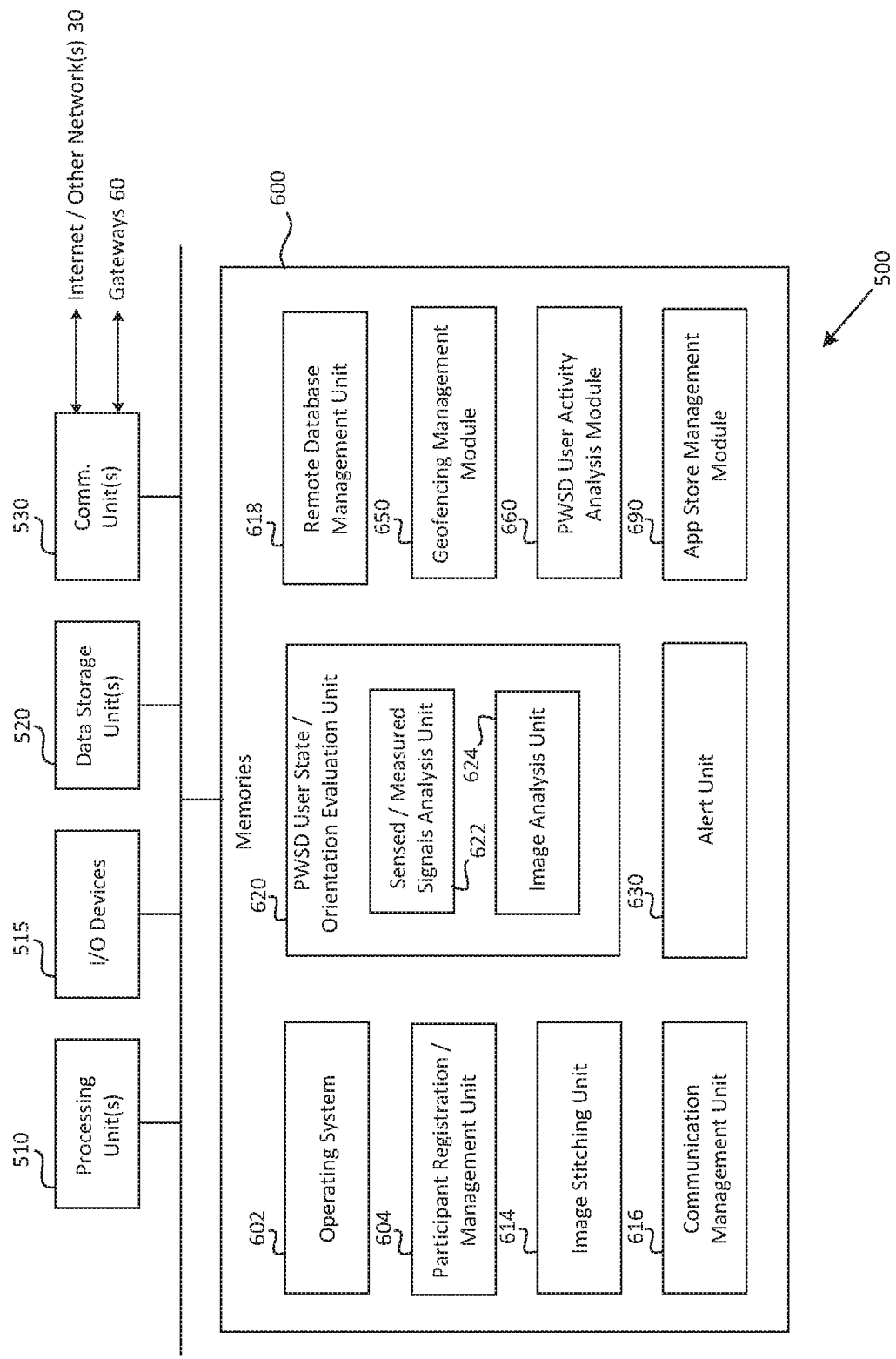
FIG. 6 is a block diagram showing portions of a set of remote servers in accordance with an embodiment of the present disclosure, including particular representative program instruction sets/modules/units within a set of memories 600 provided by the remote server(s).

FIG. 6 is a block diagram showing portions of a set of remote servers 500 in accordance with an embodiment of the present disclosure. In an embodiment, the set of remote servers 500 includes a number of processing units 510 configured for executing stored program instructions; a set of input/output devices 515 configured for enabling server administrator interaction with the set of remote servers 500; a number of data storage units 520, in which portions of the remote database 700 can typically or possibly reside; at least one communication unit 530 configured for managing communication with PWSDs 100 and distributing/sending alerts to target electronic/computing destinations (e.g., by way of the Internet 30 and/or the set of gateways 60); and one or more memories 600 configured for storing program instruction sets/modules/units, data, signals, and other information. The set of servers 500 can be cloud based, and can be dynamically allocatable/allocated. The data storage units 520 and/or the set of gateways 60 can also be cloud based, and can further be dynamically allocatable/allocated.

FIG. 6 also illustrates particular representative program instruction sets/modules/units within the set of memories 600 provided by the remote server(s) 500 in accordance with an embodiment of the present disclosure. In an embodiment, such program instruction sets/modules include an operating system 602; a participant registration/management unit 604 configured for performing PWSD user and associated target alert recipient registration and alert service participant management procedures; typically or possibly an image stitching unit 614 configured for processing multi-image datasets (e.g., image triplet datasets) to unify, join, or stitch together individual images to form corresponding composite image datasets; a communication management module 616 configured for managing communication between the remote server(s) and PWSDs 100, the communication of alerts and alert cancellations to target electronic/computing destinations, and possibly communication with PWSD assistive apparatuses/devices 400; and a remote database management unit 618 configured for managing and updating the contents of the remote database 700.

The set of memories 600 further includes program instruction sets/modules/units configured for (a) processing or analyzing sensed/measured signals and composite images associated or temporally linked therewith which have been received from PWSDs 100, and (b) for any given PWSD 100, selectively generating alerts directed to one or more associated target electronic/computing destinations based upon such processing/analyzing. For instance, a set of memories 600 can include a PWSD user state/orientation evaluation unit 620 having a sensed/measured signals analysis unit 622 and a image analysis unit 624 (e.g., a composite image analysis unit 624), which are respectively configured for processing or analyzing sensed/measured signals and image datasets (e.g., composite image datasets) received from each PWSD 100, possibly or typically in association with processing/analyzing corresponding PWSD user history information stored in the remote database 700, to determine whether a given PWSD user's physiological state and/or orientation indicate or correspond to an undesirable, unexpected, abnormal, dangerous, or emergency situation; and an alert unit 630 configured for generating an appropriate set of alerts directed to the target electronic/computing destinations linked with the PWSD user in the remote database 700 in the event that such a situation exists or likely exists. Moreover, in the event that the PWSD user's physiological state and physical orientation return to and remain in an expected or normal condition for a minimum amount of time after alert issuance, thereby indicating the absence or cessation of an emergency/dangerous situation, the alert unit 630 can generate an appropriate set of alert cancellations.

In several embodiments, in order to determine whether an undesirable, unexpected, abnormal, dangerous, or emergency situation exists or likely exists for a given PWSD user, the PWSD user state/orientation evaluation unit 620 can determine whether (a) one or more most-recently received sensed/measured signals corresponding to the PWSD user are within or outside of an expected or normal range relative to a population of individuals representative of the PWSD user, and/or relative to the PWSD user's sensed/measured signal history, activity schedule/history, and/or medical history stored in the remote database 700; and (b) most-recently received or generated image data corresponding to the PWSD user, such as one or more composite image datasets, indicate or confirm that the PWSD user's physical surroundings or orientation therein correspond to an undesirable, unexpected, abnormal, dangerous, or emergency situation, such as the occurrence of a fall from an upright standing or sitting posture to a prone or downward facing posture relative to which the PWSD user has not regained standing or sitting posture within a short or relatively short time interval (e.g., approximately 5-60 seconds, or about 10-30 seconds). If an undesirable, unexpected, abnormal, dangerous, or emergency situation currently exists or likely exists for the PWSD user under consideration, the alert unit 630 can accordingly generate an appropriate set of alerts, which the communication management module 616 can accordingly issue to some or each of the target electronic/computing destinations associated with the PWSD user in the remote database 700.

The set of memories 600 can also store a number of other/additional/adjunctive program instruction sets/modules that facilitate or enable other/additional/adjunctive types of functionality. For instance, the set of memories 600 can include a geofencing management module 650; a PWSD user activity analysis module 660; and an app store management module 690. The geofencing management module 650 can be configured for defining, storing, and possibly analyzing geofencing information corresponding to a given PWSD user, for instance, in association with a geofencing app that executes on an electronic/computing device (e.g., a desktop, laptop, or tablet computer) usable/used by a target alert recipient associated with the PWSD user. The PWSD user activity analysis module 660 can be configured for analyzing PWSD user activity definitions and activity histories to identify or define expected, typical, or normal sensed/measured signal ranges and possibly expected, typical, or normal composite image contents corresponding to an hourly, daily, weekly, and/or monthly PWSD user activity schedule. Finally, the app store management module 690 can manage the availability of apps/application content in the app store 800.

Aspects of Representative PWSD Assistive Apparatuses/Devices

Figure 7A:
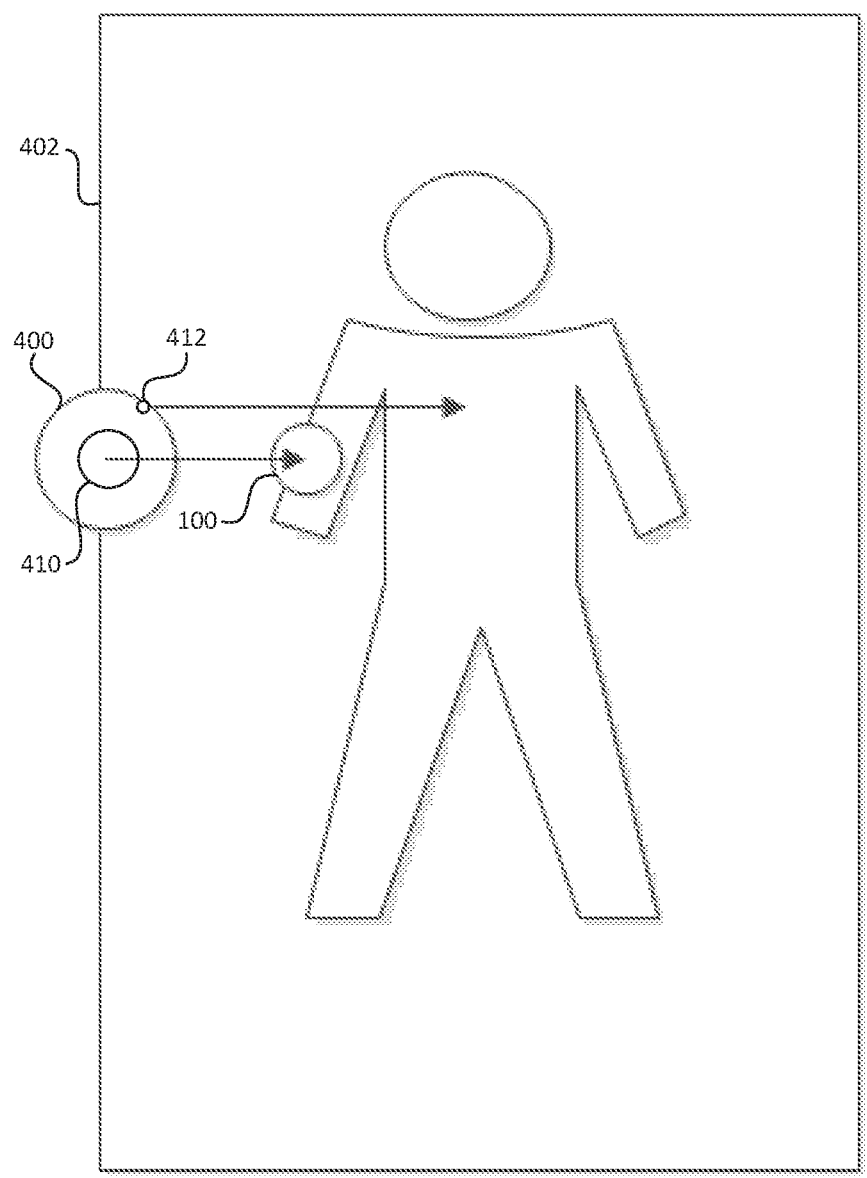
FIG. 7A is a schematic illustration of a PWSD assistive device in accordance with an embodiment of the present disclosure, which includes or is a charging/monitoring apparatus.

FIG. 7A is a schematic illustration of a PWSD assistive device 400 in accordance with an embodiment of the present disclosure, which includes or is a charging/monitoring apparatus 400. The charging/monitoring apparatus 400 includes a wireless charging unit 410 as well as a set of PWSD user monitoring/tracking devices, elements, and/or modules configured for monitoring/tracking the PWSD user's location(s), position(s), and/or orientation(s).

The charging unit 410 includes a conductive coil and associated circuitry (not shown) configured for transferring energy to a corresponding recharging coil in a PWSD 100 by way of magnetic induction, in a manner readily understood by an individual having ordinary skill in the relevant art. The charging unit 410 can be disposed near, adjacent to, on, or under a portion of a support structure 402 such as a bed on which the PWSD user is positionable/positioned or resides, such that their PWSD 100 can be automatically (re)charged while the PWSD user remains at or in a recommended, expected, intended, or required range of locations, positions, and/or orientations relative to the support structure 402 and/or the charging unit 410.

In several embodiments, the charging/monitoring apparatus 400 is coupled to or includes a set of distance/proximity sensors, for instance, a radar-based distance/proximity sensor and/or a number of ultrasonic transducers 412, by which distance(s) between and/or proximity of the charging/monitoring apparatus 400 and one or more portions of the PWSD user's body (e.g., portions of the PWSD user's chest/torso) can be periodically or continuously estimated, measured, determined, or monitored with respect to one or more time intervals (e.g., a predetermined or selectable/programmable number of hours or days, such as nighttime hours only, or 24 hours per day, or during the PWSD user's entire stay in a spatial environment such as a hospital room in which the support structure 402 is disposed).

The charging/monitoring apparatus 400 also includes a processing unit (not shown) as well as a memory (not shown) that stores program instruction sets by which charging/monitoring apparatus operations are managed, controlled, or performed as a result of program instruction set execution by the processing unit. In several embodiments, the charging/monitoring apparatus operations include the (a) generation and storage of distance/proximity signals that indicate or specify distance/proximity measurements between portions of the PWSD user's body relative to portions of the charging/monitoring apparatus 400 and/or the support structure 402; (b) evaluation or analysis of such distance/proximity measurements; (c) determination of whether a current or most-recent distance/proximity measurement exceeds a maximum allowable limit (e.g., a given number of centimeters or meters, such as more than approximately 50 centimeters); and if a current or most-recently determined distance/proximity exceeds the maximum allowable limit, (d) communication with the PWSD 100 and/or possibly the remote server(s) 500, which can result in the capture of additional information by the PWSD 100 (e.g., image singlets, image doublets, or image triplets and sensed/measured signals), the analysis of such additional information, and/or the issuance of an alert to one or more target electronic/computing destinations, such as (i) an IP address corresponding to an electronic/computing device (e.g., a desktop or laptop computer or a mobile telephone) that is accessible to or used by a medical professional or caretaker (e.g., a nurse) responsible for monitoring the PWSD user's location(s), position(s), and/or orientation(s); and/or (ii) an electronic/computing destination corresponding to target alert recipient information associated with the PWSD user by way of the remote database 700.

In certain embodiments, the charging/monitoring apparatus operations additionally or alternatively include monitoring and analyzing impedance changes resulting from variations in positions of the PWSD 100 relative to the charging unit's coil (e.g., on a periodic basis, such as during PWSD (re)charging) to determine whether a current or most-recently determined distance/proximity measurement between the charging unit 410 and the PWSD 100 exceeds a maximum allowable limit.

In specific embodiments, the charging/monitoring unit 400 can itself be coupled to or include a set of image capture devices (e.g., at least one image capture device separate from the PWSD's set of image capture devices 130, such as a set of cameras (not shown) carried by a charging/monitoring apparatus housing or case), and the charging/monitoring apparatus operations can include capturing supplemental/auxiliary images of portions of the spatial environment in which the PWSD user is expected, intended, or required to reside. The charging/monitoring apparatus 400 and/or the set of remote servers 500 can analyze such auxiliary images to aid determination of whether the PWSD user is within or outside of a recommended, expected, intended, or required range of locations, positions, and/or orientations (e.g., relative to the support structure 402).

In view of the foregoing, those having ordinary skill in the relevant art will understand that in some embodiments, the set of PWSD user monitoring/tracking devices, elements, and/or modules provided by the charging/monitoring apparatus 400 (e.g., the set of distance/proximity sensors provided thereby) can also facilitate or enable the determination of (a) whether one or more individuals other than the PWSD user have entered, remain in, or have departed from a spatial environment in which the PWSD user resides; and (b) the selective issuance of alerts based upon the presence or absence of such individuals relative to the PWSD user, possibly in view of known/pre-defined/programmably defined interaction/activity schedules associated with the PWSD user.

FIG. 7B illustrates a PWSD assistive apparatus 450 in accordance with an embodiment of the present disclosure, which includes or is a multi-PWSD monitoring/tracking apparatus 450 configured for monitoring/tracking the presence and/or locations/positions of multiple PWSDs 100a-d within a given spatial environment (e.g., an environment such as a portion of a building or room) 452 in parallel or on a concurrent/simultaneous basis. In an embodiment, the multi-PWSD monitoring/tracking apparatus 450 includes at least three wireless communication nodes 460a-c disposed or mounted at known or predetermined locations relative to or within a particular spatial environment (e.g., a controlled indoor environment such as a room) 452, such that PWSD positions or locations within the spatial environment 452 can be calculated/triangulated. For instance, each wireless communication node 460a-c can be mounted at a particular upper wall or ceiling location in a room 452.

In multiple embodiments, each wireless communication node 460a-c acts as a communication or data transfer hub or node within a wireless communication network that includes a set of external/remote servers 500, which can be coupled to an external/remote database 700. In a number of embodiments, separation distances between each wireless communication node 460a-c and its neighboring wireless communication nodes 460a-c can be stored in the external/remote database 700. Each wireless communication node 460a-c can maintain an internal clock that is synchronized/synchronizable with a master clock (e.g., a master network clock) maintained by the external/remote server(s) 500. Each wireless communication node 460a-c is configured for wireless communication with PWSDs 100 that are within a known, knowable, predictable, or predetermined communication range of the wireless communication node 460a-c. The multi-PWSD monitoring/tracking apparatus 450 includes a sufficient number of wireless communication nodes 460 such that a PWSD 100 disposed at any, essentially any, or nearly any position within the room 452 can wirelessly communicate with at least three wireless communication nodes 460a-c. Hence, depending upon room configuration and/or embodiment details, the multi-PWSD monitoring/tracking apparatus 450 can include more than three wireless communication nodes 460a-c, in a manner readily understood by individuals having ordinary skill in the relevant art. In various embodiments, communication between a PWSD 100 and a wireless communication node 460a-c occurs by way of an RF signal communication protocol, such as WiFi, Bluetooth®, or another wireless RF signal communication protocol (e.g., an RFID/RFID-based or similar communication protocol).

The room 452 typically includes one or more support structures 402 therein such as a number of chairs and/or beds 402a-d on which PWSD users 101a-d can reside. In some embodiments, once a given PWSD user 101a-d and their corresponding PWSD 100a-d are at an intended or desired position or location within the room 452, for instance, relative to or on a particular support structure 402a-d (e.g., on or in a specific bed), a supervisory electronic/computing device 470 (e.g., a tablet computer or smartphone that is coupled to the wireless network) can receive user input from a room supervisor, caretaker, nurse, or other person (e.g., by way of a GUI), and can communicate a monitoring initiation command (e.g., by way of wireless communication) to the PWSD 100a-d corresponding to the PWSD user 101a-d under consideration. The monitoring initiation command can include a support structure ID that identifies the specific support structure 452a-d on which the PWSD user 100a-d under consideration is disposed. In a number of embodiments, a known distance from a predetermined reference point, such as a center point, on each support structure 452a-d to each wireless communication node 460a-c is stored in the external/remote database 700.

In response to receiving a monitoring initiation command, the PWSD 100a-d under consideration communicates with at least one wireless communication node 460 to synchronize an internal PWSD clock with the master clock maintained by the remote server(s) 500, in a manner readily understood by individuals having ordinary skill in the relevant art. Subsequently, this PWSD 100a-d issues or outputs PWSD presence packets on a periodic (e.g., selectable or programmable) basis, for instance, every x seconds (e.g., approximately every 3-60 seconds), or every y minutes (e.g., approximately every 1-5 minutes). In several embodiments, each PWSD presence packet output by a given PWSD 100a-d includes (a) the PWSD ID and/or a Media Access Control (MAC) address corresponding to the PWSD 100a-d, which uniquely identifies the PWSD 100a-d; as well as (b) a sending time stamp that indicates a specific internal PWSD clock time at which the PWSD 100a-d output the PWSD presence packet.

As indicated above, the multi-PWSD monitoring/tracking apparatus 450 is configured such that at least three wireless communication nodes 460a-c can receive PWSD presence packets from each PWSD 100a-d disposed within the room 452, regardless, essentially regardless, or substantially regardless of the PWSD's specific position or location in the room 452. In several embodiments, in response to receiving a PWSD presence packet, a wireless communication node 460a-c appends a receipt time stamp to the PWSD presence packet, and transfers the appended PWSD presence packet to the set of external/remote servers 500. In certain embodiments, a wireless communication node 460a-c can additionally or alternatively append a signal strength level to each received PWSD presence packet, which indicates a signal magnitude or a level of signal degradation that can be correlated with a distance over which the PWSD presence packet traveled between the PWSD 100a-d from which it was output to the wireless communication node 460a-c. The set of external/remote servers 500 analyzes such appended PWSD presence packets corresponding to each PWSD 100a-d (e.g., in sending time stamp or receipt time stamp order) and calculates, estimates, or determines at least one triangulated position or location for each PWSD 100a-d within the room 452 based upon (a) the sending and receipt time stamps within at least three PWSD presence packets corresponding to the PWSD 100a-d under consideration; possibly (b) the ID of a support structure 402a-d with which the PWSD 100a-d is or was initially associated and the known distance of the support structure 402a-d to those wireless communication nodes 460*a-c* from which the external/remote server(s) 500 received the PWSD presence packets corresponding to the PWSD 100*a-d* under consideration; and possibly (c) signal strength levels associated with such PWSD presence packets. The external/remote server(s) 500 can store each calculated/triangulated PWSD position or location corresponding to a given PWSD 100*a-c* in the external/remote database 700.

In the event that the difference between one or more current, most-recent, or recent calculated/triangulated positions or locations for a given PWSD 100*a-d* and an initially calculated/triangulated position or location for the PWSD 100*a-d* exceed a threshold distance (e.g., a predetermined or selectable/programmable threshold distance), the set of external/remote servers 500 issues one or more PWSD data acquisition commands to the PWSD 100*a-d* under consideration. In response, this PWSD 100*a-d* acquires sensed/measured signal sequences, captures multiple sets of images (e.g., multiple (x, y, z) image triplets), and performs multiple distance measurements in a manner essentially identical or analogous to that described above.

The PWSD 100*a-d* under consideration and/or the external/remote server(s) 500 subsequently process/analyze the sensed/measured signal sequences, the multiple sets of images (e.g., multiple (x, y, z) image triplets) or composite images generated therefrom, and the distance measurements to determine whether the PWSD user 101*a-d* under consideration has moved more than a desirable, allowable, or safe distance relative to their initially calculated PWSD position or location, and/or the support structure 402*a-d* on which they are intended or expected to reside. Such processing/analysis can occur in a manner essentially identical or analogous to that described elsewhere herein. If as a result of such processing/analysis the set of external/remote servers 500 determines that the PWSD 100*a-d* and hence the PWSD user 101*a-d* under consideration has moved more than a desirable, allowable, or safe distance relative to the initially calculated PWSD position or location, the external/remote server(s) 500 can issue an alert to the room supervisor, nurse, or caretaker, in a manner essentially identical or analogous to that described above. The foregoing operations can be performed (e.g., in parallel, or in a concurrent/simultaneous manner) for each PWSD 100*a-d* in the room 452, such that the external/remote server(s) 500 can issue one or more alerts corresponding to each PWSD 100*a-d* that has moved beyond a given threshold distance away from its initially calculated/triangulated position or location.

Aspects of Representative Alert Service Participant Registration Processes

Figure 8A:
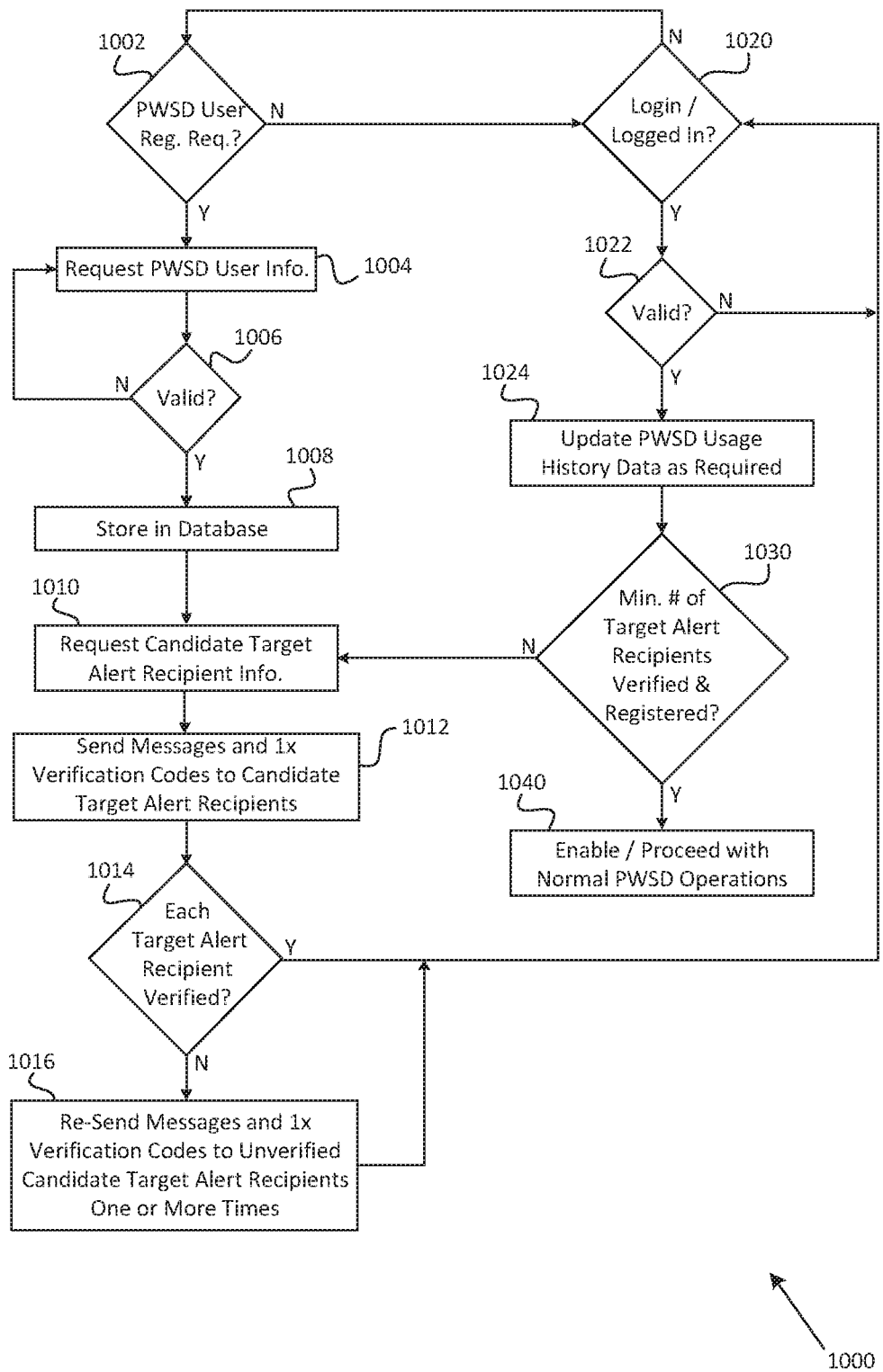
FIGS. 8A-8B are flow diagrams illustrating portions of representative alert service participant registration processes in accordance with an embodiment of the present disclosure.
Figure 8B:
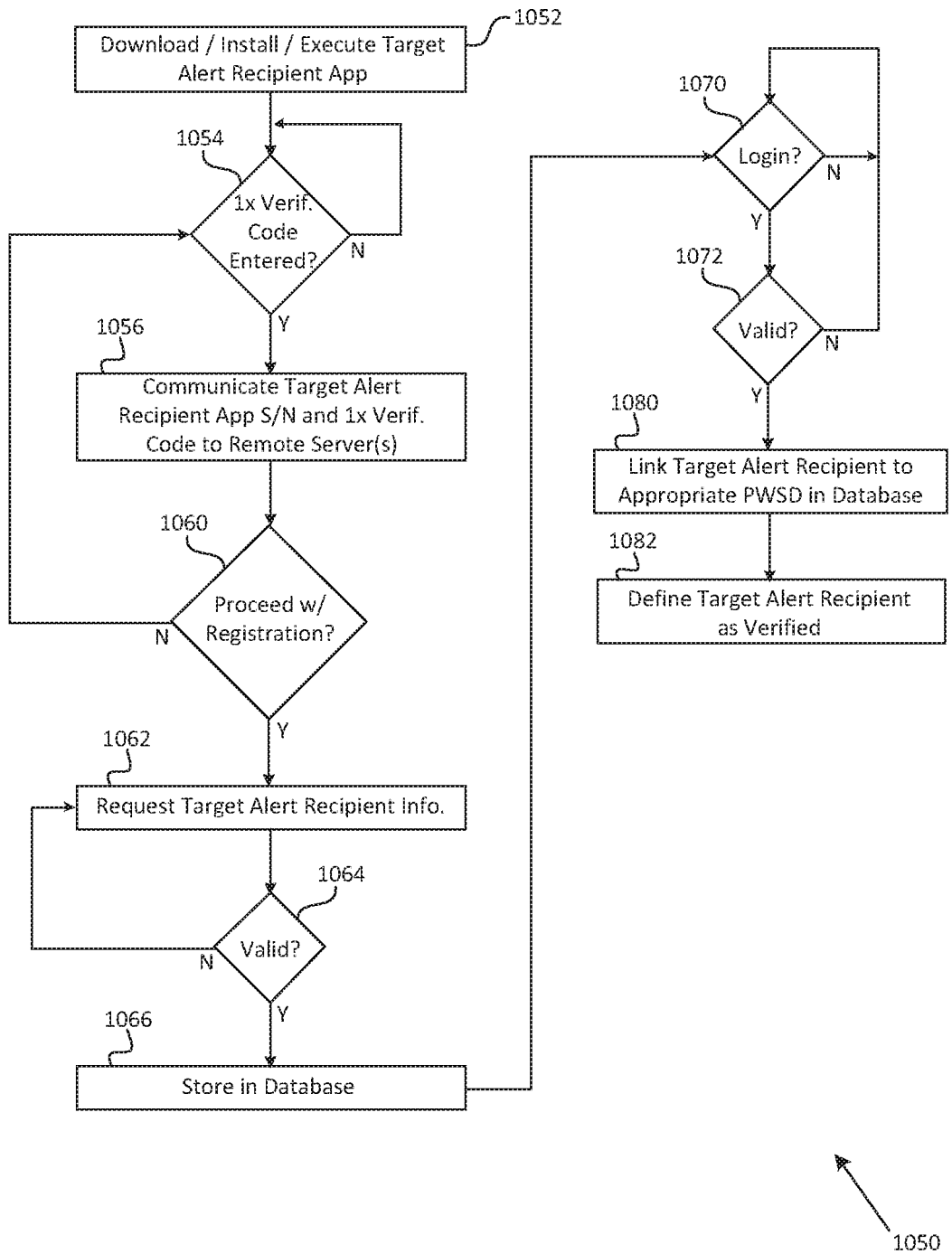

FIGS. 8A-8B are flow diagrams illustrating portions of representative alert service participant registration processes in accordance with an embodiment of the present disclosure. A PWSD user registration process 1000 shown in FIG. 8A includes a first process portion 1002 involving the remote server(s) 500 determining whether a PWSD user registration request has been received from a given PWSD 100. If so, a second process portion 1004 involves requesting and receiving PWSD user information (e.g., a PWSD user name, a PWSD user mailing address, a PWSD user e-mail address, a PWSD user login name and password, and possibly additional PWSD user information). A third process portion 1006 involves determining whether the received PWSD user information is valid, such as by way of an e-mail and/or an SMS/MMS message sent to the PWSD user in accordance with their PWSD user information, to which the PWSD user must successfully submit a response to the remote server(s) 500. If the PWSD user information is not valid, the process 1000 returns to the second process portion 1004. Once the PWSD user information has been validated, a fourth process portion 1008 involves associating the PWSD ID and the validated PWSD user information in the remote database 700.

A fifth process portion 1010 involves requesting PWSD user entry of information identifying one or more candidate target alert recipients, such as by way of e-mail addresses and/or mobile telephone numbers of individuals that the PWSD user prefers, intends, expects to act as their target alert recipients. A sixth process portion 1012 involves the set of remote servers 500 issuing a target alert recipient app download messages and a one-time verification code to each candidate target alert recipient. In the remote database 700, each such one-time verification code can be associated with (a) the unique ID of the PWSD 100 with which the PWSD user under consideration is communicating with the set of remote servers 500, and/or (b) particular PWSD user information such as the PWSD user's login name and possibly a mobile telephone number corresponding to the PWSD 100. In a seventh process portion 1014, the PWSD 100 under consideration communicates with the remote server(s) 500 to determine whether each candidate target alert recipient has been verified as a target alert recipient, such as in a representative manner described below with reference to FIG. 8B. If not, the remote server(s) 500 can re-send target alert recipient app download messages and one-time verification codes to any candidate target alert recipients who have not yet been verified in an eighth process portion 1016.

Once each target alert recipient has been verified, or after the first process portion 1002 in the event that a registration request is not under consideration, a ninth process portion 1020 involves determining whether the PWSD user is performing a login procedure, or is already logged in to the set of remote servers 500. If not, the process 1000 returns to the first process portion 1002. If so, a tenth process portion 1022 involves determining whether the PWSD user's login information is valid. Invalid login information results in the process 1000 returning to the ninth process portion 1020.

If the PWSD user's login information is valid, an eleventh process portion 1024 updates the remote database 700 with PWSD usage history data corresponding to the PWSD 100/PWSD user under consideration. A twelfth process portion 1130 involves remote server determination of whether a minimum number of target alert recipients (e.g., at least 2, 3, 4, 5, or possibly more target alert recipients) have been successfully verified and have successfully registered with the remote server(s) 500. If not, the process 1000 can return to the fifth process portion 1010, such that additional candidate target alert recipient information can be entered. Otherwise, once the number of target alert recipients have been verified and registered by the remote server(s) 500, the remote server(s) 500 and/or the PWSD 100 under consideration can enable normal PWSD operations, including various PWSD operations described herein.

A target alert recipient verification and registration process 1050 shown in FIG. 8B includes a first process portion 1052 involving downloading and installing/executing a target alert recipient app on an electronic/computing device used by a candidate target alert recipient, and which can serve as an ARD 900. A second process portion 1054 involves verification of whether the one-time verification code sent to the candidate target alert recipient (e.g., by way of an e-mail or an SMS/MMS) has been entered and received by the target alert recipient app. If not, the process remains at the second process portion 1054.

Once the one-time verification code has been entered, a third process portion 1056 communicates a target alert recipient app serial number (S/N) or ID as well as the one-time verification code to the remote server(s) 500, which determine whether the one-time verification code is valid and target alert recipient registration can proceed in a fourth process portion 1060. If not, the process 1050 returns to the second process portion 1054.

If the one-time verification code is valid, a fifth process portion 1062 involves requesting and receiving target alert recipient information, such as at least some of a target alert recipient name; a target alert recipient mailing address: one or more target alert recipient e-mail addresses; one or more target alert recipient telephone numbers, which can include a set of mobile telephone numbers and/or a set of landline telephone numbers; and a target alert recipient login name and password for logging into the set of remote servers 500. A sixth process portion 1064 involves remote server determination of whether particular target alert recipient information is valid, such as by way of sending an e-mail or an SMS MMS message to the target alert recipient under consideration, to which the target alert recipient must respond. If not, the process 1050 returns to the fifth process portion 1062; otherwise, the process 1050 stores the target alert recipient information in the remote database 700 in a seventh process portion 1066.

An eighth process portion 1070 involves remote server determination of whether the registered target alert recipient is performing a login procedure, and a ninth process portion correspondingly involves determining whether an entered login name and password are valid. If not, the process returns to the eighth process portion 1070; otherwise, a tenth process portion 1080 involves associating or linking the target alert recipient under consideration with the appropriate PWSD user in the remote database 700, such as by way of associating target alert recipient information with the ID of the PWSD 100 and/or a PWSD mobile telephone number corresponding to the PWSD user under consideration. Finally, an eleventh process portion 1082 involves defining the target alert recipient under consideration as verified.

Aspects of Representative PWSD User Monitoring/Alert Issuance Processes

Figure 9A:
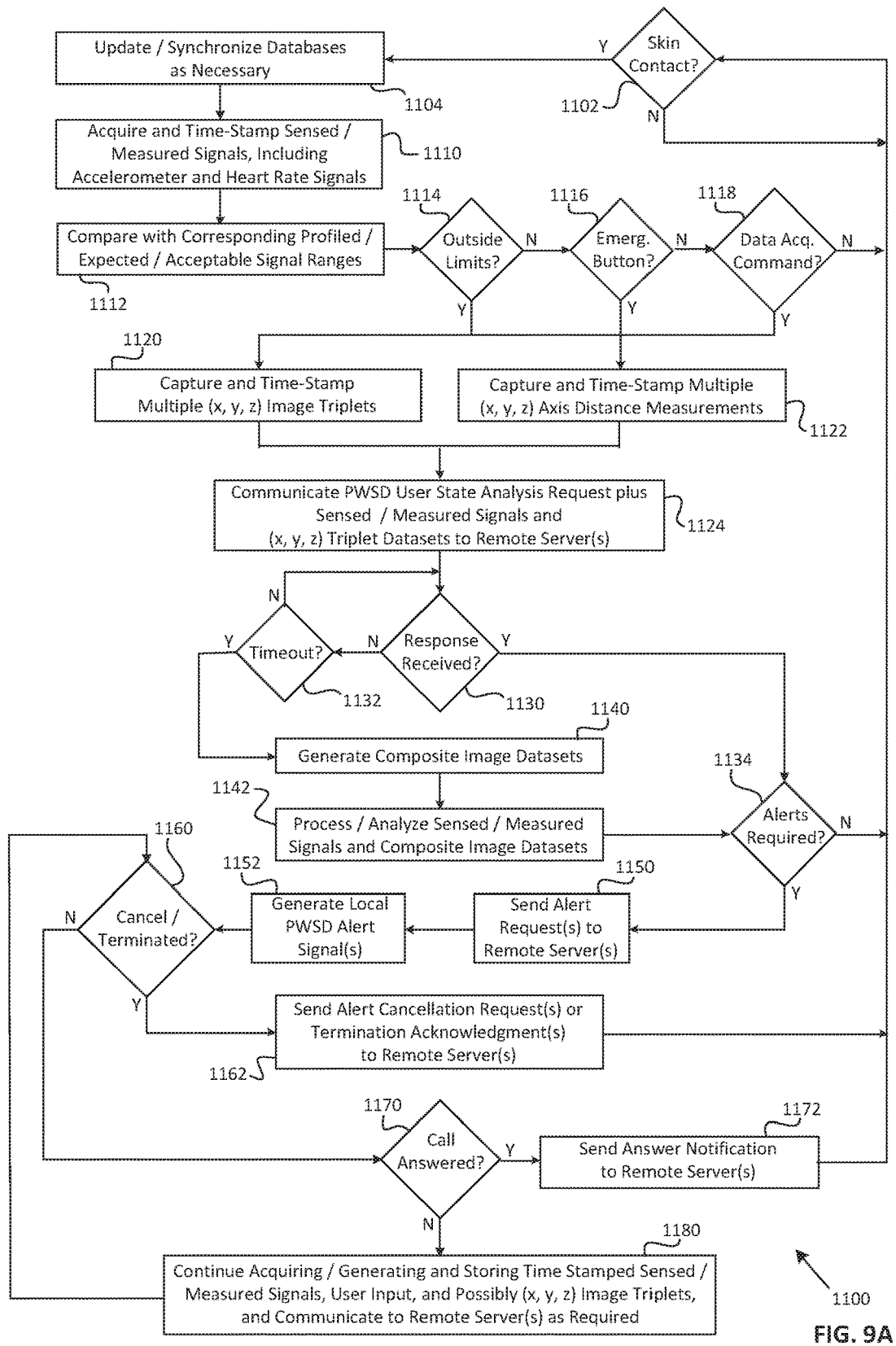
FIG. 9A is a flow diagram of a representative PWSD based or PWSD side monitoring/alert process.
Figure 9B:
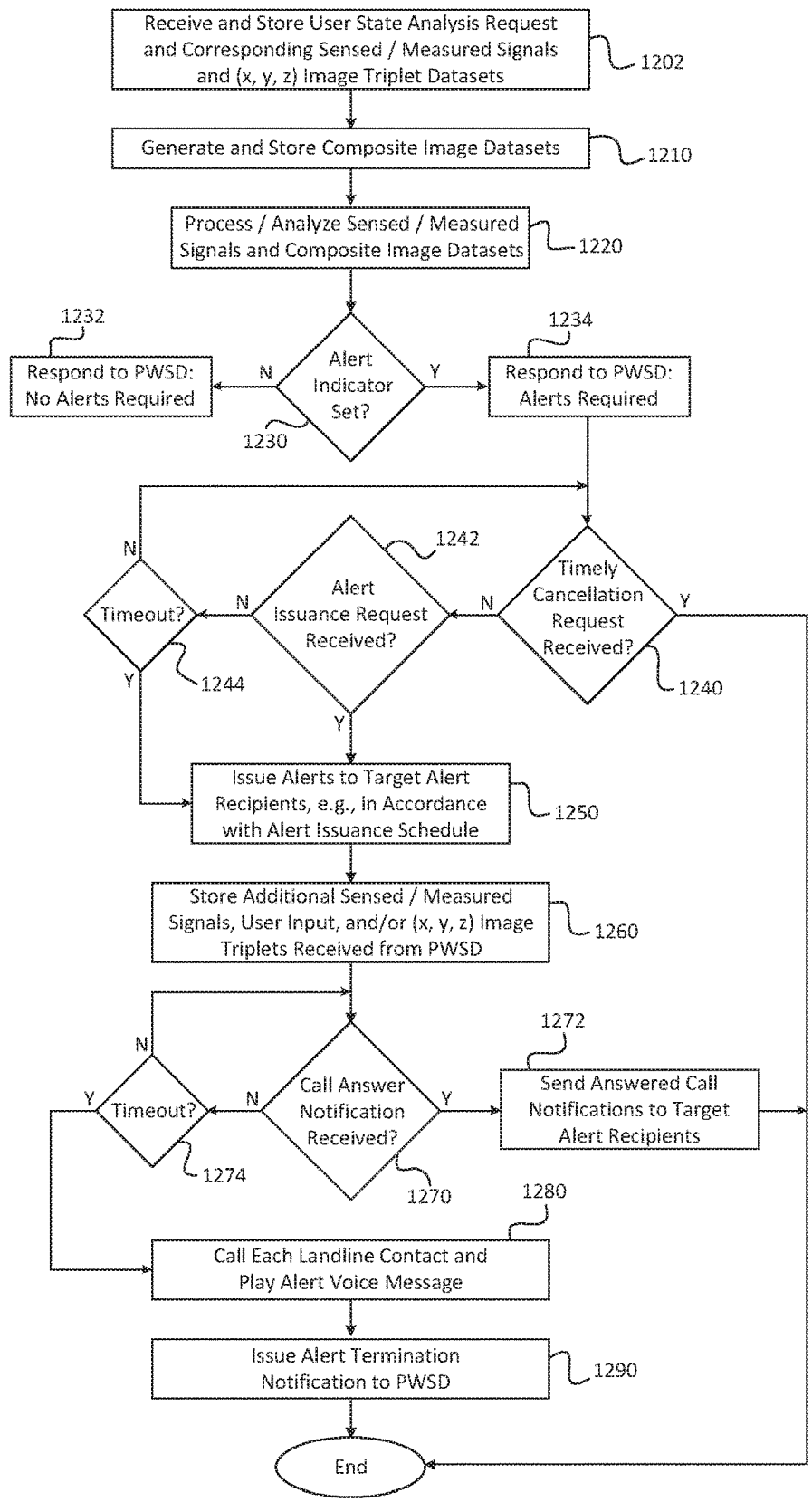
FIG. 9B is a flow diagram of a representative remote server based or remote server side monitoring/alert process.
Figure 9C:
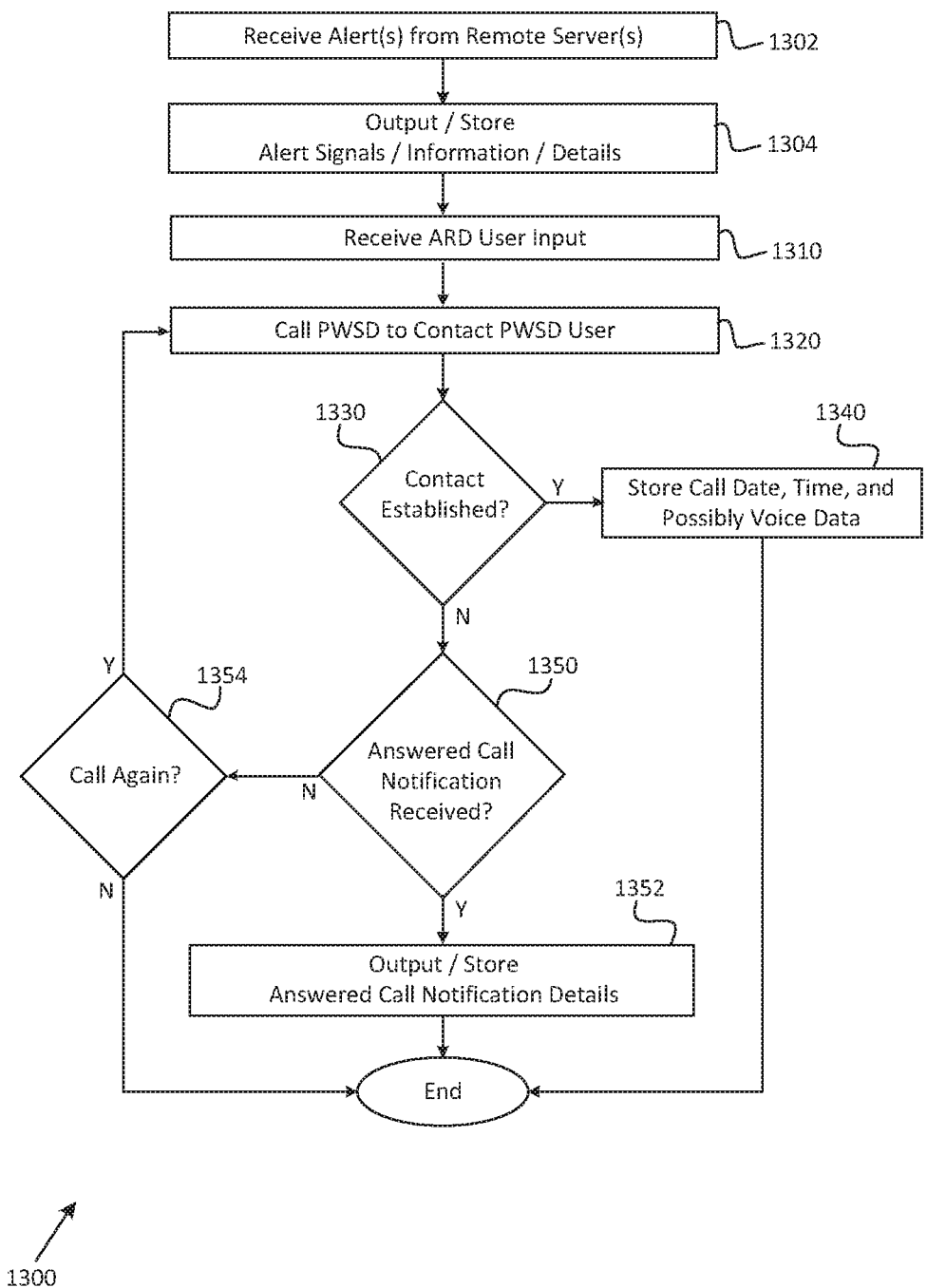
FIG. 9C is a flow diagram of a representative ARD alert process in accordance with an embodiment of the present disclosure.

FIGS. 9A-9C are flow diagrams illustrating portions of representative PWSD user monitoring/alert issuance processes in accordance with an embodiment of the present disclosure. More particularly, FIG. 9A is a flow diagram of a representative PWSD based or PWSD side monitoring/alert process 1100; FIG. 9B is a flow diagram of a representative remote server based or remote server side monitoring/alert process 1200; and FIG. 9C is a flow diagram of a representative ARD alert process 1300 in accordance with an embodiment of the present disclosure.

As indicated in FIG. 9A, a PWSD based monitoring/alert process 1100 includes a first process portion 1102 in which the PWSD 100 monitors or determines whether skin contact exists between the PWSD case 102 and the PWSD user, such as by way of a conventional sensor (e.g., a capacitance sensor, or an electrical continuity sensor). Until or unless skin contact has been established/is maintained, the process 1100 remains at the first process portion 1102. Once skin contact is established, the process 1100 proceeds to a second process portion 1104 involving updating and/or synchronizing the contents of the PWSD's internal database 230 with respect to the remote database 700. The second process portion 1104 can include retrieving or receiving from the remote database 700 typical/expected physiologic data (e.g., heart/pulse rates); a typical/expected activity schedule; and possibly typical/expected GPS coordinate/geofencing data corresponding to the PWSD user, with respect to a current date and one or more time periods or intervals therein.

In a third process portion 1110, the PWSD 100 acquires and time-stamps sensed/measured signals from the set of sensors 142. Such sensed/measured signals can include accelerometer signals, gyroscope signals, heart/pulse rate signals, and/or other signals (e.g., audio signals or temperature signals, or possibly signals received from footwear-based pressure sensors). In a fourth process portion 1112, the PWSD 100 compares the current/most-recent sensed/measured signals with expected/acceptable sensed/measured signal ranges and/or profiled sensed/measured signal ranges for the PWSD user, which are stored in the internal database 230. The expected/acceptable sensed/measured signal ranges can be based upon a population of individuals representative of the PWSD user; or the expected/acceptable sensed/measured signal ranges and/or the profiled sensed/measured signal ranges can be based upon (a) previously sensed/measured signals for this PWSD user; (b) a type of activity (e.g., commuting, work, exercise, or sleep) in which the user is expected to be engaged in view of the current date and/or time of day; and/or (c) other data, such as the PWSD user's current GPS coordinates (e.g., whether the PWSD user is currently indoors or outdoors) or geofencing data.

A fifth process portion 1114 involves determining whether any sensed/measured signals are outside of expected/acceptable limits or boundaries; a sixth process portion 1116 involves determining whether the PWSD user has activated the emergency button 156; and a seventh process portion 1118 involves determining whether any systems or devices external to the PWSD 100 have issued a data acquisition command. If none of the fifth, sixth, and seventh process portions 1114, 1116, 1118 correspond to "yes" or are triggered, the process 1100 returns to the first process portion 1102.

If any of the fifth, sixth, or seventh process portions 1114, 1116, 1118 are triggered, the process 1100 includes an eighth process portion 1120 involving the capture and time-stamping of multiple sets of images, such as multiple (x, y, z) image triplets (e.g., 5 image triplets, captured over a selectable/programmable or predetermined time interval such as approximately 1-10 seconds); and a ninth process portion 1122 involving the capture and time-stamping of multiple corresponding x-axis, y-axis, and z-axis distance measurements (e.g., 5 of such distance measurements, captured over an analogous, corresponding, or identical time interval). A tenth process portion 1124 includes sending a PWSD user state analysis request plus a most-recent sequence of sensed/measured and time-stamped signals, multiple image datasets (e.g., multiple (x, y, z) image triplet datasets) corresponding to the aforementioned captured sets of images, and the aforementioned corresponding (x, y, z) distance measurements to the set of remote servers 500, such that the set of remote servers 500 can determine whether an alert/emergency condition or likely alert/emergency condition exists.

In an eleventh process portion 1130, the PWSD 100 determines whether a response to the PWSD user state analysis request has been received from the remote server(s) 500. If not, a twelfth process portion 1132 involves determining whether a remote server response timeout has been reached. If the remote server response timeout has not been reached, the process 1100 returns to the eleventh process portion 1130. If the PWSD 100 has received a response from the remote server(s) 500, the PWSD 100 determines in a thirteenth process portion 1134 based on the response from the remote server(s) 500 whether the issuance of alerts to target alert recipients is required. If not, the process 1100 returns to the first process portion 1102.

During the eleventh and twelfth process portions 1130, 1132, the PWSD 100 is effectively waiting for remote server confirmation of whether an alert/emergency condition exists. Such confirmation requires that the remote server(s) 500 actually received from the PWSD 100 the PWSD user state analysis request, the corresponding sensed/measured signals, the (x, y, z) image triplet datasets generated as a result of the eight process portion 1120, and the distance measurements generated as a result of the ninth process portion 1122. If in the twelfth process portion 1132 the remote server response timeout has been reached, in fourteenth process portion 1140 the PWSD 100 itself generates multiple composite image datasets from the multiple sets of images captured as a result of the eighth process portion 1120; and in a fifteenth process portion 1142, the PWSD 100 itself processes/analyzes most-recent sensed/measured signals, and processes/analyzes the most-recently generated composite image datasets and the corresponding most-recently generated distance signals to determine whether an alert/emergency condition exists. Representative aspects of the fourteenth process portion 1140 are described in detail below with reference to FIGS. 10A-10E; and representative aspects of the fifteenth process portion 1142 are described in detail below with reference to FIGS. 11A-11C. Following the fifteenth process portion 1142, the process 1100 proceeds to the thirteenth process portion 1134.

If during the thirteenth process portion 1134 the PWSD 100 determines that an alert/emergency condition exists, a sixteenth process portion 1150 includes PWSD issuance of an alert request to the remote server(s) 500. In various embodiments, the alert request includes or is an SMS/MMS message. A seventeenth process portion 1152 includes PWSD generation/output of local PWSD alert signals, for instance, PWSD output of an audio signal sequence (e.g., a series of beeps) and/or PWSD generation of vibratory signals, which can direct the PWSD user's attention to the fact that the PWSD 100 has issued an alert request to the remote server(s) 500.

An eighteenth process portion 1160 includes PWSD determination of whether (a) the PWSD user has indicated in a timely manner (e.g., within approximately 5-30 seconds, or about 10-20 seconds) that alert cancellation is required (e.g., by pressing one or more PWSD buttons in accordance with an alert cancellation sequence); or (b) an alert termination notification has been received from the remote server(s) 500, as further detailed below. If so, a nineteenth process portion 1162 includes PWSD issuance of a corresponding alert cancellation request or alert termination acknowledgment to the remote server(s) 500, after which the process 1100 returns to the first process portion 1100.

If in the eighteenth process portion 1160 an alert cancellation has not been timely generated and an alert termination has not occurred, in a twentieth process portion 1170 the PWSD 1100 determines whether an incoming call from a target alert recipient has been answered by the PWSD user. If so, the PWSD 100 sends a call answer notification to the remote server(s) 500 in a twenty-first process portion 1172. Otherwise, in a twenty-second process portion 1180, the PWSD 100 continues to acquire/generate and store additional time-stamped sensed/measured signals, and possibly one or more additional sets of images (e.g., (x, y, z) image triplets) and corresponding distance measurements. As part of the twenty-second process portion 1180, the PWSD 100 can communicate such additional sensed/measured signals, additional sets of captured images (e.g., (x, y, z) image triplets), and distance measurements to the remote server(s) 500. Following the twenty-second process portion 1180, the process 1100 returns to the eighteenth process portion 1160.

Figure 10A:
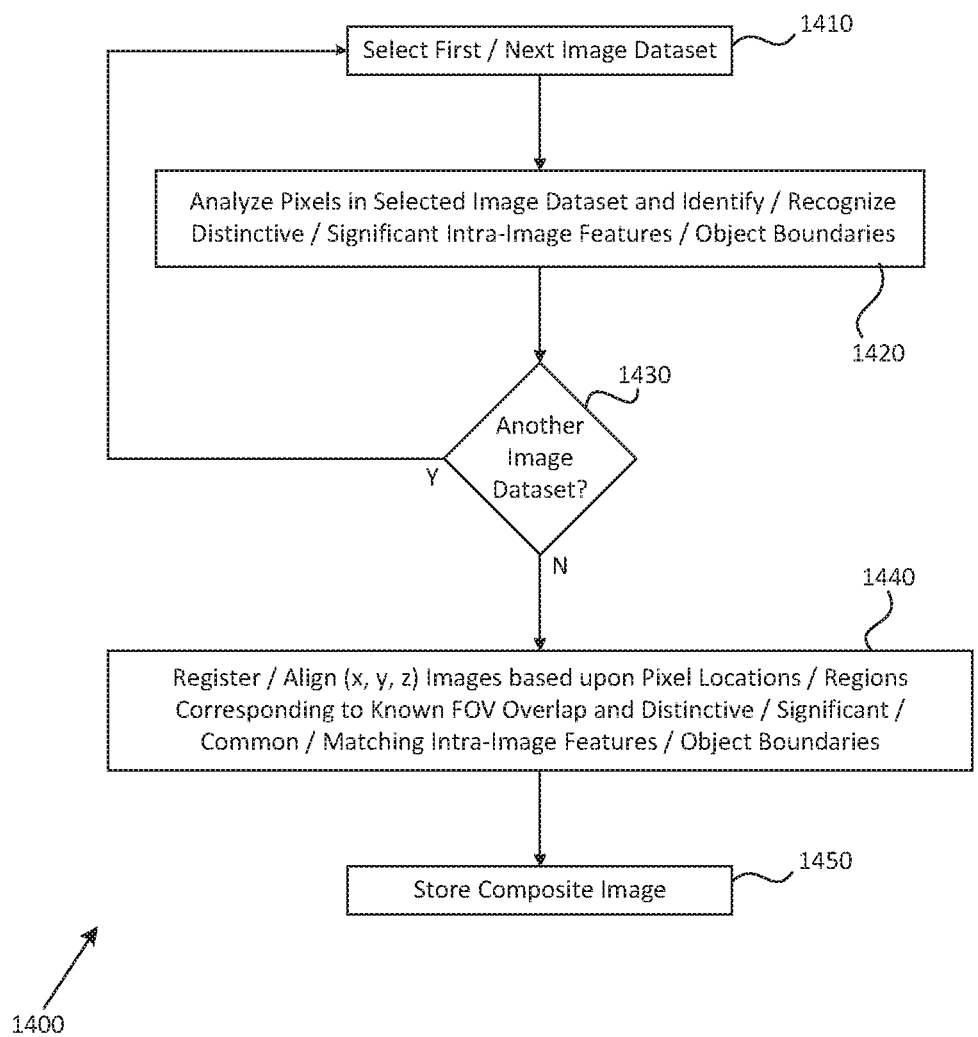
FIG. 10A is a flow diagram of a representative composite image generation process which is performable by a PWSD 100 or the set of remote servers 500 in accordance with an embodiment of the present disclosure.
Figure 11A:
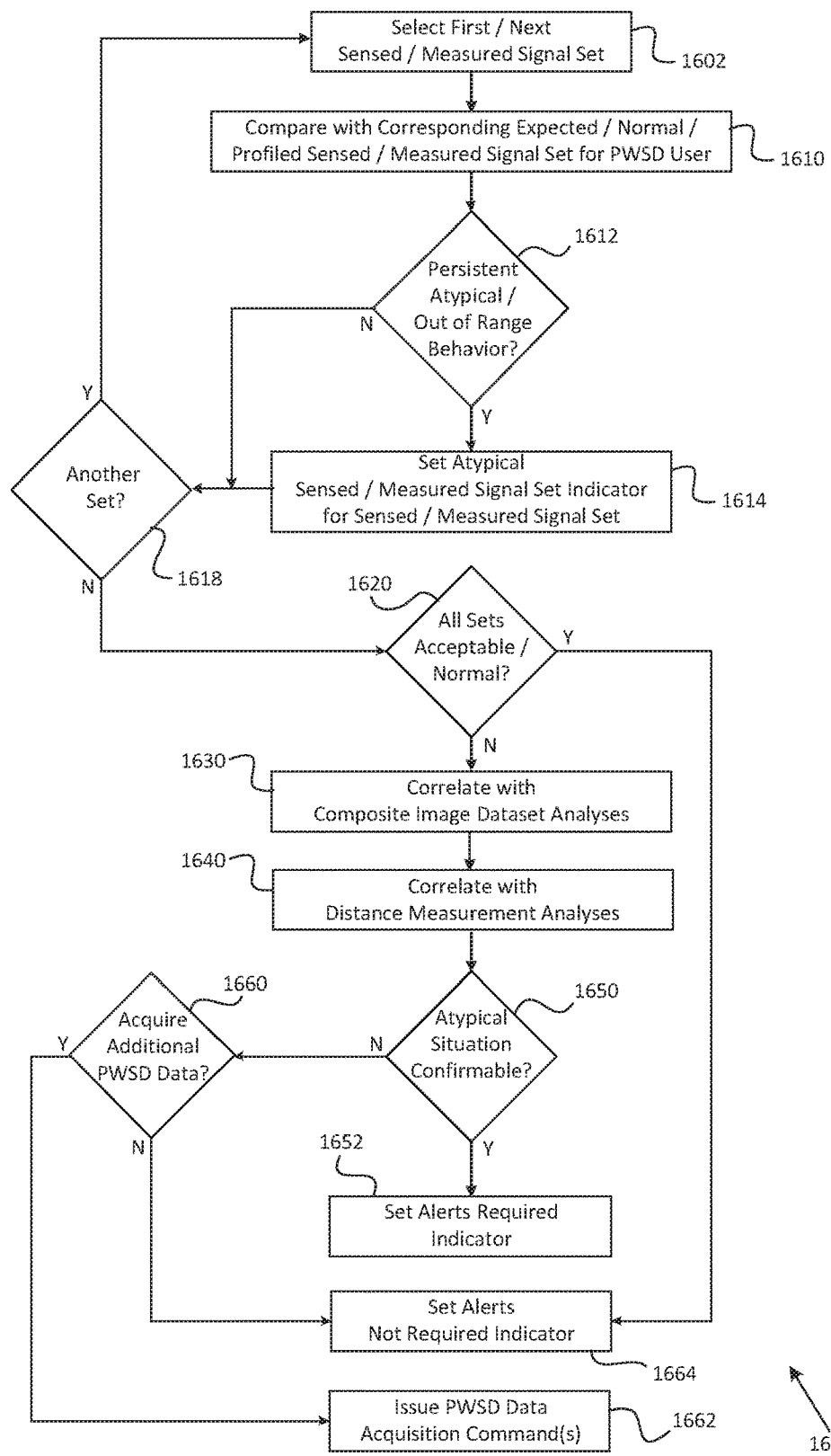
FIG. 11A is a flow diagram of a representative sensed/measured signal sequence analysis process.

As indicated in FIG. 9B, a remote server based monitoring/alert process 1200 includes a first process portion 1202 in which the set of remote server 500 receives a PWSD user state analysis request and corresponding sensed/measured signals, multiple most-recent captured image datasets (e.g., (x, y, z) image triplet datasets), and multiple corresponding distance measurements from a given PWSD under consideration with respect to FIG. 11A. In a second process portion 1210, the set of remote server 500 generates composite images corresponding to the image datasets received. In a third process portion 1220, the remote server(s) 500 process/analyze the most-recent sensed/measured signals received from the PWSD 100 under consideration, along or in association with processing/analyzing the composite images and corresponding distance measurements. Representative aspects of the second process portion 1210 are described in detail below with reference to FIGS. 10A-10E; and representative aspects of the third process portion 1220 are described in detail below with reference to FIGS. 11A-11C.

In a fourth process portion 1230, the set of remote servers 500 determines whether an alert indicator has been set. If not, the set of remote server 500 sends an "alerts not required" response to the PWSD 100 in a fifth process portion 1232. Otherwise, the set of remote server 500 sends an "alerts required" response to the PWSD 100 in a sixth process portion 1234.

The set of remote server 500 then determines in a seventh process portion 1240 whether a timely cancellation request has been received from the PWSD 100 under consideration; if so, the process 1200 ends. Otherwise, the set of remote server 500 determines whether an alert issuance request has been received from the PWSD 100 in an eighth process portion 1242. If not, the remote server(s) 500 determine whether a PWSD response timeout period has been reached in a ninth process portion 1244.

After receipt of an alert issuance request from the PWSD 100 in the eight process portion 1242, or after the PWSD response timeout period has been reached in the ninth process portion 1244, in a tenth process portion 1250 the remote server(s) 500 issue alerts to at least some or each of the target alert recipients associated or linked with the PWSD user in the remote database 700. The alerts can be issued in accordance with an alert issuance schedule, for instance, an alert can be automatically sent to each target alert recipient associated with the PWSD user approximately every 10-60 seconds (e.g., every 10-30 seconds) on a recurring/repeated or ongoing basis.

In an eleventh process portion 1260, the remote server(s) 500 can store any additional sensed/measured signals, captured sets of images (e.g., (x, y, z) image triplets), and distance measurements received from the PWSD 100.

In a twelfth process portion 1270, the set of remote servers 500 determines whether a call notification has been received from the PWSD 100, indicating that the PWSD user has, by way of their PWSD 100, answered or responded to an incoming telephone call from one of the target alert recipients to whom alerts have been sent. If so, in a thirteenth process portion 1272 the set of remote server 500 sends a series of answered call notifications to each target alert recipient (e.g., other than the target alert recipient that successfully reached the PWSD user by way of an incoming call that the PWSD user answered with their PWSD 100) indicating that voice contact has been successfully established between the PWSD user and a given target alert recipient. Following the thirteenth process portion 1272, the process 1200 can end.

If a call notification has not yet been received, the set of remote server 500 determines in a fourteenth process portion 1274 whether a call notification timeout period has been reached. In a number of embodiments, this timeout period can be, for instance, approximately 10-60 minutes, during which time the set of remote server 500 can continue to repeatedly send alerts to target alert recipients. If the call notification timeout period has not been reached, the process 1200 returns to the twelfth process portion 1270. Once the call notification timeout period has been reached, in a fifteenth process portion 1280 the set of remote servers 500 calls each mobile and/or landline contact number for each target alert recipient associated with the PWSD user, and plays an alert/emergency voice message when the call to the target alert recipient is answered. Following the fifteenth process portion 1280, the set of remote servers 500 can issue an alert termination notification to the PWSD 100, after which the process 1200 can end.

As indicated in FIG. 9C, a representative ARD alert process 1300 includes a first process portion 1302 involving ARD receipt of an alert from the set of remote server 500; and a second process portion 1304 involving ARD presentation/output and storage of alert signals, information, and details. The second process portion 1304 can include ARD generation or output of audio signals (e.g., beeps, and/or the playback of recorded PWSD audio data); and ARD presentation of text, graphics, and/or images on an ARD display device (which can include the presentation of the PWSD user's telephone number, and possibly portions of a PWSD captured image or a corresponding composite image).

In a third process portion 1310, the target alert recipient's ARD receives user input by way of an ARD user input device, such as a touch screen display; and in a fourth process portion 1320 the ARD 900 calls the PWSD 100 corresponding to the PWSD user identified in the alert.

In a fifth process portion 1330, the target alert recipient and/or their ARD 900 determines whether voice contact has been established with the PWSD user under consideration. If so, in a sixth process portion 1340 the ARD 900 can store call details such as a call date, time, duration, and possibly voice data, after which the process 1300 can end. If voice contact has not been established with the PWSD user, in a seventh process portion 1350 the ARD 900 can determine whether an answered call notification has been received from the set of remote server 500. If so, the ARD 900 can output/present answered call notification details in an eighth process portion 1352, such as the identity of another target alert recipient that successfully managed to establish a voice call with the PWSD user, and the time, date, and duration of the voice call. If in association with the seventh process portion 1350 an answered call notification has not been received, in a ninth process portion 1354 the target alert recipient using the ARD 900, or the ARD 900 itself, can determine whether to re-dial the PWSD user up to a selectable/programmable or predetermined number of re-dial attempts (e.g., approximately 10-50 re-dial attempts). If so, the process 1300 can return to the fourth process portion 1320; otherwise, the process 1300 can end.

Aspects of Representative Image Stitching Processes

FIGS. 10A-10E illustrate representative aspects of composite image generation in accordance with an embodiment of the present disclosure. More particularly, FIG. 10A is a flow diagram of a representative composite image generation process 1400, which is performable by a PWSD 100 or the set of remote server 500; FIGS. 10B-10D illustrate a representative image captured along a PWSD x-axis (i.e., a representative x-axis image as defined herein) 1510x, a representative image captured along the PWSD y-axis (i.e., a representative y-axis image as defined herein) 1510y, and a representative image captured along the PWSD z-axis (i.e., a representative z-axis image as defined herein) 1510z, which collectively form an (x, y, z) image triplet 1500; and FIG. 10E illustrates a representative composite image 1550 generated from this (x, y, z) image triplet 1500 in accordance with an embodiment of the present disclosure.

As indicated in FIG. 10A, a representative composite image generation process 1400 includes a first process portion 1410 involving selecting a first/next x-axis, y-axis, or z-axis image dataset corresponding to an (x, y, z) image triplet under consideration; a second process portion 1420 involving analyzing pixels within the selected image dataset to identify/recognize distinctive/significant intra-image features and/or object boundaries within the selected image dataset; and a third process portion 1430 involving determining whether another image dataset of the (x, y, z) image triplet requires consideration.

A fourth process portion 1440 involves registering the x, y, and z images of the (x, y, z) image triplet under consideration, based upon pixel locations/regions corresponding to known FoV overlap and/or distinctive/significant/common/matching intra-image features and/or object boundaries to thereby produce a composite image. The fourth process portion 1440 can include one or more conventional image registration processes, procedures, or techniques, such as a continuous or quasi-continuous optimization technique (e.g., a gradient descent or other technique), in a manner readily understood by individuals having ordinary skill in the relevant art.

A fifth process portion 1450 includes storing the composite image 1550.

As an illustrative example to further aid understanding, in association with the process 1400 of FIG. 10A, the representative x-axis image dataset is processed/analyzed to identify a plurality of distinct pixels therein corresponding to intra-image features, e.g., borders or boundaries within the x-axis image. Similarly, the representative y-axis image dataset is processed/analyzed to identify a plurality of distinct pixels therein corresponding to intra-image features, e.g., borders or boundaries within the y-axis image. An individual having ordinary skill in the relevant art will understand that due to the aforementioned FoV overlap, some of the intra-image features identified in the y-axis image match or are counterparts to intra-image features identified in the x-axis image. Additionally, the representative z-axis image dataset is processed/analyzed to identify a plurality of distinct pixels therein corresponding to intra-image features, e.g., borders or boundaries within the z-axis image. An individual having ordinary skill in the relevant art will further understand that as a result of the aforementioned FoV overlap, some of the intra-image features identified in the z-axis image match or are counterparts to intra-image features identified in the x-axis image and the y-axis image.

A representative composite image 1550 generated by the process 1400 of FIG. 10A as a result of registering the x-axis image 1510x, the y-axis image 1510y, and the z-axis image 1510z in accordance with expected/predetermined/known FoV overlap and intra-image feature commonality/matching is shown in FIG. 10E.

Individuals having ordinary skill in the art will understand that image stitching can be performed on image doublets in a manner analogous to that described above to generate corresponding composite images.

Aspects of Representative PWSD Information Processing and Alert Processes

Figure 11B:
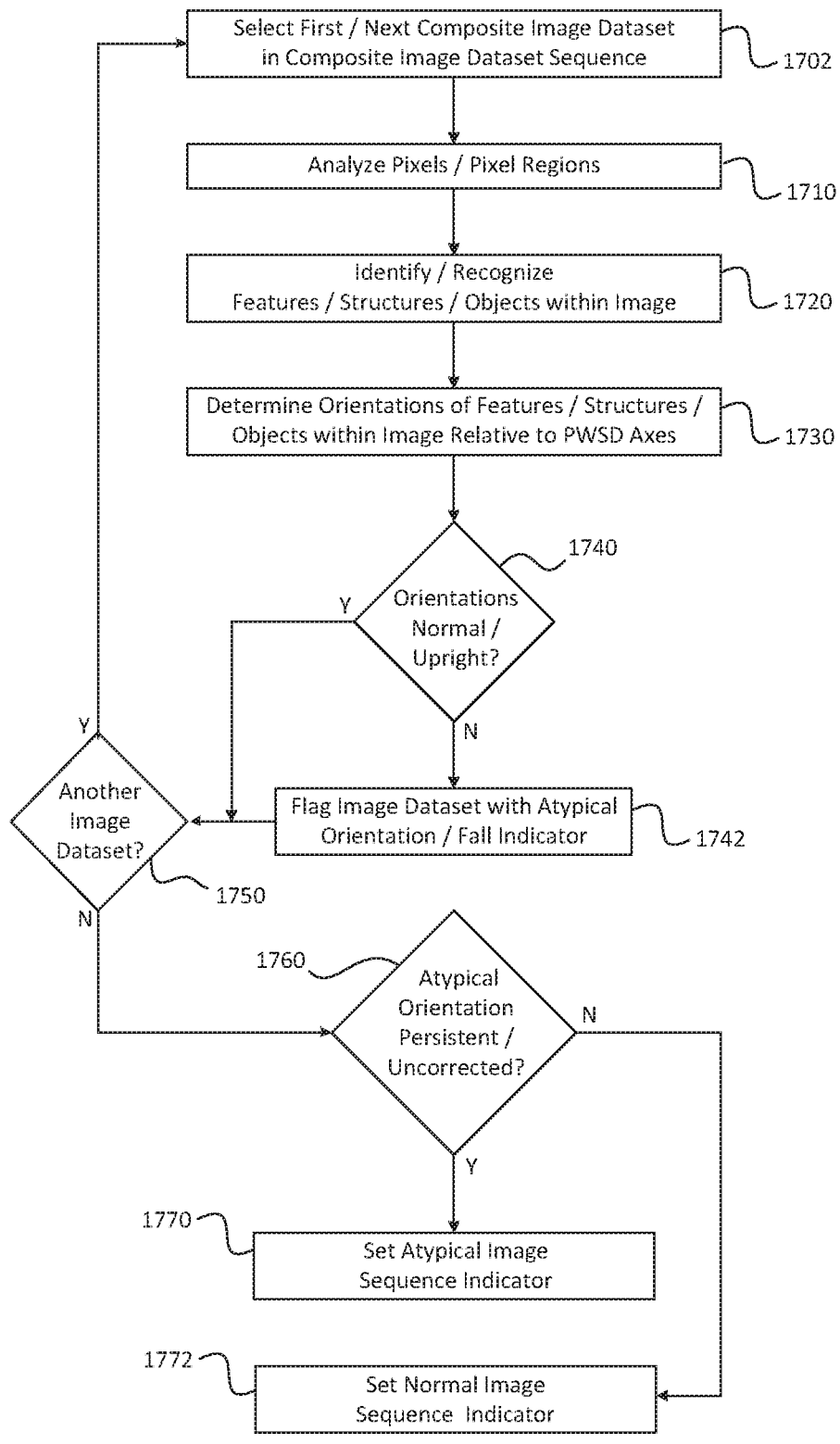
FIG. 11B is a flow diagram of a representative composite image dataset sequence analysis process in accordance with an embodiment of the present disclosure.
Figure 11C:
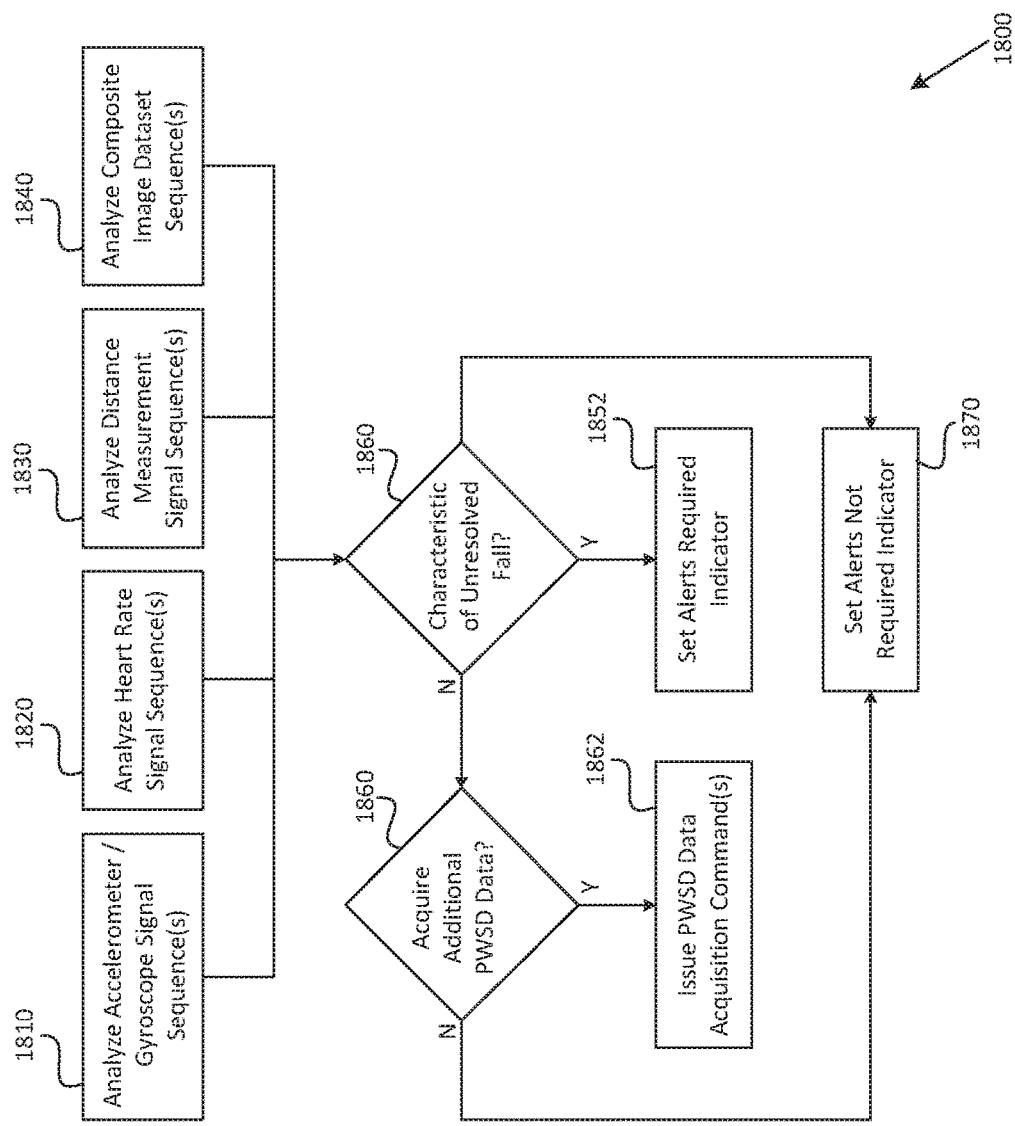
FIG. 11C is a flow diagram of a representative fall detection process in accordance with an embodiment of the present disclosure.

FIGS. 11A-11C illustrate representative aspects of interrelated, cooperative, or coordinated sensed/measured signal, image dataset, and measured distance signal processing/analyses in accordance with an embodiment of the present disclosure. More particularly, FIG. 11A is a flow diagram of a representative sensed/measured signal sequence analysis process 1600; FIG. 11B is a flow diagram of a representative composite image dataset sequence analysis process 1700; and FIG. 11C is a flow diagram of a representative fall detection process 1800 in accordance with an embodiment of the present disclosure. The processes of FIGS. 11A-11C are performable by a PWSD 100 or the set of remote server 500.

In FIG. 11A, the sensed/measured signal analysis process 1600 includes a first process portion 1602 involving the selection of a first or next set of sensed/measured signals for consideration, such as a set of accelerometer signals, a set of gyroscope signals, a set of GPS signals, geofencing map data a set of heart/pulse rate signals, and/or other signals (e.g., a set audio signals or a set of temperature signals). A second process portion 1610 involves comparison of the currently selected set of sensed/measured signals with corresponding expected/normal measured signals for the PWSD user, in view of (a) a population of individuals representative of the PWSD user, or (b) profiled or previously sensed/measured and stored signals for the PWSD user, possibly in view of the current date, time of day, and the PWSD user's expected activity schedule. A third process portion 1612 involves determining whether the currently selected set of sensed/measured signals exhibits atypical, out of range, or abnormal behavior for more than a given period of time, such as a number of seconds (e.g., approximately 5-30 seconds, or about 10-20 seconds) or minutes (e.g., about 1-2 minutes) depending upon the type of sensed/measured signals currently under consideration. If so, the set of sensed/measured currently under consideration is flagged as atypical in a fourth process portion 1614. After the fourth process portion 1614, or after the third process portion 1612 in the event that the currently selected set of sensed/measured signals exhibits typical/expected/normal behavior, a fifth process portion 1618 considers whether another set of sensed/measured signals requires consideration. If so, the process 1600 returns to the first process portion 1602.

After the fifth process portion 1618, a sixth process portion 1620 involves determining whether all sets of sensed/measured signals considered exhibited typical/expected/normal behavior. If so, the process 1600 sets an "alerts not required" indicator in a twelfth process portion 1664. If one or more sets of sensed/measured signals considered exhibited atypical/unexpected/abnormal behavior, a seventh process portion 1630 involves analyzing corresponding composite image datasets and correlating the composite image dataset analysis with such atypical/unexpected/abnormal behavior, for instance, in a manner indicated in FIG. 11B; and an eighth process portion 1640 involves analyzing corresponding distance measurements and correlating the distance measurements with the atypical/unexpected/abnormal sensed/measured signal behavior. Distance measurements can indicate an atypical/unexpected/abnormal situation such as an unresolved fall when a distance to a nearest object away from the PWSD 100 along the PWSD's x-axis, y-axis, or z-axis has suddenly decreased to less than a predetermined distance, such as approximately 0-10 cm.

A ninth process portion 1650 involves determining whether an atypical/unexpected/abnormal situation can be confirmed, such as when at least some sensed/measured signals and at least one of the composite image datasets and the distance measurements indicate that an atypical/unexpected/abnormal/emergency situation exists. If so, a tenth process portion 1652 involves setting an "alerts required" indicator. If an atypical/unexpected/abnormal situation cannot be confirmed, an eleventh process portion 1660 involves determining whether additional PWSD data would be useful or is required for making such confirmation, for instance, additional sensed/measured signals, additional composite images, and/or additional distance measurements. If so, a thirteenth process portion 1660 involves issuing a PWSD data acquisition command. Otherwise, the process 1600 proceeds to the twelfth process portion 1664 and sets the "alerts not required" indicator.

In FIG. 11B, the composite image analysis process 1700 includes a first process portion 1702 involving selecting a first or next composite image dataset or composite image dataset sequence for consideration; and a second process portion 1710 involving analyzing pixels/pixel regions within the selected composite image dataset(s). A third process portion 1720 involves identifying/recognizing particular features, shapes, structures, and/or objects within the composite image dataset(s) under consideration. The third process portion 1720 can include automatically identifying/recognizing the outline(s) and/or shape(s) of one or more types of structures or objects in the corresponding composite image(s) by way of a set of image processing algorithms, which can be based upon conventional image analytics/object recognition/object classification/visual information analysis/image content searching algorithms, possibly in association with one or more machine learning algorithms, as implemented by way of program instructions/software, possibly aided by knowledge of whether the PWSD user is in an expected environment in accordance with their profiled schedule (e.g., an hourly schedule) in view of the current date and time, and/or whether the PWSD user is indoors or outdoors as indicated by (a) their GPS coordinates and/or (b) audio information in an audio clip captured by the PWSD 100 (e.g., by way of the PWSD's microphone 155) and which is associated or linked (e.g., temporally associated) with the composite image(s) under consideration. Identified/recognized shapes outline(s)/shape(s) can correspond to physical objects or infrastructure in the PWSD user's current or most-recent environment, such as one or more buildings, one or more pillars or structural columns or supports; a set of sign posts/signs; one or more doorways; a number or array of windows or glass panels; a gate; a fence; a corridor or alley; one or more other individuals; one or more animals; one or more trees; the sky; the sun or moon; a roadway; a curb; roadway and/or curb related markings; a sidewalk; a bridge; a set of motorized vehicles such as one or more automobiles, trucks, and/or motorcycles; bicycles; one or more desks, counters, tables, and/or chairs; one or more display or television monitors; a ceiling; artificial lighting or a set of artificial light sources; and/or other environmental objects or infrastructure.

A fourth process portion 1730 involves determining the orientation(s) of one or more identified/recognized features, structures, and/or objects within the composite image(s) relative to the PWSD's x-axis, y-axis, and/or z-axis; and a fifth process portion 1740 involves determining whether such orientations are normal/expected/upright, thereby indicating that the PWSD user is in a normal/expected/upright orientation. The fourth and/or fifth process portions 1730, 1740 can involve one or more automated techniques utilized in association with the third process portion 1720. If the orientation(s) of one or more identified/recognized features, structures, and/or objects are not or are not likely normal/ expected/upright, a sixth process portion 1742 flags the presently analyzed composite image dataset(s) with an atypical/fall indicator. After the sixth process portion 1742, or after the fifth process portion 1740 in the event that feature, structure, and/or object orientations within the presently analyzed composite image(s) appear normal/expected/ upright, a seventh process portion 1750 involves determining whether an additional composite image dataset/dataset sequence requires consideration. If so, the process 1700 returns to the first process portion 1702.

An eighth process portion 1760 involves determining whether the analyzed series of composite image datasets indicates that the PWSD 100 has been in atypical/unexpected orientation for a given period of time, for instance, approximately 5-30 seconds (e.g., about 10-20 seconds), and this atypical/unexpected orientation has not returned to a typical/expected or approximately typical/expected orientation. If so, a ninth process portion 1770 sets an atypical image sequence indicator; otherwise, a tenth process portion 1772 sets a normal image sequence indicator.

In FIG. 11C, a fall detection process 1800 includes (a) a first process portion 1810 involves analyzing accelerometer and/or gyroscope signal sequences; (b) a second process portion 1820 involves analyzing heart/pulse rate signal sequences; (c) a third process portion 1830 involves analyzing distance measurement signal sequences; and (d) a fourth process portion 1840 involves analyzing composite image dataset sequences. The first through fourth process portions 1810-1840 can be performed in parallel or concurrently. A fifth process portion 1850 involves determining whether the results of multiple or each of the first through fourth process portions 1810-1840 are characteristic of a sudden and unresolved PWSD user fall. If so, a sixth process portion 1852 involves setting an "alerts required" indicator. A seventh process portion 1860 involves determining whether additional PWSD data would be useful or is required in order to accurately determine whether a sudden and unresolved PWSD user fall has occurred, for instance, if two or fewer of the results from the first through the fourth process portions 1810-1840 are characteristic of a sudden and unresolved PWSD user fall. If so, an eighth process portion 1862 involves issuing a set of PWSD data acquisition commands. Otherwise, a ninth process portion 1870 involves setting an "alerts not required" indicator.

Further Aspects of Representative PWSD User Monitoring

Figure 12A:
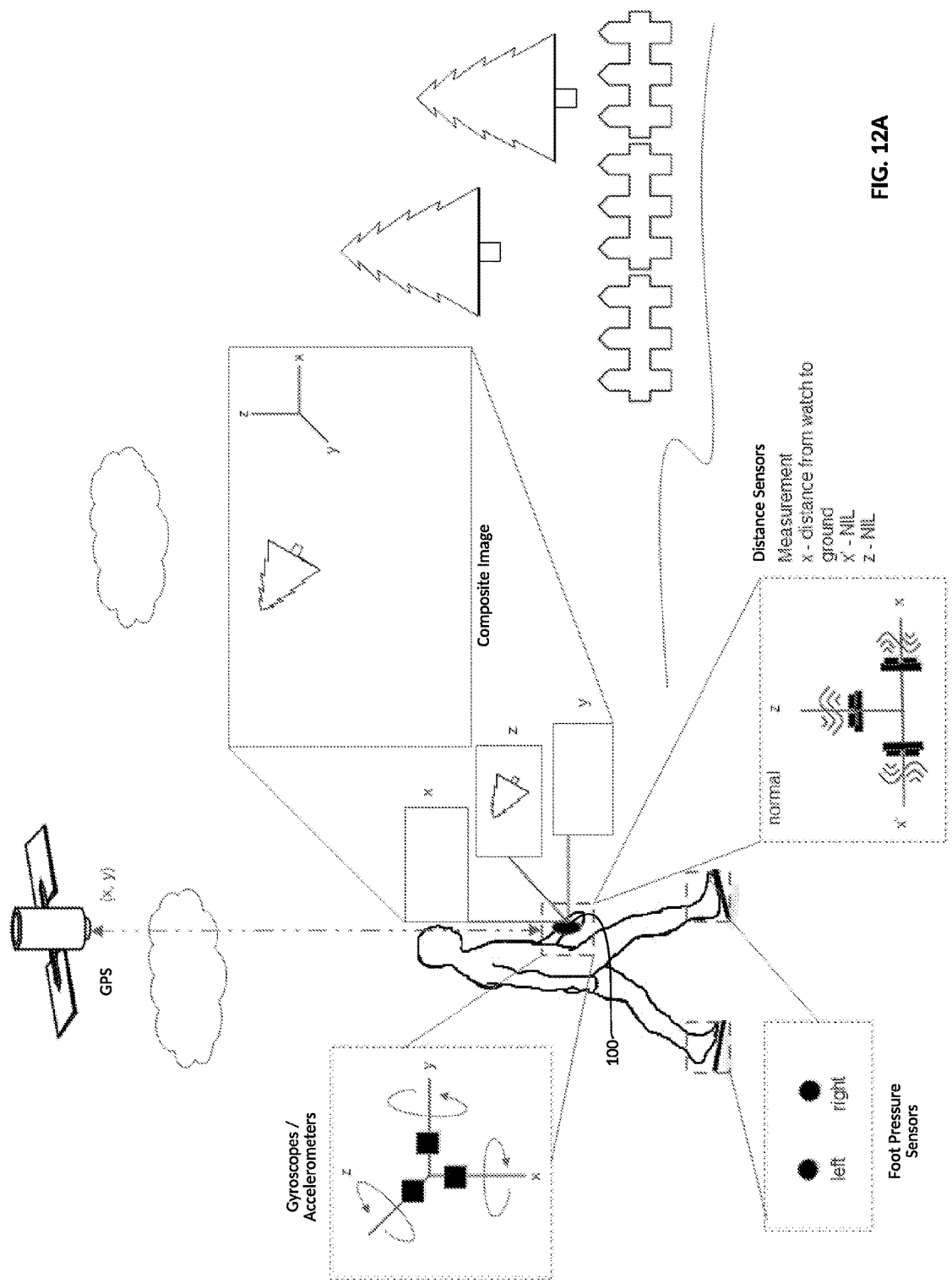
FIGS. 12A-12D illustrate representative aspects of PWSD user monitoring in accordance with particular embodiments of the present disclosure.

FIGS. 12A-12D illustrate additional representative aspects of PWSD user monitoring in accordance with particular embodiments of the present disclosure. As indicated in FIG. 12A, during normal, typical, or routine PWSD user activities such as walking, the sensors 142 carried by and/or configured for communication with the PWSD 100 generate corresponding (x, y, z) gyroscope/accelerometer signals; a set of (x, z) distance/proximity sensors 145 generate (x, z) or (x, x', z) distance measurements; and a set of footwear-based sensors (e.g., pressure sensors disposed in PWSD user footwear beneath the PWSD user's feed) generate left and right foot pressure signals. The PWSD 100 can be configured for wireless signal communication with a footwear pressure sensor communication unit that is also carried by the PWSD user footwear, in a manner readily understood by individuals having ordinary skill in the relevant art. Additionally, a set of cameras 130 carried by the PWSD 100, such as x-axis, y-axis, and z-axis cameras 130$x,y,z$, can periodically capture x-axis, y-axis, and z-axis images of portions of the PWSD user's environmental surroundings. The PWSD 100 can generate composite images from individual images having spatially overlapping regions, and which are temporally associated or linked with each other (e.g., as a result of being captured at the same, essentially the same, or nearly the same time).

In some embodiments, the PWSD 100 can process or analyze signals output by the gyroscopes/accelerometers and the foot pressure sensors to determine whether the PWSD 100 is being displaced in a generally regular, repeating, and/or rhythmic pattern, such as a result of PWSD user arm swing during walking or running. If so, the PWSD 100 can control the set of cameras 130 to capture images synchronized or approximately synchronized with such generally regular, repeating, and/or rhythmic PWSD displacement (e.g., corresponding to a PWSD position on the user's arm at the front, bottom, or rear of an arm swing), in a manner readily understood by individuals having ordinary skill in the relevant art. Consequently, the PWSD 100 can capture multiple sets of images at different times corresponding or approximately corresponding to a particular detectable PWSD user arm position during such generally regular, repeating, and/or rhythmic PWSD displacement.

Figure 12B:
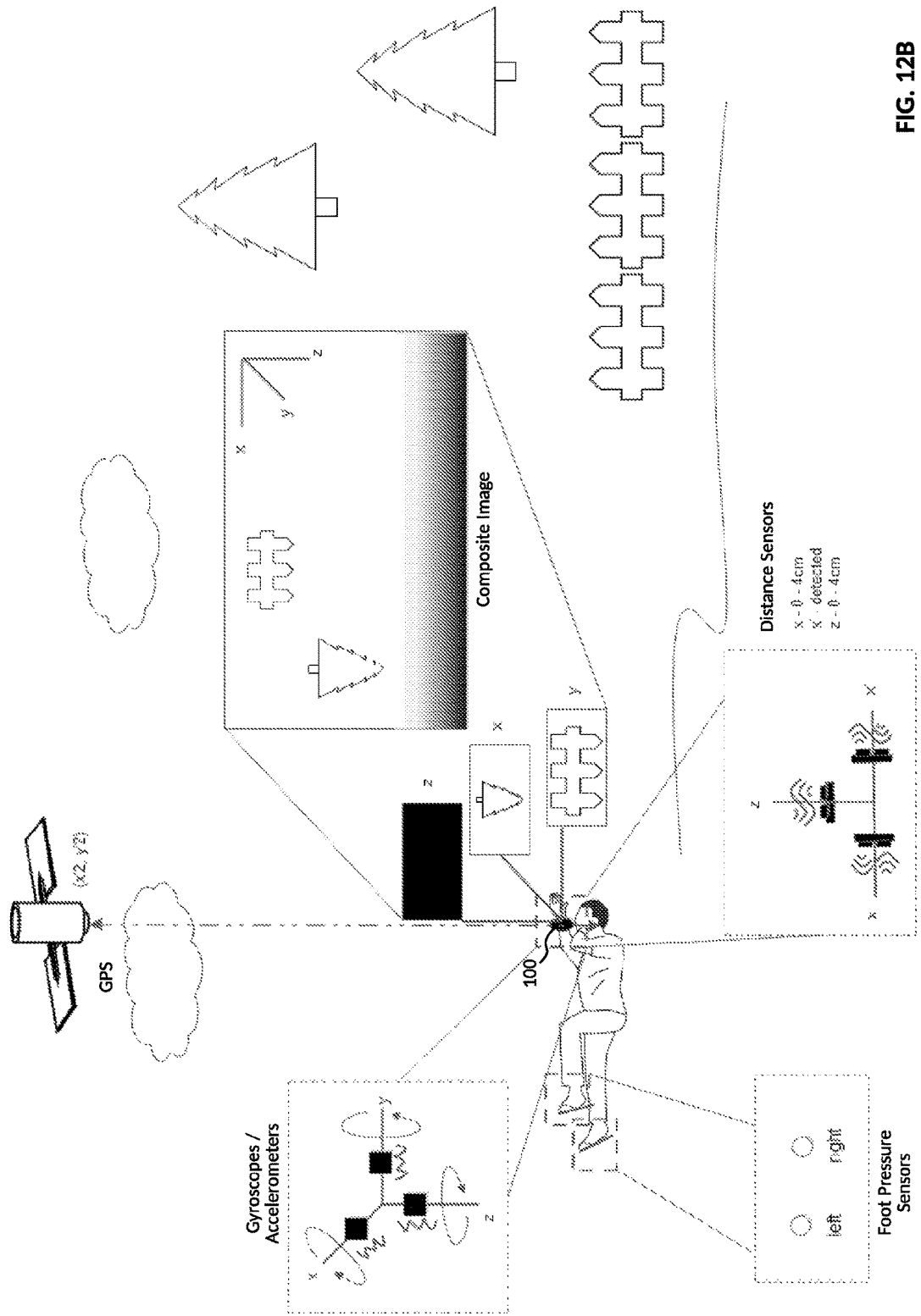
Figure 12C:
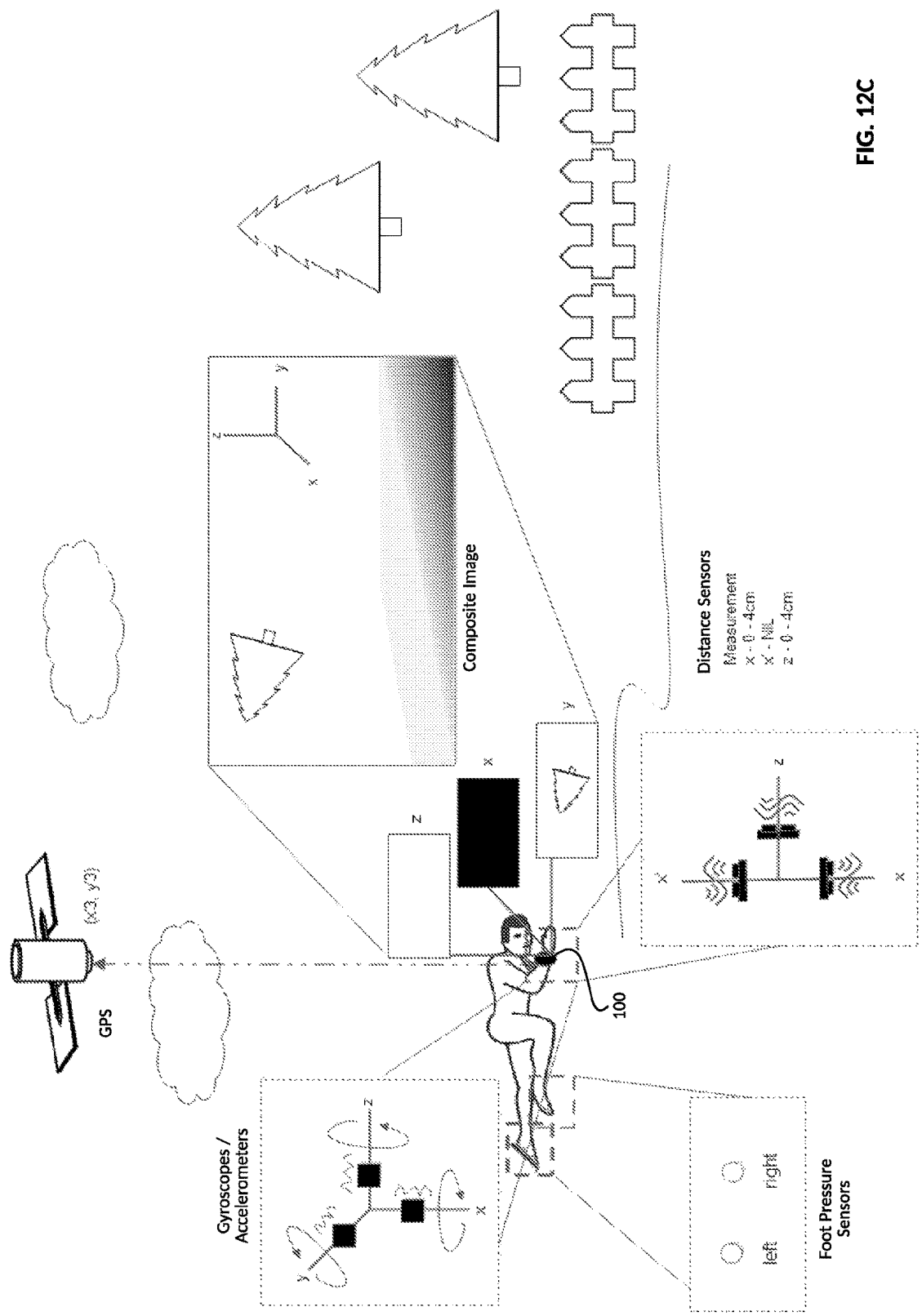

As indicated in FIG. 12B, in the event that the PWSD user experiences a fall that orients them in a first fallen position, or as indicated in FIG. 12C in the event that the PWSD user experiences a fall that orients them in a second fallen position, the signals output by the gyroscopes/accelerometers, the distance/proximity sensors 145, and the foot pressure sensors will suddenly, significantly, or dramatically change compared to their values while the PWSD user maintained a normal upright position such as shown in FIG. 12A. More particularly, the gyroscope/accelerometer signals will indicate that a shock or impact has occurred; the distance/proximity sensors 145 will typically generate one or more distance measurements indicating that the PWSD 100 is near or adjacent to the ground; and the foot pressure sensor signals will typically indicate lower and less frequent pressure values. Moreover, the images captured by the cameras 130$x,y,z$ and hence the composite images generated therefrom will indicate significant changes in image content compared to the individual captured images and composite images corresponding to the upright PWSD user position of FIG. 12A, including significant changes in the presence, absence, positions, and/or orientations of objects in the PWSD user's external environment.

The PWSD 100 and/or the set of remote servers 500 can analyze multiple types of sensor signals in association with analyzing composite images that are temporally linked with the sensor signals to determine whether one or more sudden, significant, or dramatic changes have occurred in the sensor signals and composite images, where such change(s) can or are expected to indicate a sudden, significant, or dramatic change in the PWSD user's orientation.

Figure 12D:
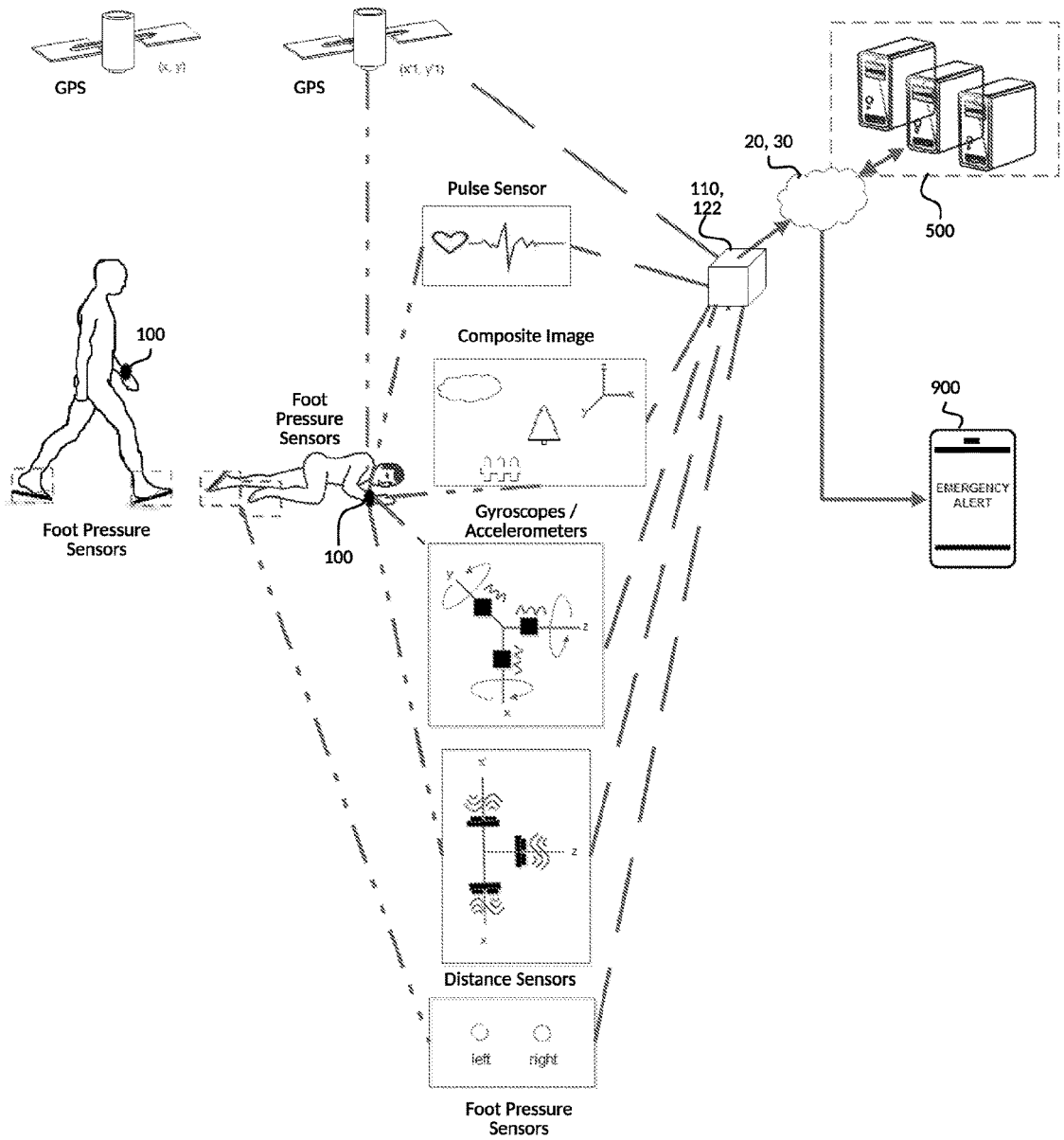

As indicated in FIG. 12D, the PWSD 100 and/or the set of remote servers 500 can additionally (e.g., concurrently) analyze particular PWSD user physiologic signals such as a pulse signal (e.g., a detected/measured PWSD user heart rate and pulse strength as a function of time), and possibly other physiologic signals such as PWSD user temperature or skin conductivity, in association with analyzing gyroscope/accelerometer signals, distance/proximity sensor measurements, footwear pressure sensor signals, and composite images to determine whether to send one or more alerts to a set of ARDs 900 associated with the PWSD user.

Aspects of Representative PWSD Charging and PWSD User Monitoring Processes

Figure 13A:
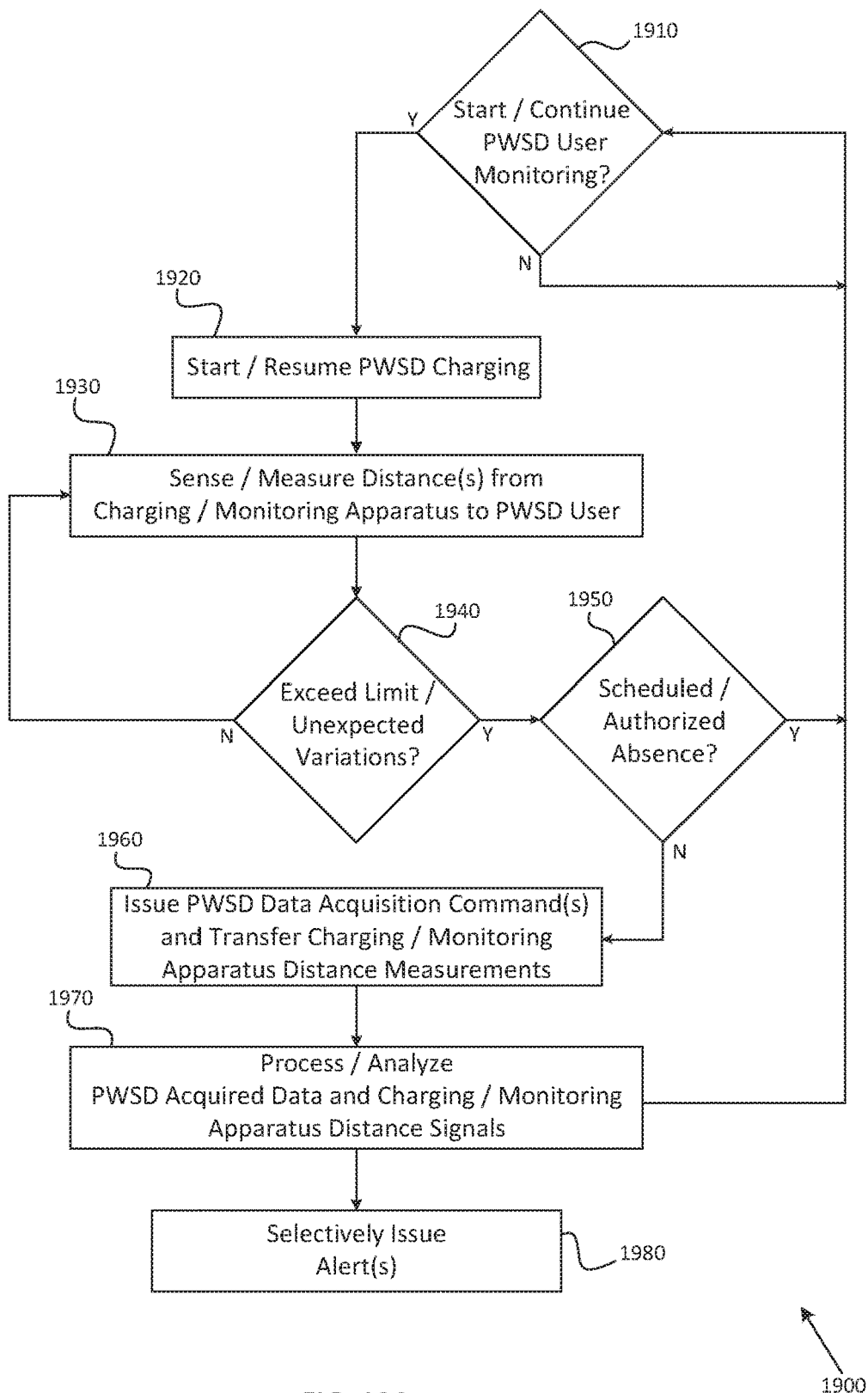
FIG. 13A is a flow diagram of a representative PWSD charging and user monitoring process in accordance with an embodiment of the present disclosure.

FIG. 13A is a flow diagram of a representative PWSD charging and user monitoring process 1900 in accordance with an embodiment of the present disclosure. In an embodiment, the process 1900 includes a first process portion 1910 in which the charging/monitoring apparatus 400 determines whether to (re)start PWSD user monitoring operations. Such determination can be based upon external input (e.g., from an electronic/computing system used by an individual responsible for monitoring the PWSD user, such as a nurse or caretaker), as well as the automatic detection of a PWSD user's presence on a support structure 402 with which the charging/monitoring apparatus 400 is associated. If PWSD user monitoring operations are not ready to commence or resume, the process 1900 remains at the first process portion 1910.

Once the charging/monitoring apparatus 400 determines that PWSD user monitoring operations can begin/resume, in a second process portion 1920 the charging/monitoring apparatus 400 begins/resumes PWSD charging by way of wireless energy transfer (e.g., magnetic induction). In a third process portion 1930, the charging/monitoring apparatus 400 senses/measures distances from itself to portions of the PWSD user's body, e.g., by way of one or more ultrasonic transducers. In a fourth process portion 1940, the charging/monitoring apparatus 400 determines whether sensed/measured distances have exceeded a selectable/programmable or predetermined limit (e.g., more than approximately 50 cm), or exhibit unexpected/atypical variations (e.g., sudden/sharp periodic behavior that is sustained for a given number of seconds, such as 5-10 seconds). If not, the process 1900 returns to the fourth process portion 1940.

If the charging/monitoring apparatus 400 determines that at least some of its sensed/measured distance signals exceeded a selectable/programmable or predetermined limit or exhibit unexpected/atypical variations, in a fifth process portion 1950 the charging/monitoring apparatus 400 determines whether the PWSD user is absent from the support structure 402 during a scheduled or authorized absence period. If the PWSD user is absent from the support structure 402 during a scheduled or authorized time period, the process 1900 returns to the first process portion 1910. Otherwise, in a sixth process portion 1960, the charging/monitoring apparatus 400 issues one or more PWSD data acquisition commands to the PWSD 100 and/or the remote server(s) 500. In association with the sixth process portion 1960, the charging/monitoring apparatus 400 can also transfer a series of most-recent distance measurements between portions of the PWSD user's body and the charging/monitoring apparatus to the PWSD 100 and/or the remote server(s) 500. After issuance of the PWSD data acquisition command, the PWSD 100 acquires sensed/measured signal sequences, captures multiple (x, y, z) image triplets, and performs multiple distance measurements in a manner essentially identical or analogous to that described above.

In a seventh process portion 1970, the PWSD 100 and/or the remote server(s) 500 process/analyze these sensed/measured signal sequences, multiple (x, y, z) image triplets (e.g., as composite images generated therefrom), and distance measurements, possibly in association with processing/analyzing the distance measurements generated by the charging/monitoring unit 400. The seventh process portion 1970 can include operations or processes that are essentially identical or analogous to those described above. In an eighth process portion 1980, the set of remote servers 500 selectively issues alerts to one target alert recipients, such as a nurse or caretaker responsible for monitoring the PWSD user, based upon such processing/analysis (e.g., in the event that the processing/analysis indicates that the PWSD user has left or is attempting to leave the support structure 402, or is experiencing physical difficulty for which intervention is required).

Figure 13B:
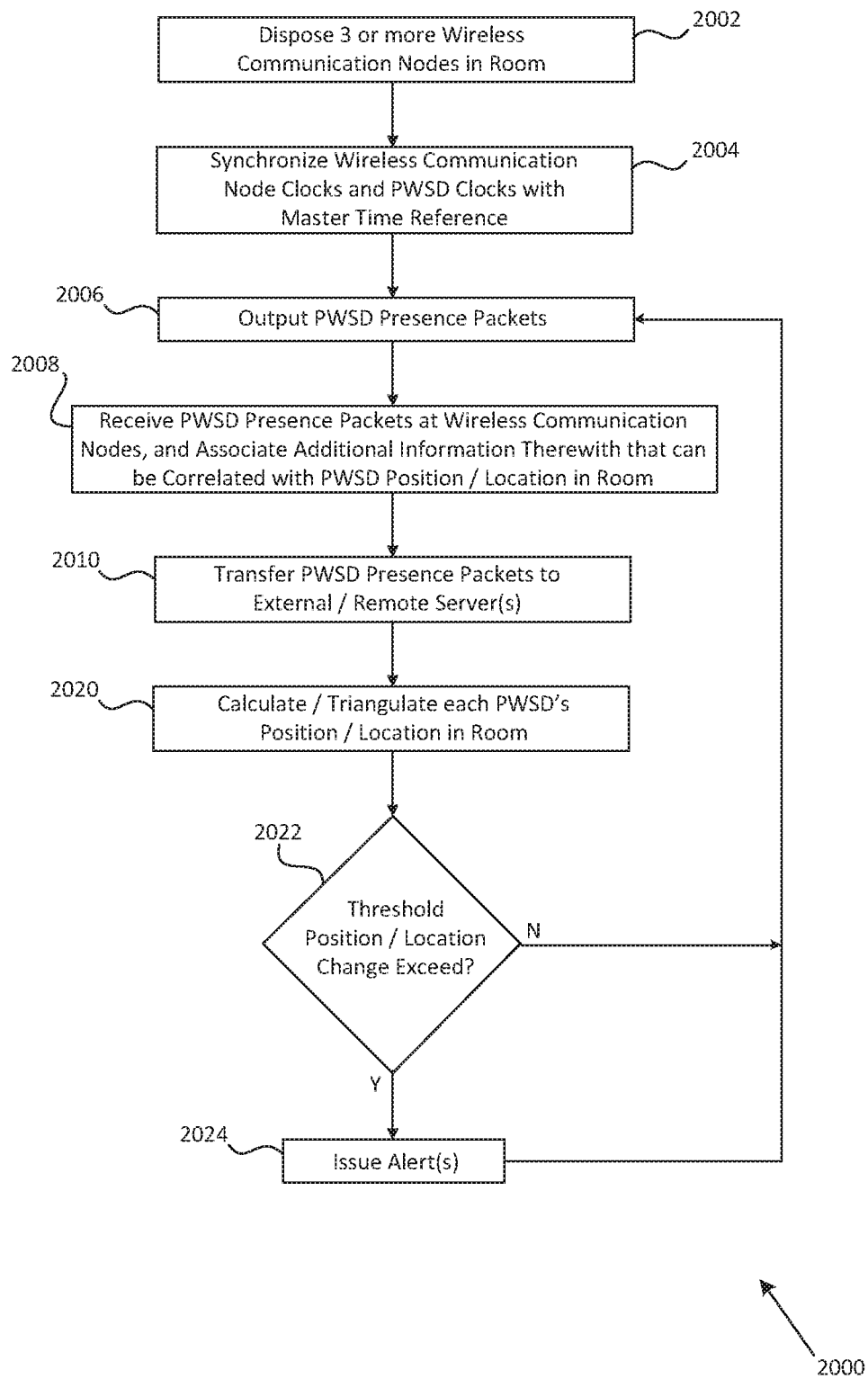
FIG. 13B is a flow diagram of a representative multi-PWSD monitoring process in accordance with an embodiment of the present disclosure.

FIG. 13B is a representative multi-PWSD monitoring process 2000 in accordance with an embodiment of the present disclosure. A first process portion 2002 involves disposing at least three wireless communication nodes 460 at particular locations within a known, controlled, and/or predetermined environment such as a room 452, where each wireless communication node 460 is configured for (a) receiving PWSD presence packets from PWSDs within range thereof in the room 452, as well as (b) communication with a set of external/remote servers 500. A second process portion 2004 involves coordinating or synchronizing an internal clock of each wireless communication node 460 and each PWSD 100 in the room 452 with a master timing reference, such as a master clock corresponding to the external/remote server(s) 500. A third process portion 2006 involves the generation and output of PWSD presence packets by each PWSD 100, where each such packet includes a PWSD ID and/or a MAC address corresponding to the PWSD 100 from which it was output, as well as a sending time stamp. A fourth process portion 2008 involves receipt of PWSD presence packets by the wireless communication nodes 460, the association of a receipt time stamp therewith for each such PWSD presence packet received, and/or possibly the association of a signal strength, magnitude, measure, or level for each such PWSD presence packet received. A fifth process portion 2010 involves communication of such PWSD presence packets from the wireless communication nodes 460 to the external/remote server(s) 500.

A sixth process portion 2020 involves external/remote server calculation/triangulation of each PWSD's position or location within the room 452 using or based on at least three of such PWSD presence packets. A seventh process portion 2022 involves external/remote server determination of whether a difference between a current, most-recent, or recent calculated/triangulated position or location of any PWSD 100 in the room 452 and an initial position or location calculated/triangulated for this PWSD 100 exceeds a threshold distance. If so, an eighth process portion 2024 involves issuing one or more alerts to a set of target alert recipients, such as a room administrator, caretaker, or nurse, where the alert(s) identify each PWSD 100 for which the threshold distance has been exceeded. After the eighth process portion 2024, or after the seventh process portion 2022 in the event that the calculated/triangulated position or location of each PWSD 100 in the room 452 remains within an acceptable, intended, expected, or safe distance relative to the initially calculated/triangulated position or location therefor, the process 2000 can return to the third process portion 2006.

Aspects of particular embodiments of the present disclosure address at least one aspect, problem, limitation, and/or disadvantage associated with existing portable/wearable smart devices directed to monitoring and analyzing user state(s), behavior(s), and/or environmental surroundings or orientation(s) therein. While features, aspects, and/or advantages associated with certain embodiments have been described in this disclosure, other embodiments may also exhibit such features, aspects, and/or advantages, and not all embodiments need necessarily exhibit such features, aspects, and/or advantages to fall within the scope of the present disclosure and the claims set forth below. In view of the present disclosure, a person having ordinary skill in the relevant art will understand that one or more of the above-disclosed systems, apparatuses, devices, components, elements, processes, modules, portions or alternatives thereof, and/or modifications or variations thereto, can be combined into other different systems, apparatuses, devices, elements, components, modules, processes, and/or applications that remain within the scope of the present disclosure and the following claims.

The invention claimed is:

1. A system for monitoring and/or analyzing physical states, positions, activities, and/or surroundings corresponding to a plurality of smart device users, the system comprising: a set of smart devices, each smart device portable or wearable by a corresponding smart device user, each smart device comprising:
   a first processing unit;
   a first set of sensors coupled to the first processing unit, the first set of sensors configured for acquiring or generating sensed signals corresponding to at least one physiologic parameter of the smart device user;
   a second set of sensors coupled to the first processing unit, the second set of sensors comprising at least one of an accelerometer, a gyroscope, and a geospatial coordinate sensor;
   a set of image capture devices coupled to the first processing unit, the set of image capture devices configured for capturing one or more images of an environment external to the smart device and generating image data corresponding to each captured image;
   a wireless communication subsystem coupled to the first processing unit; and a memory storing program instructions that when executed by the first processing unit cause the communication subsystem to wirelessly transmit sensed signals and image data to an electronic or computing destination remote from or external to the smart device;
   a set of servers configured for network communication with the set of smart devices, the set of servers comprising a second processing unit and a memory storing program instructions that when executed by the second processing unit analyze sensed signals and temporally associated image data received from each smart device to determine whether to issue an alert to a set of electronic or computing destinations associated with the smart device;
   a rechargeable power source; and
   a charging/monitoring unit comprising:
      a charging unit configured for recharging a power source of a first smart device; and
      a third set of sensors configured for measuring a distance between the charging/monitoring unit and a portion of the body of a first smart device user corresponding to the first smart device while the charging unit recharges the power source of the first smart device.

2. The system of claim 1, wherein the charging/monitoring unit includes a third processing unit and a memory storing a set of smart device user monitoring program instructions that when executed by the third processing unit determine whether a measured distance between the charging/monitoring unit and the first smart device user's body exceeds a threshold distance.

3. The system of claim 2, wherein when executed by the processing unit, the smart device user monitoring program instructions further communicate with the first smart device or the set of servers in the event that the threshold distance has been exceeded.

4. The system of claim 1 further comprising:
   at least three wireless communication nodes disposed in a controlled environment in which the set of smart devices resides, wherein each wireless communication node is configured for wireless communication with each smart device and communication with the set of servers, wherein the memory of each smart device further comprises program instructions configured for outputting smart device presence packets receivable by the at least three wireless communication nodes and processable by the set of servers to calculate or triangulate a current position of the smart device.

5. The system of claim 4, wherein the set of servers is configured for issuing an alert to a target electronic or computing destination in the event that a difference between a calculated or triangulated position of a smart device within the controlled environment and an initial calculated or triangulated position of the smart device within the controlled environment exceeds a threshold distance.

6. A method for monitoring and/or analyzing physical states, positions, activities, and/or surroundings corresponding to a set of smart device users, the method comprising:
   providing a set of smart devices, each smart device portable or wearable by a corresponding smart device user, each smart device comprising:
   a processing unit;
   a first set of sensors coupled to the processing unit, the first set of sensors configured for acquiring or generating sensed signals corresponding to at least one physiologic parameter of the smart device user;
   a second set of sensors coupled to the processing unit, the second set of sensors comprising at least one of an accelerometer, a gyroscope, and a geospatial coordinate sensor;
   a set of image capture devices coupled to the processing unit, the set of image capture devices configured for capturing one or more images of an environment external to the smart device and generating image data corresponding to each captured image;
   a wireless communication subsystem coupled to the processing unit; and
   a memory storing program instructions that when executed by the processing unit cause the communication subsystem to wirelessly transmit sensed signals and image data to an electronic or computing destination remote from or external to the smart device;
   providing a set of servers configured for network communication with each smart device, the set of servers comprising a processing unit and a memory storing program instructions that when executed by the processing unit enable wireless communication with each smart device;
   using the first set of sensors of each smart device to acquire or generate a first set of sensed signals corresponding to at least one physiologic state of the smart device user corresponding to the smart device;
   using the second set of sensors of each smart device to acquire a second set of sensed signals including at least one of accelerometer signals, gyroscope signals, and geospatial coordinates corresponding to the smart device;

using the set of image capture devices of each smart device to capture a set of images an environment external to the smart device and generate corresponding image data; and processing at least one of the first sensed signals and the second sensed signals generated or acquired by each smart device in association with processing the image data generated by the smart device to automatically determine whether the smart device user corresponding to the smart device is experiencing an atypical or emergency situation or requires assistance;

wherein each smart device includes a rechargeable power source, and wherein the method further comprises:

providing a charging/monitoring unit corresponding to at least a first smart device, the charging/monitoring unit comprising:

a charging unit configured for recharging the power source of a first smart device; and a set of sensors configured for measuring a distance between the charging/monitoring unit and a portion of the body of a first smart device user corresponding to the first smart device;

measuring a set of distances between the charging/monitoring unit and the portion of the body of the first smart device user while the charging unit recharges the power source of the first smart device; and determining whether a distance between the charging/monitoring unit and the portion of the body of the first smart device user exceeds a threshold distance.

7. The method of claim 6, further comprising using each smart device to process the first sensed signals and second sensed signals acquired or generated thereby to determine a likelihood of whether an atypical or emergency condition corresponding to the smart device or the smart device user likely exists, wherein capturing images and generating corresponding image data representing portions of an environment external to the smart device is selectively performed based on whether an atypical or emergency condition corresponding to the smart device or the smart device user likely exists.

8. The method of claim 7, wherein using each smart device to capture the set of images representing portions of an environment external to the smart device comprises (a) capturing at least one image using a single wide angle camera unit, or (b) capturing a plurality of images using a plurality of cameras and/or wide angle camera units in which each camera or wide angle camera unit has a field of view (FoV) that is distinguishable from the FoV of each other camera or wide angle camera unit, and which partially overlaps with the FoV of another camera or wide angle camera unit.

9. The method of claim 6, wherein using each smart device to capture the set of images representing portions of an environment external to the smart device comprises (a) capturing at least one image using a single wide angle camera unit, or (b) capturing a plurality of images using a plurality of cameras and/or wide angle camera units in which each camera or wide angle camera unit has a field of view (FoV) that is distinguishable from the FoV of each other camera or wide angle camera unit, and which partially overlaps with the FoV of another camera or wide angle camera unit.

10. The method of claim 9, wherein the FoV of each camera or wide angle camera unit within the plurality of cameras and/or wide angle camera units overlaps with the FoV of another camera or wide angle camera unit within the plurality of cameras and/or wide angle camera units by less than 30%.

11. The method of claim 9, wherein each image within the plurality of images is captured simultaneously, essentially simultaneously, or in rapid succession with respect to each other image within the plurality of images.

12. The method of claim 11, further comprising digitally stitching together image data corresponding to individual images within the plurality of images to generate image data of a single or unified composite image.

13. The method of claim 12, wherein processing at least one of the first set of sensed signals and the second set of sensed signals in association with processing the image data comprises analyzing at least one of the first set of sensed signals and the second set of sensed signals, plus analyzing the image data of the composite image.

14. The method of claim 6, further comprising issuing an alert to a target electronic or computing destination in the event that the threshold distance is exceeded.

15. The method of claim 6, further comprising:

disposing at least three wireless communication nodes at known positions in a controlled environment in which the set of smart devices resides, wherein each wireless communication node is configured for wireless communication with each smart device and communication with the set of servers;

outputting smart device presence packets from each smart device;

receiving a first set of smart device presence packets output by a first smart device at a minimum of three wireless communication nodes; and processing the first set of smart device presence packets to calculate or triangulate a current position of the first smart device within the controlled environment.

16. The method of claim 15, further comprising:

determining whether a difference between calculated or triangulated position of the first smart device within the controlled environment and an initial calculated or triangulated position of the first smart device within the controlled environment exceeds a threshold distance; and issuing an alert to a target electronic or computing destination in the event that the threshold distance has been exceeded.

* * * * *